US011810646B2

(12) United States Patent
Lou et al.

(10) Patent No.: US 11,810,646 B2
(45) Date of Patent: *Nov. 7, 2023

(54) SYNTHETIC BIOLOGY TOOLS

(71) Applicant: The Regents of the University of California, Oakland, CA (US)

(72) Inventors: Chunbo Lou, San Francisco, CA (US); Tae Seok Moon, San Francisco, CA (US); Virgil Rhodius, El Sobrante, CA (US); Brynne Stanton, San Francisco, CA (US); Alvin Tasmir, San Francisco, CA (US); Karsten Temme, San Francisco, CA (US); Chris Voigt, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 569 days.

This patent is subject to a terminal disclaimer.

(21) Appl. No.: 16/789,993

(22) Filed: Feb. 13, 2020

(65) Prior Publication Data

US 2021/0005279 A1  Jan. 7, 2021

Related U.S. Application Data

(63) Continuation of application No. 15/064,206, filed on Mar. 8, 2016, now Pat. No. 10,607,716, which is a continuation of application No. 13/489,205, filed on Jun. 5, 2012, now abandoned.

(60) Provisional application No. 61/493,733, filed on Jun. 6, 2011.

(51) Int. Cl.
| | |
|---|---|
| *C12N 5/00* | (2006.01) |
| *G16B 20/30* | (2019.01) |
| *G16B 20/00* | (2019.01) |
| *G16B 30/00* | (2019.01) |
| *G16B 35/00* | (2019.01) |
| *G16C 20/60* | (2019.01) |
| *C12N 15/63* | (2006.01) |
| *G16B 35/10* | (2019.01) |
| *G16B 30/20* | (2019.01) |
| *C12N 15/70* | (2006.01) |
| *C12N 15/79* | (2006.01) |
| *G16B 20/50* | (2019.01) |

(52) U.S. Cl.
CPC ............ *G16B 20/30* (2019.02); *C12N 15/63* (2013.01); *C12N 15/635* (2013.01); *C12N 15/70* (2013.01); *C12N 15/79* (2013.01); *G16B 20/00* (2019.02); *G16B 30/00* (2019.02); *G16B 30/20* (2019.02); *G16B 35/00* (2019.02); *G16B 35/10* (2019.02); *G16C 20/60* (2019.02); *G16B 20/50* (2019.02)

(58) Field of Classification Search
CPC ........ G16B 20/30; G16B 35/10; G16B 20/00; G16B 30/20; G16B 30/00; G16B 35/00; G16B 20/50; G16C 20/60; C12N 15/63; C12N 15/635; C12N 15/70; C12N 15/79
See application file for complete search history.

(56) References Cited

U.S. PATENT DOCUMENTS

| 5,385,834 A | 1/1995 | Ikeda |
|---|---|---|
| 5,851,796 A | 12/1998 | Schatz |
| 6,132,969 A | 10/2000 | Stoughton et al. |
| 6,774,222 B1 * | 8/2004 | Schneider ............. B82Y 10/00 536/23.1 |
| 8,685,687 B2 | 4/2014 | Barbas, III et al. |
| 10,607,716 B2 | 3/2020 | Lou et al. |
| 2005/0003354 A1 | 1/2005 | Wilkinson et al. |
| 2007/0161031 A1 | 7/2007 | Trinklein et al. |
| 2007/0196816 A1 * | 8/2007 | Schwartz ............... C07K 19/00 435/254.2 |
| 2010/0016172 A1 | 1/2010 | Ansari |
| 2010/0040649 A1 | 2/2010 | Berkhout et al. |
| 2010/0086532 A1 | 4/2010 | Barbas, III et al. |
| 2010/0223276 A1 | 9/2010 | Al-Shameri et al. |
| 2010/0255561 A1 | 10/2010 | Steinmetz et al. |
| 2010/0291648 A1 | 11/2010 | Alper et al. |
| 2011/0071047 A1 | 3/2011 | Ma et al. |
| 2013/0005590 A1 | 1/2013 | Lou et al. |
| 2016/0292355 A1 | 10/2016 | Lou et al. |

OTHER PUBLICATIONS

Tamsir et al. in "Robust multicellular computing using genetically encoded NOR gates and chemical wires" (Nature Jan. 13, 2011: vol. 469, No. 7329, pp. 1-9; published online Dec. 8, 2010). (Year: 2010).*
de las Heras et al in "Engineering input/output nodes in prokaryotic regulatory circuits" (FEMS Microbiol Rev; 2010 vol. 34, pp. 842-865). (Year: 2010).*
Silva-Rocha & de Lorenzo in "Implementing an OR-NOT (ORN) logic gate with components of the SOS regulatory network of *Escherichia coli*" (Molecular BioSystems 2011, vol. 7, pp. 2389-2396). (Year: 2011).*
Hermsen et al (PloS Computational Biology Jun. 2010, vol. 6, No. 6, pp. 1-13. (Year: 2010).*
U.S. Appl. No. 13/489,205 , "Final Office Action", dated Oct. 8, 2015, 35 pages.
U.S. Appl. No. 15/064,206 , "Final Office Action", dated May 10, 2018, 26 pages. U.S. Appl. No. 15/064,206 , "Non-Final Office Action", dated Feb. 21, 2019, 12 pages.
U.S. Appl. No. 15/064,206 , "Non-Final Office Action", dated Sep. 21, 2017, 21 pages.
U.S. Appl. No. 15/064,206 , "Notice of Allowance", dated Nov. 20, 2019, 7 pages.
Baker et al., "Extensive DNA-Binding Specificity Divergence of a Conserved Transcription Regulator", Proc. Natl. Acad. Sci., vol. 108, No. 18, May 3, 2011, pp. 7493-7498.
Darwin et al., "Type III Secretion Chaperone-Dependent Regulation: Activation of Virulence Genes by SicA and InvF in Salmonella Typhimurium", The EMBO Journal, vol. 20, No. 8, Apr. 2001, pp. 1850-1862.

(Continued)

Primary Examiner — Catherine S Hibbert
(74) Attorney, Agent, or Firm — Kilpatrick Townsend & Stockton LLP

(57) ABSTRACT

Methods for design of genetic circuits are provided.

7 Claims, 37 Drawing Sheets

Specification includes a Sequence Listing.

(56) References Cited

OTHER PUBLICATIONS

Giancarlo et al., "Textual Data Compression in Computational Biology: a Synopsis", Bioinformatics, vol. 25, No. 13, Jul. 2009, pp. 1575-1586.
PCT/US2012/040939, "International Search Report and Written Opinion", dated Oct. 23, 2012, 13 pages.
Sousa et al., "Single Crystals of a Chimeric T7/T3 RNA Polymerase with T3 Promoter Specificity and a Nonprocessive T7 RNAP Mutant", The Journal of Biological Chemistry, vol. 265, No. 35, Dec. 1990, pp. 21430-21432.
Steggles et al., "Qualitatively Modeling and Analysing Genetic Regulatory Networks: a Petri Net Approach", Bioinformatics, vol. 23, No. 3, Feb. 2007, pp. 336-343.
Yokobayashi et al., "Directed evolution of a genetic circuit", PNAS vol. 99, No. 26, 2002, pp. 16587-16591.

* cited by examiner

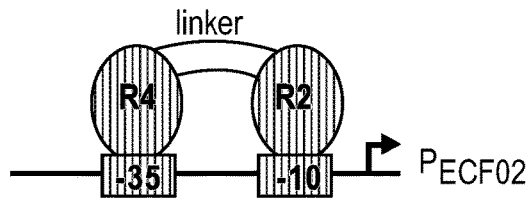
Sigma ECF02_2817
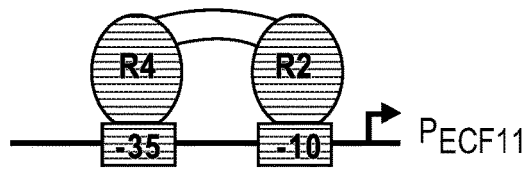
Sigma ECF11_3726
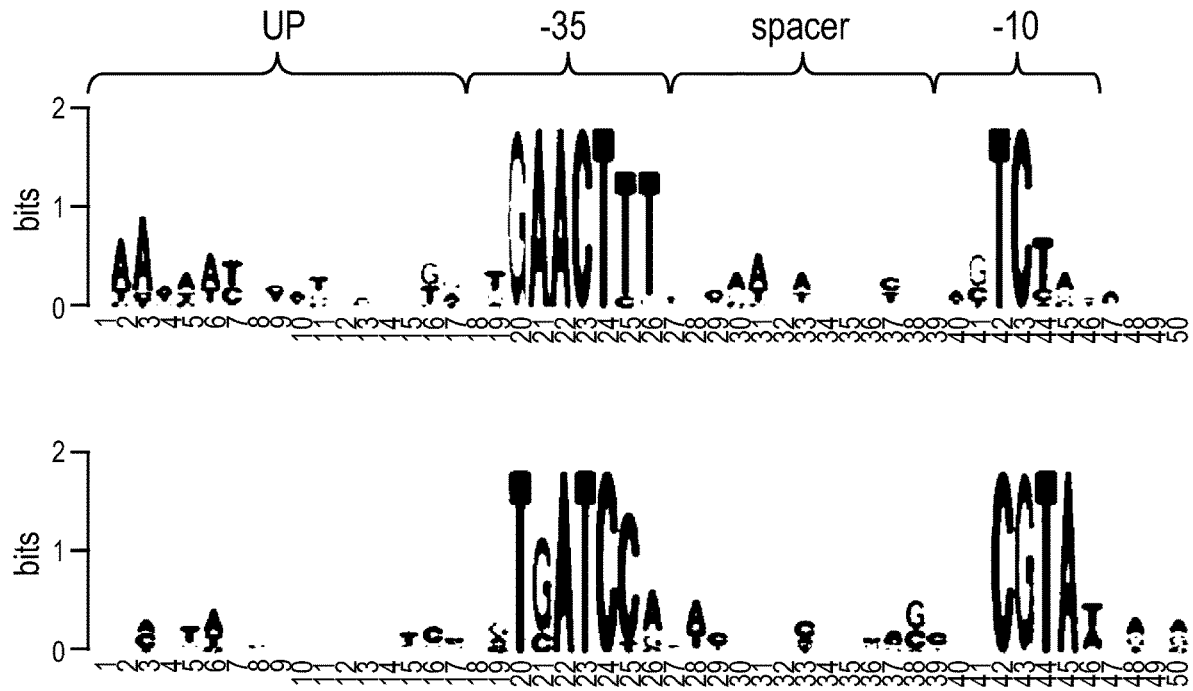
FIG. 9

Chimera ECF02_ECF11
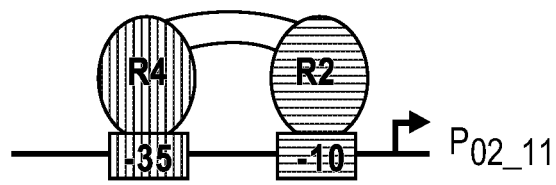
Chimera ECF11_ECF02
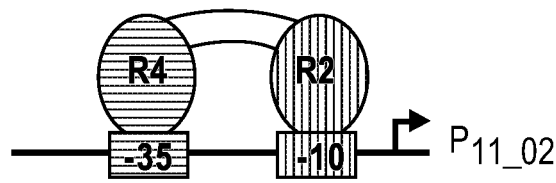
FIG. 10

|  | Sigma-factor construct | | | |
|---|---|---|---|---|
| Promoter construct: | 02 | 11 | 02_11 | 11_02 |
| $P_{02}$ | 1000 | 1 | | |
| $P_{11}$ | 1 | 200 | | |
| $P_{02-11}$ | | 1 | 32 | 1 |
| $P_{11-02}$ | | 1 | 1 | 126 |

*Above values indicate fold-change over background

|   | 1 | 2 | 3 | 4 | 5 | 6 | 7 | 8 | 9 | 10 | 11 | 12 |
|---|---|---|---|---|---|---|---|---|---|---|---|---|
| A | 1133 | 1175 | 1226 | 62.4 | 1064 | 1180 | 1196 | 1180 | 1188 | 1143 | 1161 | 1073 |
| B | 1160 | 1136 | 1103 | 1066 | 1107 | 1085 | 1115 | 1137 | 1139 | 1135 | 1085 | 1131 |
| C | 1188 | 1194 | 1168 | 1175 | 1164 | 1169 | 1142 | 1193 | 1201 | 1187 | 1209 | 1214 |
| D | 1194 | 986 | 1126 | 1133 | 1148 | 1118 | 1151 | 1172 | 1151 | 1112 | 1123 | 1148 |
| E | 1249 | 1161 | 1145 | 1142 | 1151 | 1174 | 1160 | 1171 | 1173 | 1170 | 1193 | 1194 |
| F | 1249 | 1210 | 1192 | 1196 | 1178 | 1190 | 1167 | 1127 | 859 | 861 | 914 | 886 |
| G | 1168 | 1226 | 1174 | 1197 | 1217 | 1165 | 1168 | 1142 | 1186 | 1166 | 1122 | 1175 |
| H | 1256 | 1155 | 1121 | 1184 | 1209 | 1196 | 1213 | 1166 | 1231 | 1136 | 1022 |   |

FIG. 15

| Scaffold Name | Modifications | Relative Toxicity |
|---|---|---|
| N77 | IncW plasmid<br>ATG start codon and RBS found in DE3 strains (AATTGTGAGCGGATAACAA) | Comparable to DE3 strains<br>+++++ |
| N115 | N77 + Full length UmuD tag (atgttgtttatcaagcctgcggatctccgcgaaattgtgactttttccgctatttagcgatcttgttcagtgtggcttttccttcacc ggcagcagattacgttgaacagcgcatcgatctg) | ++ |
| N121 | N77 + Truncated UmuD tag (atgttgtttatcaagcctgcggatctccgcgaaattgtgactttttccgctatttagcgatcttgttcagtgtggc) | ++++ |
| N130 | N77 + Mutated full length UmuD tag (atgttgtttatcaagcctgcggatctccgcgaaattgtgactgccgcggcagcgagcgatctt gttcagtgtggcttttccttcacc ggcagcagattacgttgaacagcgcatcgatctg | +++ |
| N219 vB11 | N115 + GTG start codon and removed lacO site | + |
| N249 | N219 vB11 with R632S active site mutation, weak RBS (identified from a library: TATCCAAACCAGTAGCTCAATTGGAGTCGTCTAT), a random DNA spacer to insulate the RNAP from upstream promoter swaps (TGCAGTTTTATTCTCTCGCCAGCACTGTAATAGGCACTAA) | - |

FIG. 17

| Promoter Name | Sequence TAATACGACTCACTANNNNNAGA | Strength (2009.10.02 to 2009.10.09) |
|---|---|---|
| WT | TAATACGACTCACTATAGGGAGA | 5263 |
| Mut1 | TAATACGACTCACTACAGGCAGA | 365 |
| Mut2 | TAATACGACTCACTAGAGAGAGA | 366 |
| Mut3 | TAATACGACTCACTAATGGGAGA | 577 |
| Mut4 | TAATACGACTCACTATAGGTAGA | 1614 |
| Mut5 | TAATACGACTCACTAAAGGGAGA | 1018 |
| Mut6 | TAATACGACTCACTATTGGGAGA | 3216 |

FIG. 18

| Terminator Name | Sequence TANNNNAACCSSWWSSSSSTCWWW WCGSSSSSSWWSSGGTTTTTGT | Strength (2009.12.16 Assay) |
|---|---|---|
| 52 | TATAAAACGGGGGGCTAGGGGTTTTT GT | 107 |
| 23 | TACTCGAACCCCTAGCCCGCTCTTATC GGGCGGCTAGGGGTTTTTGT | 714 |
| 72 | TAGCAGAAACCGCTAACGGGGCGAAG GGGTTTTTGT | 1051 |
| 48 | TACTCGAACCCCTAGCCCGCTCTTATC GGGCGGCTAGGGGTTTTTGT | 1131 |
| 1 | TACATATCGGGGGGGGTAGGGGTTTTT GT | 1297 |
| 2 | TACATATCGGGGGGGGTAGGGGTTTTT GT | 1333 |
| WT | TAGCATAACCCCTTGGGCCTCTAAAC GGGTCTTGAGGGTTTTTGT | 1395 |
| 31 | TACCCTAACCCCTTCCCGGTCAATCG GGGCGGATGGGGTTTTTGT | 1586 |
| 58 | TAGACCAACCCCTTGCGCCTCAATCG GGGGGATGGGGTTTTTGT | 1608 |
| 25 | TACTCTAACCCCATCGGCCGTCTTAGG GGTTTTTGT | 1609 |
| 17 | TACCTCAACCCCTTCCGCCCTCATATC GCGGGGCATGCGGGTTTTTGT | 1887 |

FIG. 19

| RNAP Family | Scaffold | RNAP Plasmid | Promoter Plasmid | Loop Sequence | Promoter Sequence |
|---|---|---|---|---|---|
| T7 | N249 | N249 | N155 | VWQEYKKPIQTRLNLMFLGQFRLQPTINTNKDSEIDAHK | TAATACGACTCACTATAGGGAGA |
| T3 | N115 | N377:115 | N352 | VWQEYKKPIQKRLDMIFLGQFRLQPTINTNKDSEIDAHK | TAATAACCCTCACTATAGGGAGA |
| K1F | N115 | N421:115 | N353 | VWQEYKKPIQTRLNLMFLGSFNLQPTVNTNKDSEIDAHK | TAATACTATCACTATAGGGAGA |
| N4 | N77 | W78 | W74 | VWQEYKKPIQTRIDCVLGTHRMALTINTNKDSEIDAHK | TAATAACGACACTATAGGGAGA |

FIG. 20A

| | T7 promoter | T3 promoter | K1F promoter | N4 promoter |
|---|---|---|---|---|
| T7 RNAP | 2177 | 24 | 17 | 14 |
| T3 RNAP | 83 | 1062 | 14 | 14 |
| K1F RNAP | 45 | 26 | 463 | 13 |
| N4 RNAP | 51 | 147 | 46 | 2616 |

FIG. 20B

| Specificity: Strength | Sequence TAATACGACTCACTA+CAGGCAGA | Activity with T7 RNAP | Activity with T3 RNAP |
|---|---|---|---|
| T7:Mut1 | TAATACGACTCACTACAGGCAGA | 51 | 29.2 |
| T7:Mut2 | TAATACGACTCACTAGAGAGAGA | 256 | 28 |
| T7:Mut3 | TAATACGACTCACTAATGGGAGA | 420 | 39 |
| T7:Mut4 | TAATACGACTCACTATAGGTAGA | 1083 | 87 |
| T7:Mut5 | TAATACGACTCACTAAAAGGGAGA | 1142 | 123 |
| T7:Mut6 | TAATACGACTCACTATTGGGAGA | 3400 | 68 |
| T3:Mut1 | TAATAACCCTCACTACAGGCAGA | 19.7 | 351 |
| T3:Mut2 | TAATAACCCTCACTAGAGAGAGA | 15.7 | 1191 |
| T3:Mut3 | TAATAACCCTCACTAATGGGAGA | 14.4 | 1372 |
| T3:Mut4 | TAATAACCCTCACTATAGGTAGA | 18.1 | 2624 |
| T3:Mut5 | TAATAACCCTCACTAAAAGGGAGA | 19.1 | 2809 |
| T3:Mut6 | TAATAACCCTCACTATTGGGAGA | 19.1 | 2913 |

FIG. 21

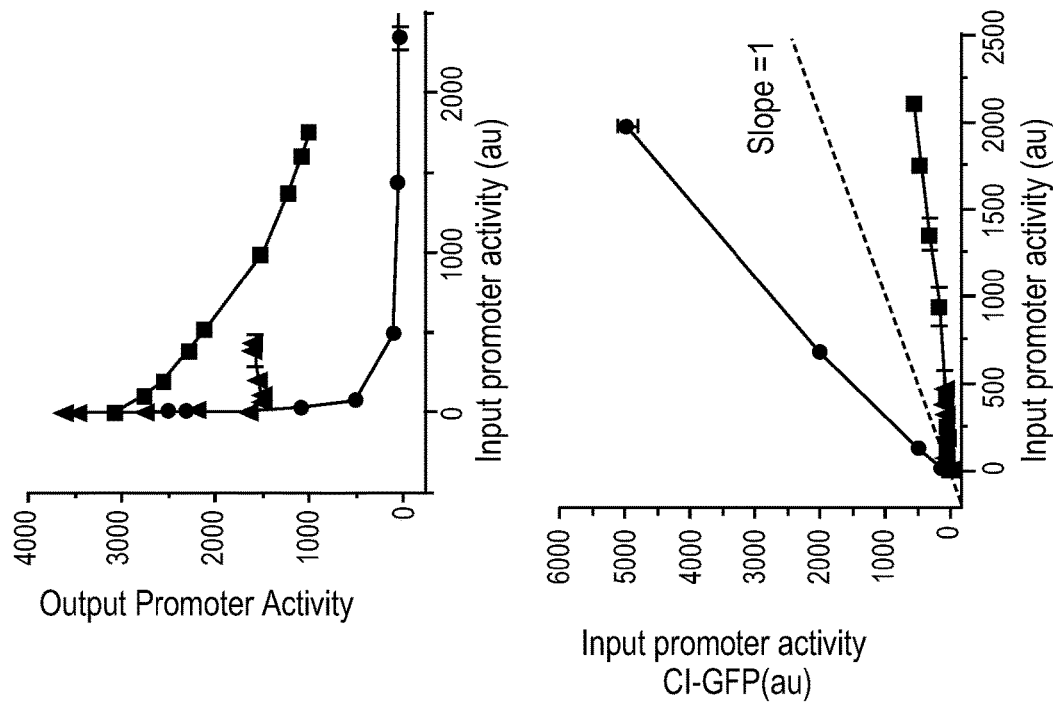
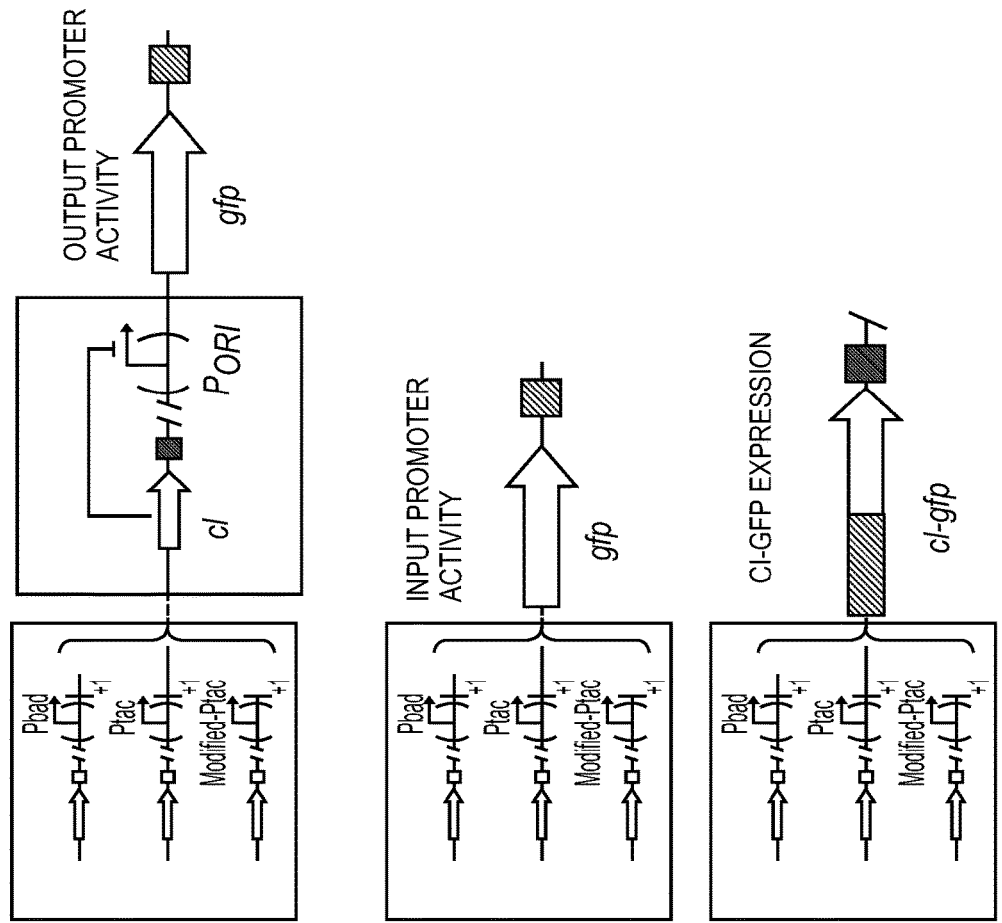
FIG. 23

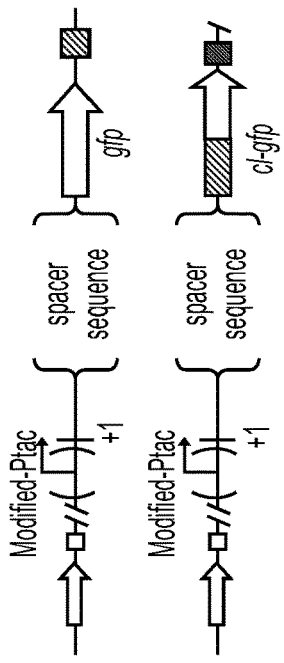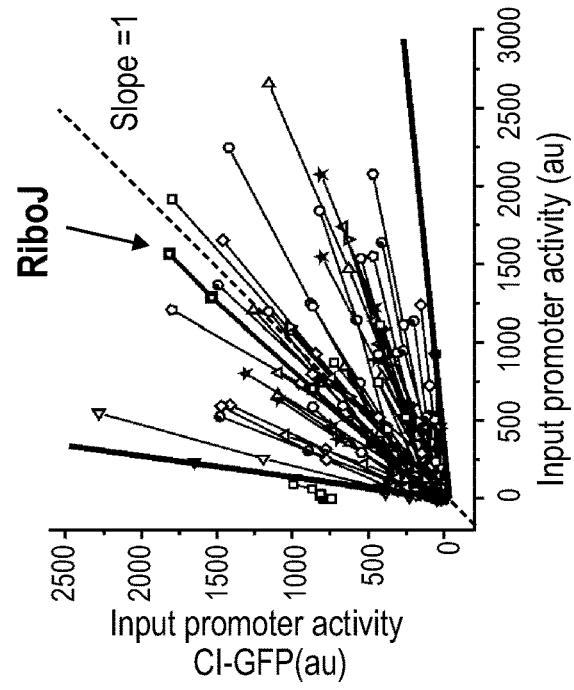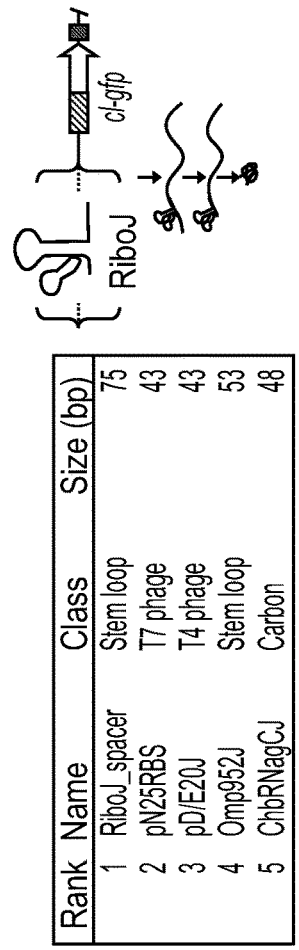
FIG. 24

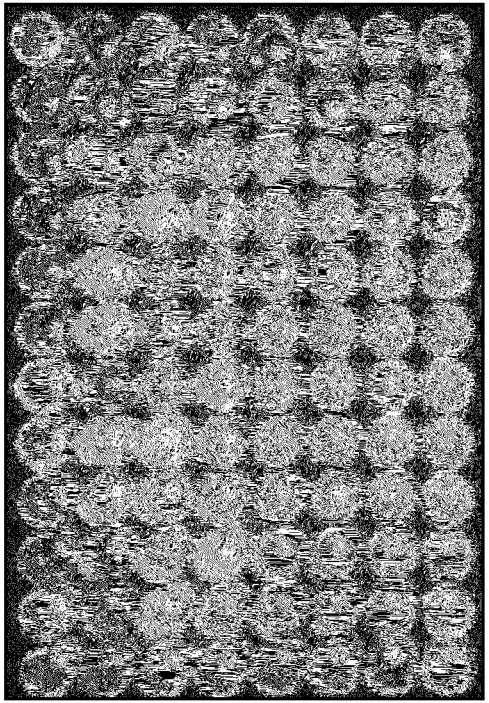
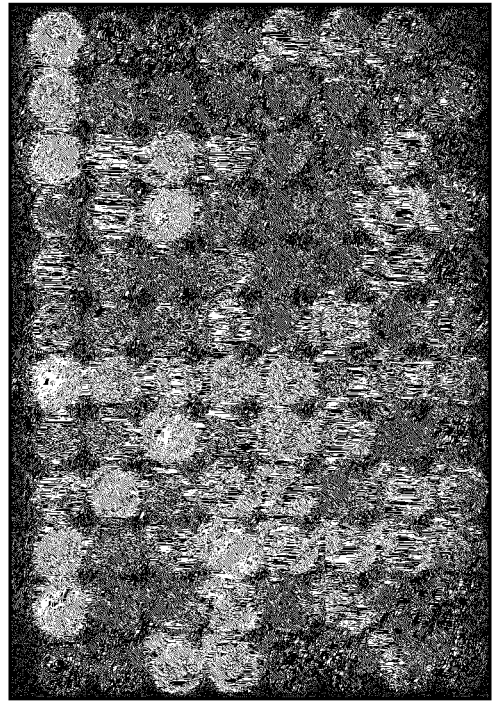
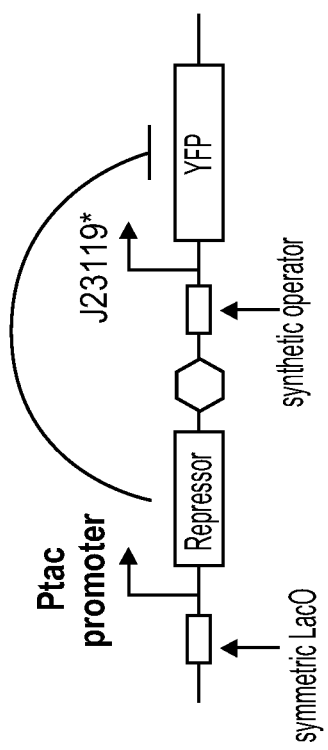
Degenerate RBS library:
TCACACGGAAAKRCYWSG
FIG. 30

SYNTHETIC BIOLOGY TOOLS

CROSS-REFERENCE TO RELATED PATENT APPLICATIONS

This application is a continuation of U.S. application Ser. No. 15/064,206, filed Mar. 8, 2016 which is a continuation of U.S. application Ser. No. 13/489,205, filed Jun. 5, 2012, which claims benefit of priority to U.S. Provisional Patent Application No. 61/493,733, filed on Jun. 6, 2011, each of which are incorporated by reference.

STATEMENT AS TO RIGHTS TO INVENTIONS MADE UNDER FEDERALLY SPONSORED RESEARCH AND DEVELOPMENT

This invention was made with government support under grant no. EEC-0540879 awarded by the National Science Foundation. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 081906_1178040_Sequence_Listing.txt, created on Feb. 11, 2020, 79,383 bytes, machine format IBM-PC, MS-Windows operating system, is hereby incorporated by reference in its entirety for all purposes.

BACKGROUND OF THE INVENTION

Genetically programming cells require sensors to receive information, circuits to process the inputs, and actuators to link the circuit output to a cellular response (Andrianantoandro E, et al., *Mol Syst Biol* 2 (2006); Chin J W *Curr Opin Struct Biol* 16: 551-556 (2006); Voigt C A *Curr Opin Biotech* 17: 548-557 (2006); Tan C, *Mol Biosyst* 3: 343-353 (2007)). In this paradigm, sensing, signal integration, and actuation are encoded by distinct 'devices' comprised of genes and regulatory elements (Knight T K, Sussman G J *Unconventional Models of Computation* 257-272 (1997); Endy D *Nature* 438: 449-453 (2005)). These devices communicate with one another through changes in gene expression and activity. For example, when a sensor is stimulated, this may lead to the activation of a promoter, which then acts as the input to a circuit.

BRIEF SUMMARY OF THE INVENTION

Embodiments of the present invention provide methods of designing a genetic circuit containing one or more orthogonal sequence-specific DNA binding polypeptides. In some embodiments, the method comprises:
providing a set of sequence-specific DNA binding polypeptides;
optimizing expression of the polypeptides in a heterologous host cell;
identifying target DNA sequences to which the polypeptides bind;
generating synthetic transcriptional regulatory elements comprising at least one identified target DNA sequence, wherein the regulatory elements are responsive to a sequence-specific DNA binding polypeptide from the set of sequence-specific DNA binding polypeptides;
designing cognate sequence-specific DNA binding polypeptide-target DNA sequence pairs to generate a set of orthogonal sequence-specific DNA binding polypeptide-target DNA sequence pairs; and
designing a genetic circuit containing one or more orthogonal sequence-specific DNA binding polypeptide-target DNA sequence pairs from the set of orthogonal sequence-specific DNA binding polypeptide-target DNA sequence pairs, thereby designing a genetic circuit containing one or more orthogonal sequence-specific DNA binding polypeptides.

Embodiments of the present teachings provide methods to identify, design and modify wild type DNA, RNA and protein sequences for the development of collections of characterized genetic circuit elements that can be reused in many future designs. In some embodiments the method comprises:
Identifying a natural or synthetic biomolecule with desired functional characteristics
Identifying similar molecules through comparative analysis
Employing tools to optimize the molecules for performance and expression. In some embodiments this will include optimizing the sequence for expression in a non native host. In some embodiments this will include use of computational tools to identify ways to modify add, remove, increase or reduce sequence changes with resultant functional significance for the expressed sequences. In some embodiments this will result in combination of functional domains from different wild type and synthetic molecules to create novel molecules with new functional behaviours.
Amplifying or synthesizing such molecules. In some embodiments these molecules will be designed to include modifications such as experimental tags or elements to facilitate future experimental identification and handling.
Combining such molecules with other genetic circuit elements to develop gene like elements termed devices. In some embodiments this will include the use of the software to assist with the design of such devices.
Combining such molecules to other genetic circuit elements or devices in order to create genetic circuits. In some embodiments this will include the use of the software to assist with the design of such genetic circuits.
Insertion of such molecules into standardized assays to evaluate their performance. In some embodiments data from the assays will be used to assess selection of genetic circuit elements as part of a design.
Reuse of such molecules in standardized assembly methodologies. In some embodiments this will include identification of host the elements will be optimized for. In some embodiments this will include experimental methodologies that the elements will be assembled with. In some embodiments this will include the experimental methodologies the elements will be verified and validated with.
Modification and Mutation of Standardized Molecules to Introduce New Functional Characteristics and Develop New Variants of these Molecules Embodiments of the present teachings provide methods for describing, classifying and characterizing the elements of a genetic circuit to aid in the design of genetic circuits. Genetic element data may be stored locally or in a server in a memory or database.

Genetic element data may be generated for describing the genetic circuit element, the classification of the element for its functional role and the characterization of the genetic element for its experimental performance. Genetic element data is a formalized description of the data necessary to describe a genetic element in a standardized format. In some embodiments, genetic element data can be used to share and distribute information about a genetic circuit element. In some embodiments genetic element data represent the data model for how a genetic circuit element can be used in design of a genetic circuit element. In some embodiments the genetic element data can be used to augment design of a genetic circuit element through use of classification terms. In some embodiments the genetic element data can be used to augment circuit design through use of experimental characterization data. In some embodiments the genetic element data will describe an assembly of genetic circuit elements into a functional unit, termed a device. In some embodiments the genetic element data will describe an assembly of devices into a genetic circuit.

Embodiments of the present teachings provide a means to standardize the classification of genetic circuit elements through use of defined terms. Some embodiments use a formalized grammar. Some embodiments use an ontology.

Embodiments of the present teachings provide a means to standardize the experimental characterization of a genetic circuit element through use of standardized assays and standardized reporting of measurements of performance from such assays. In some embodiments this may include the production of instructions for robots.

Embodiments described herein provide a means to develop biophysical models of genetic circuit elements, devices and genetic circuits. Such models can be used in scanning for existing functional characteristics of elements of a genetic circuit design. In some embodiments biophysical models can be used to design desired functional properties into genetic circuit elements, devices and genetic circuits. In some embodiments biophysical models can contribute to modeling and simulating the likely performance of these elements in a genetic circuit design. In some embodiments biophysical models can be used to evaluate the performance of genetic circuit elements, devices and genetic circuits in the target host system.

Embodiments of the described herein provide a means to standardize the design of a genetic circuit through the use of design rules. Such design rules embody the ways with which genetic circuit elements can be combined to form a device. Such design rules embody the ways with which devices can be combined to for a genetic circuit. Such design rules embody the ways with which genetic circuits sense inputs from the cell, process such inputs within the circuit and provide responses to the processing of the inputs. In some embodiments design rules can be achieved through use of optimization algorithms.

Embodiments of the present teachings provide a means to develop, classify and standardize the design of genetic circuits used to assay genetic design elements.

Embodiments of the present teachings provide a means to encode and characterize the experimental data resulting from assay measurements so that they can be included as part of the characterization data within a genetic element data. In some embodiments this may include single variable analysis measurements. In some embodiments this may include multiple variable analyses measurements. In some embodiments this may include results from analyses. In some embodiments this may include mathematical formulas or algorithms.

Embodiments of the present teachings provide a means to compare, sort, filter, exclude and otherwise select and manipulate parts based upon the information included in their genetic element data.

Embodiments of the present teachings provide a means to use developed genetic circuit elements, devices and circuits as template design templates. Design templates can be used as archetypal and reusable solutions for genetic circuits. Design templates are associated with assembled DNA molecules. Implementation of the design is realized through assembly of the corresponding DNA molecules. Reuse of the design templates is realized through reuse of the assembled DNA molecules in further experimental manipulations.

Embodiments of the present teachings provide a means to simulate design of devices and circuits in silico to identify and discover designs that may detect desired inputs, process these detected inputs in a predictable manner and respond to the processing by producing a desired output. In some embodiments, this may include the identification, reduction and elimination of design issues between genetic circuit elements and devices; between genetic circuit elements, devices and circuits; between genetic circuit elements, devices and the target host. In some embodiments, this may include the ability to identify and remove, redesign or avoid issues that may result in non orthogonality between the different elements of the design. In some embodiments, the inputs may include molecules present in the cell, such as chemicals, metabolites, DNAs, RNAs, proteins, carbohydrates and lipids. In some embodiments, the inputs may include external queues that act upon the cell, such as cellular-cellular queues, environmental queues and chemical queues. In some embodiments the outputs may includes and interact with molecules present in the cell, such as chemicals, metabolites, DNAs, RNAs, proteins, carbohydrates and lipids. In some embodiments, the outputs may include and interact with external queues that act upon the cell, such as cellular-cellular queues, environmental queues and chemical queues.

Embodiments of the present teachings provide systems and methods to simulate the design, preparation for and execution of experiments to assemble DNA sequences corresponding to the designed genetic circuit elements, devices and circuits. In some embodiments, this may permit the comparison and combination of different assembly technologies to identify the most efficient path for assembly. In some embodiments, this may include the communication of such data to robotic systems that prepare and execute the experiments to assemble the DNA sequences.

Embodiments of the present teachings provide systems and methods to simulate the design and performance characteristics resulting from inputs, processing steps and single outputs from the genetic circuit. In some embodiments, this may include the use simulate to illustrate how the genetic circuit and its parts may perform under the presence and absence of inputs. In some embodiments, this may include the use simulations to illustrate how the genetic circuit can perform and interact with the host cell.

Embodiments of the present invention provide systems and methods to design, provision for and provide experimental guidance for the functional analysis of the genetic circuit for the purposes of verifying and validating the genetic circuit design within the host cell. This may include the use of experimental tags, proteins and markers to identify modified DNAs, transcribed genes and translated proteins. In some embodiments, this may include instructions to run and perform such analyses upon robotic platforms.

Embodiments of the present teachings provide methods to identify, design and modify wild type DNA, RNA and protein sequences for the development of collections of characterized genetic circuit elements that can be reused in many future designs. In some embodiments the method comprises:

In some embodiments, the genetic circuit is deIdentifying a natural or synthetic biomolecule with desired functional characteristics Identifying Similar Molecules Through Comparative Analysis Employing tools to optimize the molecules for performance and expression. In some embodiments this will include optimizing the sequence for expression in a non native host. In some embodiments this will include use of computational tools to identify ways to modify add, remove, increase or reduce sequence changes with resultant functional significance for the expressed sequences. In some embodiments this will result in combination of functional domains from different wild type and synthetic molecules to create novel molecules with new functional behaviours.

Amplifying or synthesizing such molecules. In some embodiments these molecules will be designed to include modifications such as experimental tags or elements to facilitate future experimental identification and handling.

Combining such molecules with other genetic circuit elements to develop gene like elements termed devices. In some embodiments this will include the use of the software to assist with the design of such devices.

Combining such molecules to other genetic circuit elements or devices in order to create genetic circuits. In some embodiments this will include the use of the software to assist with the design of such genetic circuits.

Insertion of such molecules into standardized assays to evaluate their performance. In some embodiments data from the assays will be used to assess selection of genetic circuit elements as part of a design.

Reuse of such molecules in standardized assembly methodologies. In some embodiments this will include identification of host the elements will be optimized for. In some embodiments this will include experimental methodologies that the elements will be assembled with. In some embodiments this will include the experimental methodologies the elements will be verified and validated with.

Modification and Mutation of Standardized Molecules to Introduce New Functional Characteristics and Develop New Variants of these Molecules Embodiments of the present teachings provide methods for describing, classifying and characterizing the elements of a genetic circuit to aid in the design of genetic circuits. Genetic element data may be stored locally or in a server in a memory or database.

Genetic element data may be generated for describing the genetic circuit element, the classification of the element for its functional role and the characterization of the genetic element for its experimental performance. Genetic element data is a formalized description of the data necessary to describe a genetic element in a standardized format. In some embodiments, genetic element data can be used to share and distribute information about a genetic circuit element. In some embodiments genetic element data represent the data model for how a genetic circuit element can be used in design of a genetic circuit element. In some embodiments the genetic element data can be used to augment design of a genetic circuit element through use of classification terms. In some embodiments the genetic element data can be used to augment circuit design through use of experimental characterization data. In some embodiments the genetic element data will describe an assembly of genetic circuit elements into a functional unit, termed a device. In some embodiments the genetic element data will describe an assembly of devices into a genetic circuit.

Embodiments of the present teachings provide a means to standardize the classification of genetic circuit elements through use of defined terms. Some embodiments use a formalized grammar. Some embodiments use an ontology.

Embodiments of the present teachings provide a means to standardize the experimental characterization of a genetic circuit element through use of standardized assays and standardized reporting of measurements of performance from such assays. In some embodiments this may include the production of instructions for robots.

Embodiments described herein provide a means to develop biophysical models of genetic circuit elements, devices and genetic circuits. Such models can be used in scanning for existing functional characteristics of elements of a genetic circuit design. In some embodiments biophysical models can be used to design desired functional properties into genetic circuit elements, devices and genetic circuits. In some embodiments biophysical models can contribute to modeling and simulating the likely performance of these elements in a genetic circuit design. In some embodiments biophysical models can be used to evaluate the performance of genetic circuit elements, devices and genetic circuits in the target host system.

Embodiments of the described herein provide a means to standardize the design of a genetic circuit through the use of design rules. Such design rules embody the ways with which genetic circuit elements can be combined to form a device. Such design rules embody the ways with which devices can be combined to for a genetic circuit. Such design rules embody the ways with which genetic circuits sense inputs from the cell, process such inputs within the circuit and provide responses to the processing of the inputs. In some embodiments design rules can be achieved through use of optimization algorithms.

Embodiments of the present teachings provide a means to develop, classify and standardize the design of genetic circuits used to assay genetic design elements.

Embodiments of the present teachings provide a means to encode and characterize the experimental data resulting from assay measurements so that they can be included as part of the characterization data within a genetic element data. In some embodiments this may include single variable analysis measurements. In some embodiments this may include multiple variable analyses measurements. In some embodiments this may include results from analyses. In some embodiments this may include mathematical formulas or algorithms.

Embodiments of the present teachings provide a means to compare, sort, filter, exclude and otherwise select and manipulate parts based upon the information included in their genetic element data.

Embodiments of the present teachings provide a means to use developed genetic circuit elements, devices and circuits as template design templates. Design templates can be used as archetypal and reusable solutions for genetic circuits. Design templates are associated with assembled DNA molecules. Implementation of the design is realized through assembly of the corresponding DNA molecules. Reuse of the design templates is realized through reuse of the assembled DNA molecules in further experimental manipulations.

Embodiments of the present teachings provide a means to simulate design of devices and circuits in silico to identify to identify and discover designs that may detect desired inputs, process these detected inputs in a predictable manner and respond to the processing by producing a desired output. In some embodiments, this may include the identification, reduction and elimination of design issues between genetic circuit elements and devices; between genetic circuit elements, devices and circuits; between genetic circuit elements, devices and the target host. In some embodiments, this may include the ability to identify and remove, redesign or avoid issues that may result in non orthogonality between the different elements of the design. In some embodiments, the inputs may include molecules present in the cell, such as chemicals, metabolites, DNAs, RNAs, proteins, carbohydrates and lipids. In some embodiments, the inputs may include external queues that act upon the cell, such as cellular-cellular queues, environmental queues and chemical queues. In some embodiments the outputs may includes and interact with molecules present in the cell, such as chemicals, metabolites, DNAs, RNAs, proteins, carbohydrates and lipids. In some embodiments, the outputs may include and interact with external queues that act upon the cell, such as cellular-cellular queues, environmental queues and chemical queues.

Embodiments of the present teachings provide systems and methods to simulate the design, preparation for and execution of experiments to assemble DNA sequences corresponding to the designed genetic circuit elements, devices and circuits. In some embodiments, this may permit the comparison and combination of different assembly technologies to identify the most efficient path for assembly. In some embodiments, this may include the communication of such data to robotic systems that prepare and execute the experiments to assemble the DNA sequences.

Embodiments of the present teachings provide systems and methods to simulate the design and performance characteristics resulting from inputs, processing steps and single outputs from the genetic circuit. In some embodiments, this may include the use simulate to illustrate how the genetic circuit and its parts may perform under the presence and absence of inputs. In some embodiments, this may include the use simulations to illustrate how the genetic circuit can perform and interact with the host cell.

Embodiments of the present invention provide systems and methods to design, provision for and provide experimental guidance for the functional analysis of the genetic circuit for the purposes of verifying and validating the genetic circuit design within the host cell. This may include the use of experimental tags, proteins and markers to identify modified DNAs, transcribed genes and translated proteins. In some embodiments, this may include instructions to run and perform such analyses upon robotic platforms.

Embodiments of the present teachings provide methods and systems to publish, distribute, share and manage sets of genetic element data and genetic circuit designs among investigators. Sharing of data can be performed using novel or existing standardized publically described data formats.

Embodiments of the present teachings provide methods and systems to publish, distribute, share and manage sets of genetic element data and genetic circuit designs among investigators. Sharing of data can be performed using novel or existing standardized publically described data formats.

In some embodiments, the sequence-specific DNA binding polypeptides are selected from the group consisting of transcription factors, transcriptional activators, RNA polymerases, and transcriptional repressors. In some embodiments, the transcriptional repressor(s) are substantially identical to the Tetracycline repressor (TetR).

In some embodiments, the host cell is a prokaryotic cell. In some embodiments, the host cell is a eukaryotic cell.

In some embodiments, the method further comprises testing the circuit for unintended interactions within the circuit and/or between the circuit and the host cell genome.

In some embodiments, the providing comprises algorithm-guided identification of sequence-specific DNA binding polypeptides from one or more sequence database. In some embodiments, the algorithm identifies amino acid sequence similarity with a known sequence-specific DNA binding polypeptide. In some embodiments, a phylogenetic tree is used to maximize the diversity between sequence-specific DNA binding polypeptides in a library. In some embodiments, the algorithm identifies sequence-specific DNA binding polypeptide based on a phylogenetic tree. In some embodiments, the algorithm identifies sequence-specific DNA binding polypeptide based on their predicted ability to bind to different target DNA sequences. In some embodiments, the predicted ability is based on a bioinformatic algorithm that predicts the target DNA sequence by assuming that the sequence-specific DNA binding polypeptide is autoregulated.

In some embodiments, the optimizing comprises codon optimization of a gene encoding the polypeptide. In some embodiments, the optimizing comprises selecting random codons different from the native codons such that the coding sequence for the sequence-specific DNA binding polypeptide is different from the native coding sequence.

In some embodiments, the optimizing comprises using an algorithm to eliminate transcriptionally functional sequences in a gene encoding the polypeptide. In some embodiments, the functional sequences are ribosome binding sites, regulatory elements, or terminators. In some embodiments, the functional sequences are target DNA sequences for other sequence-specific DNA binding polypeptides in the orthogonal set.

In some embodiments, the target DNA sequences are determined by an in vitro method. In some embodiments, the in vitro method comprises contacting a set of sequence-specific DNA-binding polypeptides to an array of polynucleotides, thereby determining polynucleotide sequences bound by the DNA-binding polypeptides. In some embodiments, the array of polynucleotides is a microarray. In some embodiments, the polynucleotides to form a hairpin. In some embodiments, the hairpin comprises a target DNA sequence. In some embodiments, the hairpin comprises a 30 bp inverted repeat. In some embodiments, the inverted sequence has a T at position 14, A at position 13, A at position 7, T at position −7, T at position −13, and A at position −14. In some embodiments, the hairpin sequences are designed to have no more than a particular GC content. In some embodiments, the GC content of the hairpin is equal or less than 35%.

In some embodiments, the in vitro method is based on high-throughput sequencing to quantify RNA transcripts.

In some embodiments, the target DNA sequences are determined by an in vivo method. In some embodiments, the in vivo method comprises expression of the sequence-specific DNA binding polypeptide. In some embodiments, the in vivo method comprises constructing a synthetic regulatory element library, wherein regulatory elements in the library comprise one or more of the identified target DNA sequence(s). In some embodiments, the synthetic regulatory element library comprises mutations in the target DNA sequence binding region. In some embodiments, the target DNA sequence binding region is between −10 and −35 regions of the regulatory element. In some embodiments, the target DNA sequence is a −10 region or a −35 region. In some embodiments, the target DNA sequence is in a eukaryotic regulatory element. In some embodiments, the target DNA sequence in the eukaryotic regulatory element is identified in a yeast two-hybrid assay.

In some embodiments, the position of the target DNA sequence recruits RNA polymerase.

In some embodiments, the position of the target DNA sequence in the regulatory element is selected from: at the −10 or −35 region of the regulatory element, in the UP-region of the regulatory element, upstream of the −35 site, between the −10 and −35 sites. between the −10 and transcriptional start site, overlapping the transcriptional start site, and overlapping an activator binding site.

In some embodiments, the sequence-specific DNA-binding polypeptide comprises a modification that results in recruitment of RNA polymerase to DNA bound by the sequence-specific DNA-binding polypeptide. In some embodiments, the modification is the addition of the C-terminal VP16 sequence.

In some embodiments, the orthogonal set is determined by identifying a set of sequence-specific DNA-binding polypeptides that do not bind to each other's target DNA sequences. In some embodiments, the designing cognate sequence-specific DNA binding polypeptide-target DNA sequence pairs comprises maximizing the size of the set of orthogonal sequence-specific DNA binding polypeptide-target DNA sequence pairs. In some embodiments, the identifying comprises using a bioinformatic model built using empirical DNA binding data. In some embodiments, the bioinformatic model maximizes the diversity between target DNA sequences in the set of orthogonal sequence-specific DNA binding polypeptide-target sequence pairs. In some embodiments, a graph partitioning algorithm is used to identify the maximum orthogonal set. In some embodiments, edges of the set are weighted by sequence entropy calculated by the set of DNA binding sequences to which two target DNA sequences bind.

In some embodiments, the repressors are TetR homologues, zinc finger proteins, or Tal effectors. In some embodiments, the TetR homologues are AcrR, AmtR, ArpA, BM3R1, BarA, BetI, EthR, FarA, HapR, HlyIIR, IcaR, LmrA, LuxT, McbR, MphR, MtrR, MtrR, PhlF, PsrA, QacR, ScbR, SmcR, SmeT, TetR, TtgR, TylP, UidR, VarR.

In some embodiments, the transcriptional activators are sigma factors.

In some embodiments, the genetic circuit is determined using a logic minimization algorithm. In some embodiments, the logic minimization algorithm is ESPRESSO.

In some embodiments, the genetic circuit is defined using a hardware descriptive language. In some embodiments, the hardware descriptive language is VHDL or Verilog.

In some embodiments, the genetic circuit is a combination of logic gates. In some embodiments, the logic gates are selected from the group consisting of AND, NAND, NOR, OR, NOT, XOR, EQUALS, AND, IMPLIES, and ANDN gates. In some embodiments, the NOR gates comprise a transcriptional repressors and a transcriptional repressor target DNA sequence. In some embodiments, the AND gates comprises a sigma factor and a sigma factor target DNA sequence. In some embodiments, the sigma factor is a chimeric sigma factor comprising a first and second domain wherein the first and second domains are from two different sigma factors, wherein the first domain binds to a −10 region of a regulatory element and the second domain binds to a −35 region of a regulatory element.

In some embodiments, the RNA polymerase is substantially identical to T7 RNA polymerase (RNAP). In some embodiments, the set of orthogonal pairs comprises at least two or more different RNA polymerases substantially identical to T7 RNA polymerase (RNAP). In some embodiments, the T7 RNAP has been modified from its native form to reduce toxicity to a heterologous organism. In some embodiments, the modification includes one or more of addition of an N-terminal Lon protease tag, a GTG start codon, and/or an R632S mutation.

In some embodiments, the method further comprises mutating T7 RNAP to generate an orthogonal set of polypeptides substantially identical to T7 RNAP that bind to different DNA sequences. In some embodiments, the polypeptides comprise a loop corresponding to the loop between 745 and 761 of T7 RNAP, wherein the loop is mutated to the sequence of a homologous phage polymerase.

In some embodiments, the RNA polymerase is from T3, K1F, or N4.

In some embodiments, a cognate target DNA sequence is created by mutating at least one nucleotide of a T7 RNAP dependent promoter between nucleotides −13 and −18

In some embodiments, a cognate target DNA sequence comprises a DNA binding sequence for T3, K1F, or N4 phage polymerase.

In some embodiments, strength of the cognate target DNA sequence has been modified by mutating the nucleotides between −4 and −8.

In some embodiments, the method comprises generating a library of promoters with different strengths by recombining defined sequences between −13 and −18 with defined sequences between −4 and −8 of a DNA binding sequence for T7, T3, K1F, or N4 phage polymerase.

In some embodiments, the transcriptional activator requires a second chaperone polypeptide to be bound to the activator to generate transcriptional activity. In some embodiments, the transcriptional activator is substantially identical to InvF (from *Salmonella typhimurium*), MxiE (from *Shigella flexneri*), or ExsA (from *Pseudomonas aeruginosa*). In some embodiments, the chaperone is substantially similar to SicA (from *Salmonella typhimurium*), IpgC (from *Shigella flexneri*), or ExsC (from *Pseudomonas aeruginosa*)

In some embodiments, the transcriptional activator and chaperone are used to construct an AND gate. In some embodiments, one promoter serves as an input controls the expression of the activator and a second promoter that serves as an input controls the expression of the chaperone.

Embodiments of the invention also provide methods of generating a library of orthogonal sigma factors, transcriptional repressor, and/or RNA polymerases. In some embodiments, the method comprises generating a library of polynucleotides encoding chimeric sigma factors, wherein the chimeric sigma factors comprise a domain from at least two different sigma factors, wherein each of the domains bind to the −10 or −35 region of a regulatory element; and expressing chimeric sigma factors from the library of polynucleotides, thereby generating a library of chimeric sigma factors.

Embodiments of the invention also provide for a host cell comprising a heterologous genetic circuit comprising at least two orthogonal sequence-specific DNA binding polypeptides, wherein the genetic circuit is a combination of logic gates. In some embodiments, the logic gates are selected from the group consisting of AND, NAND, NOR, OR, NOT, XOR, EQUALS, AND, IMPLIES, and ANDN gates. In some embodiments, the NOR gates comprise a transcriptional repressors and a transcriptional repressor target DNA sequence. In some embodiments, the AND gates comprises a sigma factor and a sigma factor target DNA sequence. In some embodiments, the sigma factor is a chimeric sigma factor comprising a first and second domain wherein the first and second domains are from two different sigma factors, wherein the first domain binds to a −10 region of a regulatory element and the second domain binds to a −35 region of a regulatory element.

In some embodiments, the at least two sequence-specific DNA binding polypeptides are selected from the group consisting of transcription factors, transcriptional activators, RNA polymerases, and transcriptional repressors.

In some embodiments, the at least two sequence-specific DNA binding polypeptides are transcriptional activators.

In some embodiments, the at least two sequence-specific DNA binding polypeptides are RNA polymerases.

In some embodiments, wherein the at least two sequence-specific DNA binding polypeptides are transcriptional repressors.

In some embodiments, the logic gates comprise a regulatory element, wherein the regulatory element comprises a target DNA sequence bound by one of the sequence-specific DNA binding polypeptides and wherein the position of the target DNA sequence in the regulatory element is selected from: at the −10 or −35 region of the regulatory element, in the UP-region of the regulatory element, upstream of the −35 site, between the −10 and −35 sites. between the −10 and transcriptional start site, overlapping the transcriptional start site, and overlapping an activator binding site. In some embodiments, the at least two sequence-specific DNA binding polypeptides are selected from the group consisting of transcription factors, transcriptional activators, RNA polymerases, and transcriptional repressors.

In some embodiments, the host cell is a prokaryotic host cell. In some embodiments, the gates are combined by having the output promoter of an upstream gate serve as the input promoter of a downstream gate. In some embodiments, a spacer sequence is included after the promoter that serves as a connection point between gates. In some embodiments, the spacer is encoded at the 5'-UTR of the mRNA encoding a transcription factor before the ribosome binding site. In some embodiments, the spacer forms a stem loop, is a native sequence from a metabolic pathway, or is from a 5'-UTR obtained from a phage. In some embodiments, the stem loop is a ribozyme. In some embodiments, the ribozyme is RiboJ.

Embodiments of the invention also provide a computer readable medium encoded with instructions, executable for a process, for designing a host cell comprising a heterologous genetic circuit comprising at least two orthogonal sequence-specific DNA binding polypeptides, wherein the genetic circuit is a combination of logic gates, the instructions comprising instructions for:
providing a set of sequence-specific DNA binding polypeptides;
optimizing expression of the polypeptides in a heterologous host cell;
identifying target DNA sequences to which the polypeptides bind;
generating synthetic transcriptional regulatory elements comprising at least one identified target DNA sequence, wherein the regulatory elements are responsive to a sequence-specific DNA binding polypeptide from the set of sequence-specific DNA binding polypeptides;
designing cognate sequence-specific DNA binding polypeptide-target DNA sequence pairs to generate one or more orthogonal sequence-specific DNA binding polypeptide-target DNA sequence pairs;
designing a genetic circuit comprising a combination of logic gates, the logic gates comprising the one or more orthogonal sequence-specific DNA binding polypeptide-target DNA sequence pairs.

Embodiments of the invention also provide a computer product comprising a computer readable medium encoded with a plurality of instructions for controlling a computing system to perform an operation for designing a host cell comprising a heterologous genetic circuit comprising at least two orthogonal sequence-specific DNA binding polypeptides, wherein the genetic circuit is a combination of logic gates, the instructions comprising instructions for the steps of any of the methods described above or elsewhere herein.

Definitions

"Genetic circuits" are comprised of a set of heterologous expression cassettes whose (generally protein) products regulate other expression cassettes in the set and/or regulate an ultimate output of the circuit. Genetic circuit components can be used to implement any arbitrary Boolean operation in living cells based on an input detected by the circuit. Individual components for particular operations can be coupled to inputs and to one another in order to implement a genetic circuit that operates on a complex expression. Genetic circuits may process a Boolean expression that connect logic variables representing the cues via logic operations (e.g., AND, NAND, NOR, OR, NOT, XOR, EQUALS, AND, IMPLIES, and ANDN gates).

A "set" refers to a group of two or more items. Generally, the items will have a similar effect or action (e.g., a set of activators, a set of repressors, etc.).

"Optimizing expression" of a polypeptide, as used herein, refers to altering the nucleotide sequences of a coding sequence for a polypeptide to refine or alter the expression of the polypeptide (e.g., by altering transcription of an RNA encoding the polypeptide) to achieve a desired result. The desired result can be optimal expression, but can also be simply obtaining sufficient expression in a heterologous host cell to test activity (e.g., DNA sequence binding) of the polypeptide. "Optimizing" can also include altering the nucleotide sequence of the gene to alter or eliminate native transcriptional regulatory sequences in the gene, thereby eliminating possible regulation of expression of the gene in the heterologous host cell by the native transcriptional regulatory sequence(s). Optimization can include replacement of codons in the gene with other codons encoding the same amino acid. The replacement codons can be those that result in optimized codon usage for the host cell, or can be random codons encoding the same amino acid, but not necessarily selected for the most "preferred" codon in a particular host cell.

"Heterologous," in reference to a relationship between a cell and a polynucleotide means the polynucleotide originates from a foreign species, or, if from the same species, is modified from its original (native) form.

"Target DNA sequences" refer to DNA sequences bound by sequence-specific DNA binding polypeptides. For example, an operator for a transcriptional activator or repressor is a target DNA sequence.

"Transcriptional regulatory elements" refer to any nucleotide sequence that influences transcription initiation and rate, or stability and/or mobility of a transcript product. Regulatory sequences include, but are not limited to, promoters, promoter control elements, protein binding sequences, 5' and 3' UTRs, transcriptional start sites, termination sequences, polyadenylation sequences, introns, etc. Such transcriptional regulatory sequences can be located either 5'-, 3'-, or within the coding region of the gene and can be either promote (positive regulatory element) or repress (negative regulatory element) gene transcription.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "cognate pair" as used herein refers to a sequence-specific DNA binding polypeptide and a target DNA sequence that is bound by the particular sequence-specific DNA binding polypeptide. For sequence-specific DNA binding polypeptides that bind more than one target nucleic acid, the cognate pair can be formed with the sequence-specific DNA binding polypeptide and any one of the target DNA sequences the polypeptide binds.

"Orthogonal" transcriptional systems refer to systems (e.g., one, two, three, or more) of transcriptional regulatory elements comprising target DNA sequences regulated by their cognate sequence-specific DNA binding polypeptide such that the sequence-specific DNA binding polypeptides in the system do not have "cross-talk," i.e., the sequence-specific DNA binding polypeptides do not interfere or regulate transcriptional regulatory elements in the system other than the transcriptional regulatory elements containing the cognate target DNA sequence of the sequence-specific DNA binding polypeptide.

"Sequence-specific DNA binding polypeptides" refer to polypeptides that bind DNA in a nucleotide sequence specific manner. Exemplary sequence-specific DNA binding polypeptides include, but are not limited to transcription factors (e.g., transcriptional activators), RNA polymerases, and transcriptional repressors.

A "transcriptional activator" refers to a polypeptide, which when bound to a promoter sequence, activates or increases transcription of an RNA comprising the operably-linked coding sequence. In some embodiments, the transcriptional activator bound to a target sequence in a promoter can assist recruitment of RNA polymerase to the promoter. A "transcriptional repressor" refers to a polypeptide, which when bound to a promoter sequence, blocks or decreases transcription of an RNA comprising the operably-linked coding sequence. In some embodiments, the transcriptional repressor blocks recruitment of the RNA polymerase to the promoter or blocks the RNA polymerase's movement along the promoter.

The "−10" and "−35" regions of a promoter refer to regions in prokaryotic promoters, as measured from the transcriptional start site. The −10 region is sometimes also known as a "Pribnow box" in the scientific literature. The −10 region is typically six nucleotides long. In some embodiments, the −10 region has the sequence "TATAAT" or a variant thereof. The −35 region" is a sequence that can range from 8-12 nucleotides. One variant of the −35 region is "TGTTGACA." However, as noted before, the −10 and −35 regions can have various sequences.

The term "host cell" refers to any cell capable of replicating and/or transcribing and/or translating a heterologous gene. Thus, a "host cell" refers to any prokaryotic cell (including but not limited to E. coli) or eukaryotic cell (including but not limited to yeast cells, mammalian cells, avian cells, amphibian cells, plant cells, fish cells, and insect cells), whether located in vitro or in vivo. For example, host cells may be located in a transgenic animal or transgenic plant. prokaryotic cell (including but not limited to E. coli) or eukaryotic cells (including but not limited to yeast cells, mammalian cells, avian cells, amphibian cells, plant cells, fish cells, and insect cells).

Two nucleic acid sequences or polypeptides are said to be "identical" if the sequence of nucleotides or amino acid residues, respectively, in the two sequences is the same when aligned for maximum correspondence as described below. The term "substantial identity," in reference to nucleotide or amino acid sequences, means that a nucleotide or amino acid sequence, respectively, comprises a sequence that has at least 50% sequence identity. Alternatively, percent identity can be any integer from 50% to 100%, e.g., at least: 50%, 55%, 60%, 65%, 70%, 75%, 80%, 85%, 90%, 95%, or 99% compared to a reference sequence using the programs described herein; preferably BLAST using standard parameters, as described below. One of skill will recognize that the percent identity values above can be appropriately adjusted to determine corresponding identity of proteins encoded by two nucleotide sequences by taking into account codon degeneracy, amino acid similarity, reading frame positioning and the like. In some embodiments, polypeptides that are "substantially similar" share sequences as noted above except that residue positions which are not identical may differ by conservative amino acid changes. Conservative amino acid substitutions refer to the interchangeability of residues having similar side chains.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

One example of algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

BRIEF DESCRIPTION OF THE DRAWINGS

FIG. 3 (left side) shows typical growth rate plots. FIG. 3 (right side) shows average growth rate as % of wild type (non-ECF σ expressing) cells during exponential growth.

FIG. 9 shows that ECF sigmas contain 2 DNA binding domains. ECF sigmas (Left) contain 2 conserved DNA binding domains, R2 and R4, that contact the promoter -10 and -35 regions, respectively. Promoter logos of 2 candidate ECF sigmas are shown (right) that recognize different -10 and -35 sequences (SEQ ID NOS:30 and 31).

FIG. 10 illustrates chimeric sigmas. 2 chimeric sigmas were made by domain swapping R2 and R4 from ECF02_2817 and ECF11_3726. Each chimeric sigma was constructed with a cognate chimeric promoter, P02_11 for chimera ECF02_ECF11, and P11_02 for chimera ECF11_ECF02.

FIG. 15 shows raw flow cytometry data of the AmtR reporter screened against the repressor library, thus demonstrating that only AmtR exhibits high levels of repression from this reporter. Each cell corresponds to a different repressor, and the AmtR repressor is present in the yellowed-cell.

FIG. 17 illustrates the relative toxicity of T7 RNAP scaffolds (SEQ ID NOS:39-44).

FIG. 18 illustrates the promoter strength of mutant T7 promoters (SEQ ID NOS:47-52). Promoter sequence motif=SEQ ID NO:45; wild-type (WT) promoter=SEQ ID NO:46.

FIG. 19 shows the termination strength of mutant transcriptional terminators (SEQ ID NOS:54-59 and 61-64).

Terminator sequence motif=SEQ ID NO:53; wild-type (WT) terminator=SEQ ID NO:60.

FIGS. 20A-20B illustrate orthogonal RNAP:promoter combinations (SEQ ID NOS:65, 46 AND 66-71). FIG. 20A shows the phage genome based specificity loops.

FIG. 20B shows the orthogonality of the RNAP:promoter combinations.

FIG. 21 shows that T7 (SEQ ID NOS:73-78) and T3 (SEQ ID NOS:79-84) RNAPs are orthogonal to combinatorial promoters with phage-specific recognition domains. Partial promoter sequence=SEQ ID NO:72.

Figure 22:
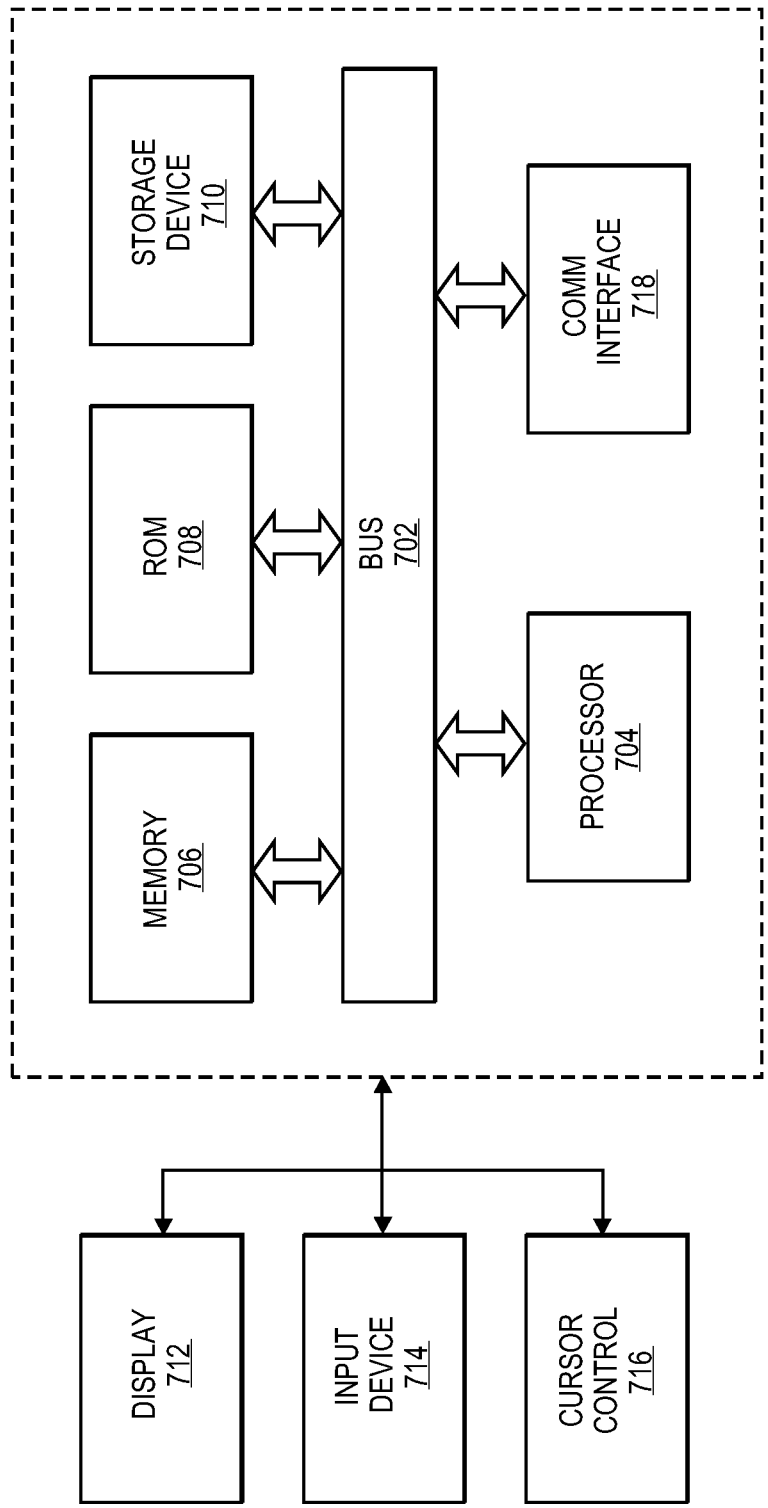

FIG. 22 illustrates a block diagram that illustrates components of an exemplary computing system that may be utilized according to various embodiments described herein.

FIG. 23 illustrates a schematic for various repressor construct design. Also illustrated are graphs showing variation between promoters in the absence of a heterologous spacer 5' UTR sequence.

FIG. 24 illustrates a schematic for a construct used to screen for 5' UTR spacers as well as a graphical representation of the results from a number of spacers.

Figure 25:
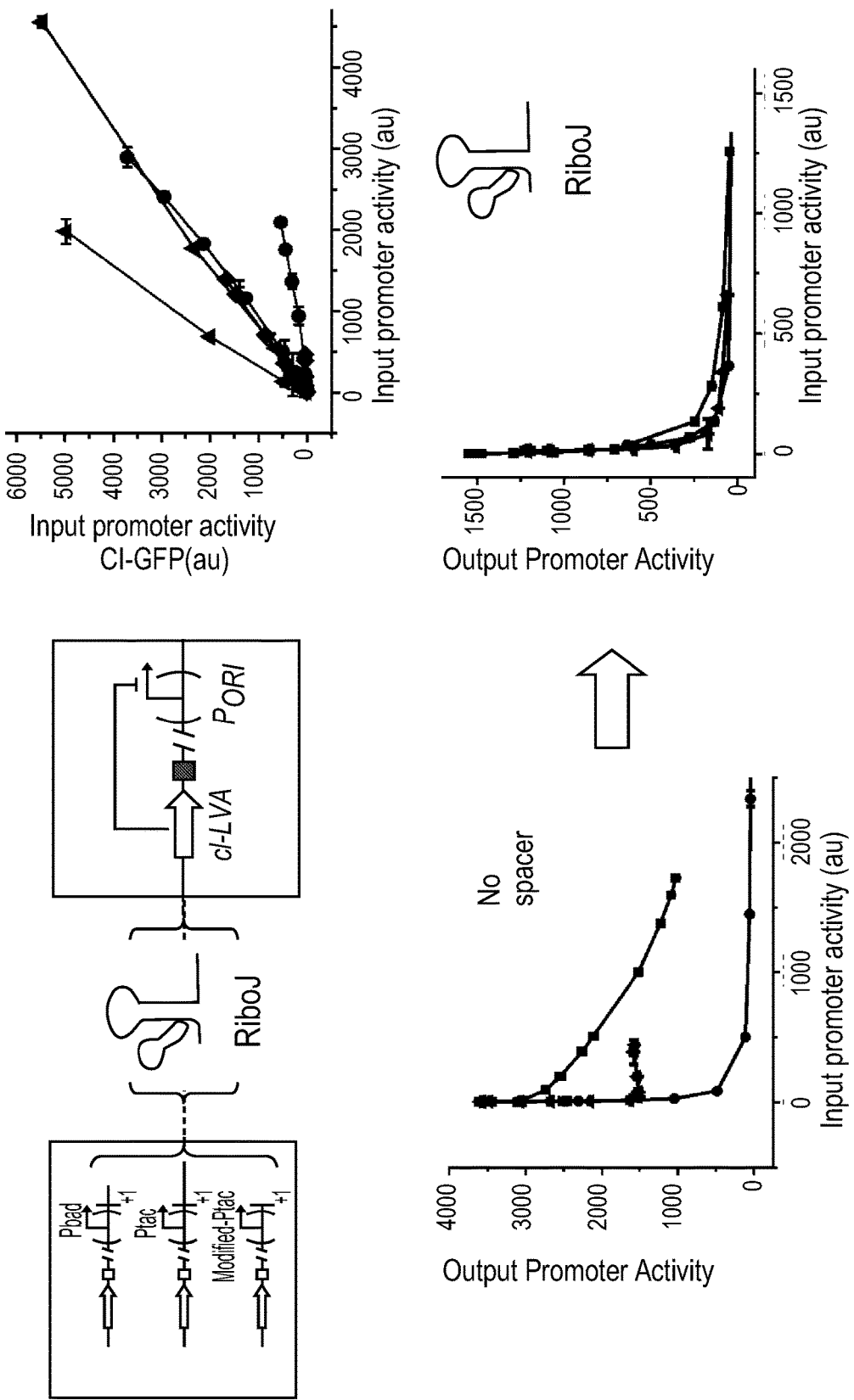

FIG. 25 illustrates a schematic representation of a construct containing the riboJ 5' UTR spacer and graphically shows how the RiboJ spacer results in repeatable results for different promoters.

Figure 26:
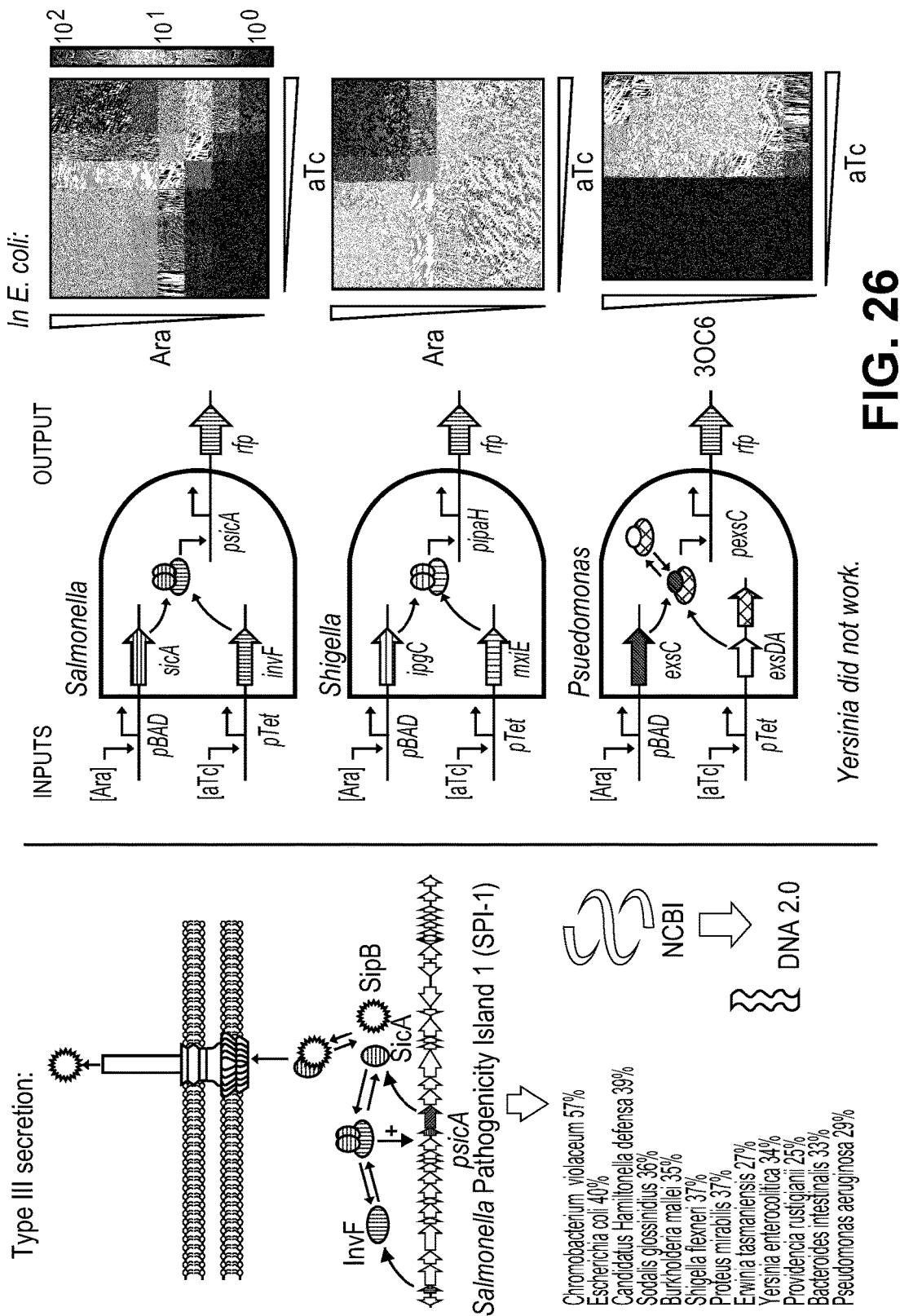

FIG. 26 shoes three AND gate designs.

Figure 27:
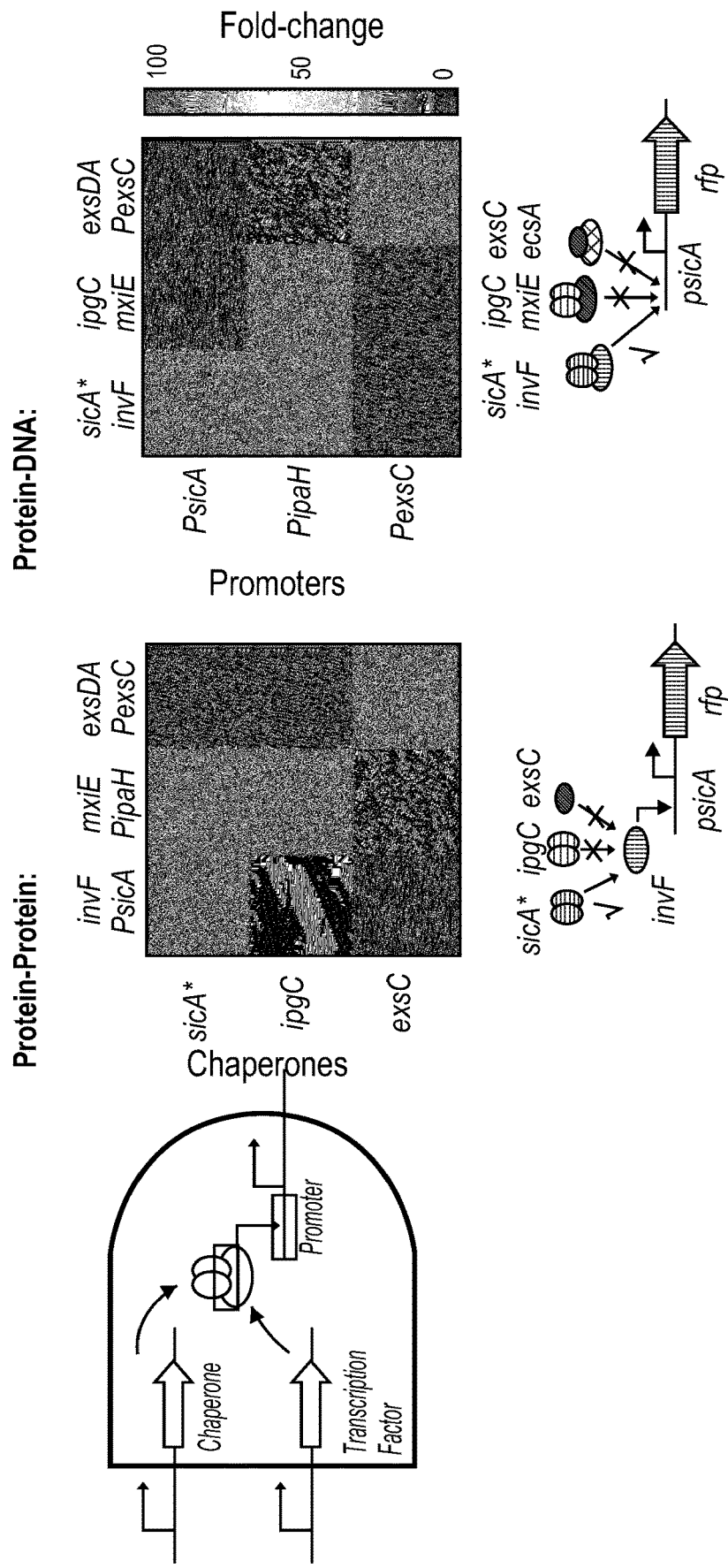

FIG. 27 shows the orthogonality of various gates.

Figure 28:
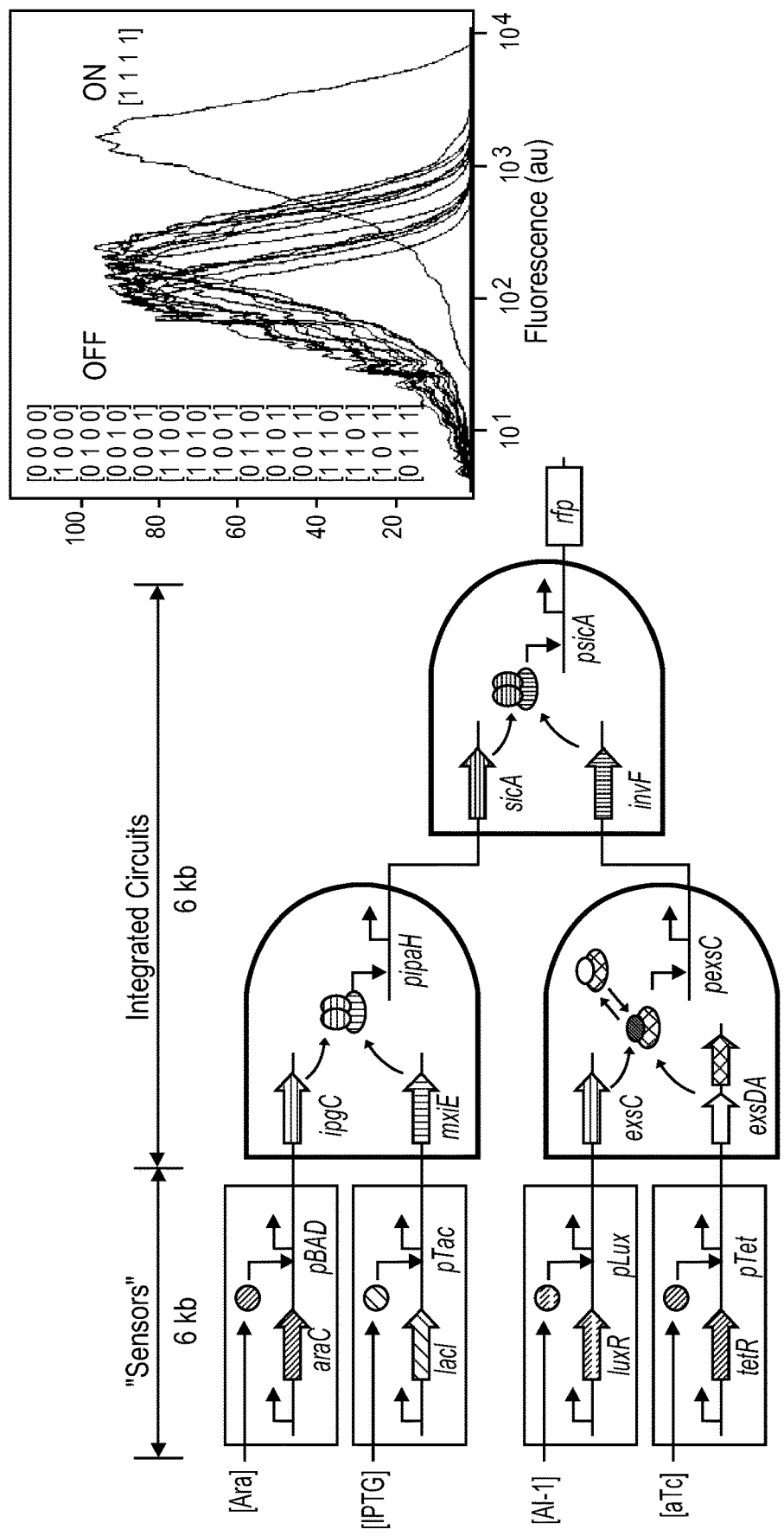

FIG. 28 shows a 4-input AND gate design.

Figure 29:
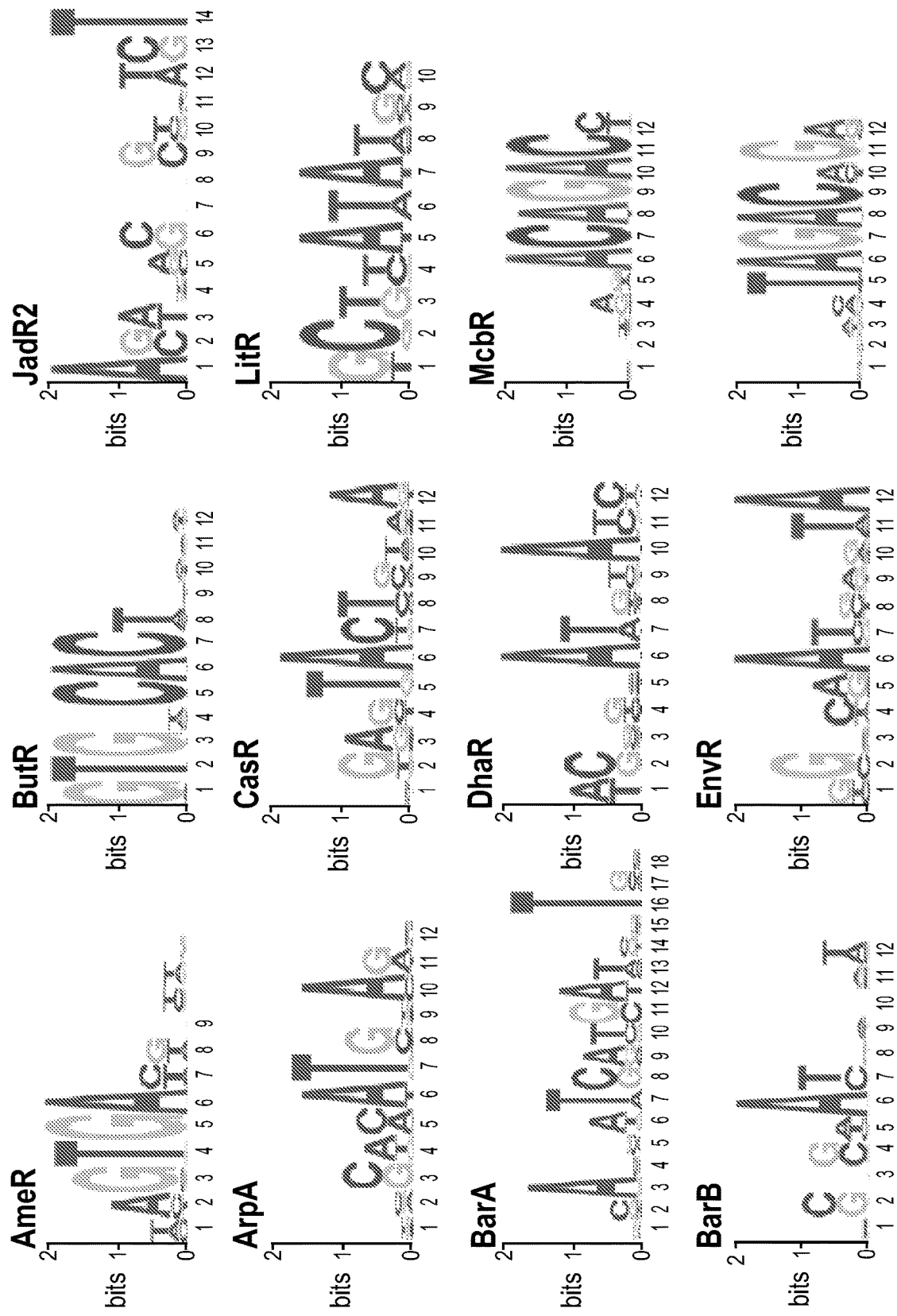

FIG. 29 illustrates consensus sequences for the AmeR, ArpA, BarA, BarB, ButR, CasR, DhaR, EnvR, and McbR (SEQ ID NOS:85, 38 and 86-95).

FIG. 30 illustrates design of a RBS library (SEQ ID NO:96) to select for those constructs exhibiting a high 'ON' state and a low 'OFF' state. Exemplary results are shown on the right.

Figure 31:
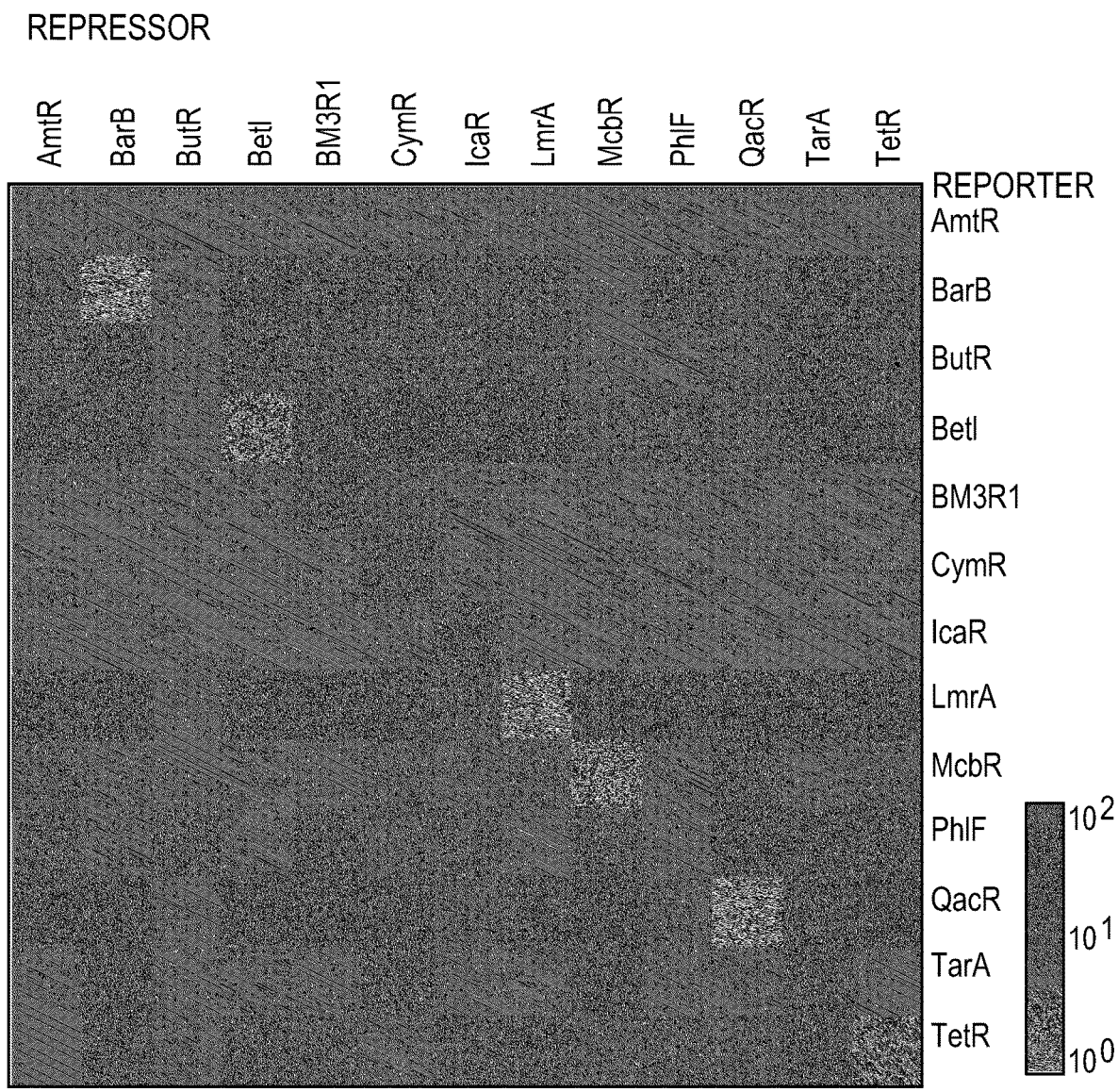

FIG. 31 illustrates a heat map showing that AmtR, BarB, BetI, ButR, BM3R1, CymR, IcaR, LmrA, McbR, PhlF, QacR, TarA, and TetR repressors were orthogonal; high-levels of repression are observed only in the presence of the properly matched repressor.

DETAILED DESCRIPTION

I. Introduction

Engineering synthetic gene circuits requires a library of "parts" that serve to regulate gene expression and can be reliably combined together to build complex programs. Transcriptional regulatory elements (e.g. promoters) are a "part" that control gene expression by regulating the rate of mRNA production. Large genetic circuits can require many promoters that can be individually controlled. This enables conditional control of gene expression across a circuit. A library of orthogonal promoter systems in which regulators target specific promoters with no cross-talk across the circuit is thus useful in design of genetic circuits.

Methods of generating a "toolbox" of genetic components and for subsequent design of genetic circuits are provided. Orthogonal components for use in a genetic circuit can be identified by providing a set of sequence-specific DNA binding polypeptides, identifying their target DNA sequences (i.e., the DNA sequences that the polypeptides bind), and designing a set of orthogonal sequence-specific DNA binding polypeptide-target DNA sequence cognate pairs. Generation of the set of orthogonal sequence-specific DNA binding polypeptide-target DNA sequence cognate pairs provides a "toolbox" from which genetic circuits can then be made by using the cognate pairs to generate a system of Boolean logic gates as desired.

In some embodiments, the methods comprise:

Providing a set of sequence-specific DNA binding polypeptides;

Optimizing expression of the polypeptides in a heterologous host cell (e.g., the host cell species in which the genetic circuit will eventually be employed);

Identifying the full complement of target DNA sequences bound by at least a subset of the sequence-specific DNA binding polypeptides; and Designing a set of orthogonal sequence-specific DNA binding polypeptide-target DNA sequence cognate pairs (i.e. a set in which each pair regulates only itself and not other members of the set).

Subsequently, the cognate pairs can be selected for use in a genetic circuit. Because the cognate pairs are part of the orthogonal set, the cognate pairs can be used in combinations (e.g., 2, 3, 4, 5, 6, 7, 8, 9, or more cognate pairs) from the orthogonal set without interference from each other. Once designed, the genetic circuit can be deployed in a host cell and further tested for unintended interactions within the circuit and/or with the host cell transcriptional regulatory system.

II. Sequence-Specific DNA Binding Polypeptides

Several classes of sequence-specific DNA binding polypeptides have been described in detail here to exemplify sequence-specific DNA binding polypeptides. However, it should be appreciated that similar technical approaches can be used to design other classes of sequence-specific DNA binding polypeptides for use in the methods described herein.

Sets of sequence-specific DNA binding polypeptides, i.e., a plurality of different sequence-specific DNA binding polypeptides, optionally having sequence similarity or otherwise being of the same class of regulatory factor, can be generated as desired. In some embodiments, one or more pre-selected (e.g., by a third party) set of sequence-specific DNA binding polypeptides is provided. Alternatively, or in combination, in some embodiments, sequence-specific DNA binding polypeptides can be identified from one or more sequence database (e.g., NCBI, etc.). A variety of algorithms are available for identification of sequence-specific DNA binding polypeptides. For example, sequence similarity algorithms (e.g., BLAST and the like) can be used to identify amino acid sequence similarity in a database to a known sequence-specific DNA binding polypeptide. In some embodiments, for example, the algorithm identifies sequence-specific DNA binding polypeptide based on a phylogenetic tree.

Generation of the set of sequence-specific DNA binding polypeptides can include increasing, and in some cases, maximizing the diversity within the set. Said another way, given a finite and possibly limited number of members of a set, the members can be selected to be as different from each other as possible. For example, in some embodiments, a phylogenetic tree is used to maximize diversity between sequence-specific DNA binding polypeptides in a library. In some embodiments, the algorithm identifies sequence-specific DNA binding polypeptide based on their predicted ability to bind to different target DNA sequences.

In some embodiments, the algorithm can predict the ability of a sequence-specific DNA binding polypeptide to bind to different target DNA sequences if expression of the gene encoding the sequence-specific DNA binding polypeptide is autoregulated. For example, most ECF sigmas are autoregulated; i.e. the gene encoding the sigma is regulated by a promoter recognized by the same ECF sigma. ECF sigma factors in the same ECF subgroup recognize the same promoter sequence, since their DNA binding sequences are highly conserved within each group. Consequently, promoters can be identified for each subgroup by searching the upstream regulatory regions for conserved motifs. In one example, the following steps can be performed wholly or partially by a computer system to determine target sequence motifs of autoregulated DNA-binding polypeptides that bind to 2-block motifs:

1) For each subgroup of a sequence-specific DNA binding polypeptide (i.e., a subgroup for which it is expected all members bind the same conserved target DNA sequence), one can generate a set of upstream regulatory sequences by extracting the DNA sequences upstream of each gene encoding the DNA binding polypeptides (for example, 100, 200, 300, 400, 500, 1000 nt or more upstream of the gene to the gene start) based on the bacterial genomic sequences archived in a database (e.g., NCBI). The generated sequence sets can be stored in memory for subsequent retrieval (e.g., in a database with labels identifying sequences of a respective sequence set).

2) Search each sequence set for conserved over-represented motifs. For example, a process of the computer system can use an algorithm to search the database of sequence sets. An exemplary algorithm is a 2-block motif finding algorithm (including but not limited to BioProspector (Liu et al 2001: Liu X, Brutlag D L, Liu J S. *Pac Symp Biocomput*. 2001; 127-38)). This search allows one to search for two conserved sequence blocks separated by a variable length non-conserved spacer region. An exemplary search parameter representing the structure of ECF promoters would be: <block 1><spacer><block 2>, where block 1 is 7 nt in length, block 2 is 5 nt in length, and the spacer length varies from 13-15 nt.

3) For each sequence set, the highest scoring 2-block motif is selected by the processor to represent the target sequence motifs for that sequence-specific DNA binding polypeptide subgroup. Because the motif sizes can vary slightly between different sequence-specific DNA binding polypeptide subgroups, in some embodiments, optimal motifs are identified by performing multiple searches with slightly different <block 1><spacer><block 2> parameters.

4) For each sequence-specific DNA binding polypeptide subgroup: A sequence model can be constructed by the processor based on the highest scoring 2-block model. An exemplary model for ECF sigma promoters would be where block 1 represents the promoter −35 region; block 2 represents the promoter −10 region; the variable spacer length is used to construct a histogram of spacer lengths.

5) The sequence model can then be used by the processor to generate a Position Weight Matrix (PWM)-based scoring model to identify and score new sequences. An exemplary scoring model for ECF sigma promoters would be separate PWMs constructed based on the aligned −35 and −10 motifs and a spacer penalty termed for suboptimal spacer lengths based on the spacer histograms.

The above steps can be varied or adapted as necessary for the particular type of sequence-specific DNA binding polypeptide examined.

In addition to use of native or randomly mutated sequence-specific DNA binding polypeptides, it should also be appreciated that the sequence-specific DNA binding polypeptide can be modified to increase recruitment of RNA polymerase to DNA bound by the sequence-specific DNA-binding polypeptide. As an example, one can modify the sequence-specific DNA binding polypeptides by addition of a transcription factor domain known to recruit RNA polymerase. For example, the C-terminal amino acid sequence of the VP16 transcription factor can be linked to the sequence-specific DNA binding polypeptide.

A. Transcriptional Activators i. General

As noted above, it is believed that any class of transcriptional activators can be adapted for use in the methods described herein.

ii. Sigma Factors

In some embodiments, the sequence-specific DNA binding polypeptide is a sigma (σ) factor. Sigma factors recruit RNA polymerase (RNAP) to specific promoter sequences to initiate transcription. The σ 70 family consist of 4 groups: Group 1 are the housekeeping σs and are essential; groups 2-4 are alternative σs that direct cellular transcription for specialized needs (Gruber and Gross 2003). Group 4 σs (also known as ECF σs; extracytoplasmic function) constitute the largest and most diverse group of σs, and have been classified into 43 subgroups (Staron et al., *Mol Microbiol* 74(3): 557-81 (2009)). The subgroups can be stored in memory (e.g. a database) of a computer system.

In some embodiments, the set of sequence-specific DNA-binding polypeptides comprise multiple sigma factors. In some embodiments, the set comprises sigma factors from Group 1, Group 2, Group 3, and/or Group 4 Sigma factors. The ECF subgroup of Group 4 is thought to recognize different promoter sequences, making these σs particularly useful for constructing orthogonal σ-promoter systems. However, it will be appreciated that any group of sigma factors can be used according to the methods of the embodiments of the invention to develop cognate pairs. In some embodiments, one (e.g., 1, 2, 3, 4, 5, 6, 7, 8, 9, etc.) or more sigma factor from Table 1 (or substantially identical to a sigma factor in Table 1) is selected for use in an orthogonal set of cognate pairs and/or in a genetic circuit.

TABLE 1

| Group Nr[a] | ID[b] | GI[c] | SPECIES[d] | CLASS[d] | PHYLUM[d] |
|---|---|---|---|---|---|
| ECF01 | >3473 | 109899616 | *Pseudoalteromonas atlantica* T6c | Gammaproteobacteria | Proteobacteria |
| ECF01 | >4085 | 114562024 | *Shewanella frigidimarina* NCIMB 400 | Gammaproteobacteria | Proteobacteria |
| ECF02 | >2817 | 16130498 | *Escherichia coli* K12 | Gammaproteobacteria | Proteobacteria |
| ECF02 | >915 | 119774011 | *Shewanella amazonensis* SB2B | Gammaproteobacteria | Proteobacteria |
| ECF03 | >1198 | 29350055 | *Bacteroides thetaiotaomicron* VPI-5482 | | Bacteroidetes |
| ECF03 | >1244 | 34541012 | *Porphyromonas gingivalis* W83 | | Bacteroidetes |
| ECF04 | >1609 | 21673117 | *Chlorobium tepidum* TLS | | Chlorobi |
| ECF04 | >1617 | 68549683 | *Pelodictyon phaeoclathratiforme* BU-1 | | Chlorobi |
| ECF05 | >965 | 28868416 | *Pseudomonas syringae* pv. tomato str. DC3000 | Gammaproteobacteria | Proteobacteria |
| ECF05 | >1054 | 67154316 | *Azotobacter vinelandii* AvOP | Gammaproteobacteria | Proteobacteria |
| ECF06 | >3576 | 15595669 | *Pseudomonas aeruginosa* PAO1 | Gammaproteobacteria | Proteobacteria |
| ECF06 | >853 | 26987094 | *Pseudomonas putida* KT2440 | Gammaproteobacteria | Proteobacteria |
| ECF07 | >980 | 67154823 | *Azotobacter vinelandii* AvOP | Gammaproteobacteria | Proteobacteria |

TABLE 1-continued

| Group Nr[a] | ID[b] | GI[c] | SPECIES[d] | CLASS[d] | PHYLUM[d] |
|---|---|---|---|---|---|
| ECF07 | >1134 | 15598606 | *Pseudomonas aeruginosa* PAO1 | Gammaproteobacteria | Proteobacteria |
| ECF08 | >3580 | 15595872 | *Pseudomonas aeruginosa* PAO1 | Gammaproteobacteria | Proteobacteria |
| ECF08 | >3627 | 70730114 | *Pseudomonas fluorescens* Pf-5 | Gammaproteobacteria | Proteobacteria |
| ECF09 | >3581 | 15597622 | *Pseudomonas aeruginosa* PAO1 | Gammaproteobacteria | Proteobacteria |
| ECF09 | >1009 | 70730971 | *Pseudomonas fluorescens* Pf-5 | Gammaproteobacteria | Proteobacteria |
| ECF10 | >3486 | 77360766 | *Pseudoalteromonas haloplanktis* TAC125 | Gammaproteobacteria | Proteobacteria |
| ECF10 | >2914 | 88706154 | gamma proteobacterium KT 71 | Gammaproteobacteria | Proteobacteria |
| ECF11 | >3726 | 28868260 | *Pseudomonas syringae* pv. tomato str. DC3000 | Gammaproteobacteria | Proteobacteria |
| ECF11 | >987 | 28899132 | *Vibrio parahaemolyticus* RIMD 2210633 | Gammaproteobacteria | Proteobacteria |
| ECF12 | >807 | 86158800 | *Anaeromyxobacter dehalogenans* 2CP-C | Deltaproteobacteria | Proteobacteria |
| ECF12 | >808 | 108762328 | *Myxococcus xanthus* DK 1622 | Deltaproteobacteria | Proteobacteria |
| ECF13 | >1146 | 33152898 | *Haemophilus ducreyi* 35000HP | Gammaproteobacteria | Proteobacteria |
| ECF13 | >1025 | 37524103 | *Photorhabdus luminescens* subsp. *laumondii* TTO1 | Gammaproteobacteria | Proteobacteria |
| ECF14 | >3200 | 15608361 | *Mycobacterium tuberculosis* H37Rv | | Actinobacteria |
| ECF14 | >1324 | 21223516 | *Streptomyces coelicolor* A3(2) | | Actinobacteria |
| ECF15 | >436 | 77464848 | *Rhodobacter sphaeroides* 2.4.1 | Alphaproteobacteria | Proteobacteria |
| ECF15 | >524 | 16127705 | *Caulobacter crescentus* CB15 | Alphaproteobacteria | Proteobacteria |
| ECF16 | >3622 | 104782321 | *Pseudomonas entomophila* L48 | Gammaproteobacteria | Proteobacteria |
| ECF16 | >973 | 161378140 | *Pseudomonas putida* KT2440 | Gammaproteobacteria | Proteobacteria |
| ECF17 | >1691 | 15607875 | *Mycobacterium tuberculosis* H37Rv | | Actinobacteria |
| ECF17 | >1458 | 21221399 | *Streptomyces coelicolor* A3(2) | | Actinobacteria |
| ECF18 | >4451 | 21230791 | *Xanthomonas campestris* pv. *campestris* str. ATCC 33913 | Gammaproteobacteria | Proteobacteria |
| ECF18 | >4438 | 21242133 | *Xanthomonas axonopodis* pv. *citri* str. 306 | Gammaproteobacteria | Proteobacteria |
| ECF19 | >3197 | 15607586 | *Mycobacterium tuberculosis* H37Rv | | Actinobacteria |
| ECF19 | >1315 | 21219164 | *Streptomyces coelicolor* A3(2) | | Actinobacteria |
| ECF20 | >992 | 70731405 | *Pseudomonas fluorescens* Pf-5 | Gammaproteobacteria | Proteobacteria |
| ECF20 | >2913 | 88706222 | gamma proteobacterium KT 71 | Gammaproteobacteria | Proteobacteria |
| ECF21 | >1280 | 29350128 | *Bacteroides thetaiotaomicron* VPI-5482 | | Bacteroidetes |
| ECF21 | >2825 | 89889680 | *Flavobacteria bacterium* BBFL7 | | Bacteroidetes |
| ECF22 | >4450 | 21232074 | *Xanthomonas campestris* pv. *campestris* str. ATCC 33913 | Gammaproteobacteria | Proteobacteria |
| ECF22 | >1147 | 21243541 | *Xanthomonas axonopodis* pv. *citri* str. 306 | Gammaproteobacteria | Proteobacteria |
| ECF23 | >231 | 15895043 | *Clostridium acetobutylicum* ATCC 824 | | Firmicutes |
| ECF23 | >1851 | 30261806 | *Bacillus anthracis* str. Ames | | Firmicutes |
| ECF24 | >69 | 16079737 | *Bacillus subtilis* subsp. *subtilis* str. 168 | | Firmicutes |
| ECF24 | >1034 | 32470052 | *Escherichia coli* | Gammaproteobacteria | Proteobacteria |
| ECF25 | >1645 | 170078575 | *Synechococcus* sp. PCC 7002 | | Cyanobacteria |
| ECF25 | >1643 | 17230772 | *Nostoc* sp. PCC 7120 | | Cyanobacteria |
| ECF26 | >4464 | 58581966 | *Xanthomonas oryzae* pv. *oryzae* KACC10331 | Gammaproteobacteria | Proteobacteria |
| ECF26 | >837 | 77459110 | *Pseudomonas fluorescens* PfO-1 | Gammaproteobacteria | Proteobacteria |
| ECF27 | >4265 | 21222299 | *Streptomyces coelicolor* A3(2) | | Actinobacteria |
| ECF27 | >1331 | 31795084 | *Mycobacterium bovis* AF2122/97 | | Actinobacteria |
| ECF28 | >1088 | 114563849 | *Shewanella frigidimarina* NCIMB 400 | Gammaproteobacteria | Proteobacteria |
| ECF28 | >1040 | 15641058 | *Vibrio cholerae* O1 biovar eltor str. N16961 | Gammaproteobacteria | Proteobacteria |
| ECF29 | >371 | 13476734 | *Mesorhizobium loti* MAFF303099 | Alphaproteobacteria | Proteobacteria |
| ECF29 | >2688 | 71281387 | *Colwellia osvchrervthraea* 34H | Gammaproteobacteria | Proteobacteria |
| ECF30 | >35 | 16079766 | *Bacillus subtilis* subsp. *subtilis* str. 168 | | Firmicutes |
| ECF30 | >83 | 18309341 | *Clostridium perfringens* str. 13 | | Firmicutes |
| ECF31 | >2963 | 85713274 | *Idiomarina baltica* OS145 | Gammaproteobacteria | Proteobacteria |
| ECF31 | >34 | 16080921 | *Bacillus subtilis* subsp. *subtilis* str. 168 | | Firmicutes |
| ECF32 | >1122 | 4581629 | *Erwinia amylovora* | Gammaproteobacteria | Proteobacteria |
| ECF32 | >3724 | 28868612 | *Pseudomonas syringae* pv. tomato str. DC3000 | Gammaproteobacteria | Proteobacteria |
| ECF33 | >375 | 27378153 | *Bradyrhizobium japonicum* USDA 110 | Alphaproteobacteria | Proteobacteria |
| ECF33 | >423 | 39934888 | *Rhodopseudomonas palustris* CGA009 | Alphaproteobacteria | Proteobacteria |
| ECF34 | >3302 | 77164965 | *Nitrosococcus oceani* ATCC 19707 | Gammaproteobacteria | Proteobacteria |
| ECF34 | >1384 | 21218750 | *Streptomyces coelicolor* A3(2) | | Actinobacteria |
| ECF35 | >3582 | 15598092 | *Pseudomonas aeruginosa* PAO1 | Gammaproteobacteria | Proteobacteria |
| ECF35 | >1119 | 24375055 | *Shewanella oneidensis* MR-1 | Gammaproteobacteria | Proteobacteria |
| ECF36 | >3196 | 15609206 | *Mycobacterium tuberculosis* H37Rv | | Actinobacteria |
| ECF36 | >1595 | 21219385 | *Streptomyces coelicolor* A3(2) | | Actinobacteria |
| ECF37 | >3390 | 89094252 | *Oceano spirillum* sp. MED92 | Gammaproteobacteria | Proteobacteria |
| ECF37 | >2513 | 83718468 | *Burkholderia thailandensis* E264 | Betaproteobacteria | Proteobacteria |
| ECF38 | >1322 | 21222029 | *Streptomyces coelicolor* A3(2) | | Actinobacteria |
| ECF38 | >1442 | 152967344 | *Kineococcus radiotolerans* SRS30216 | | Actinobacteria |
| ECF39 | >1438 | 21223369 | *Streptomyces coelicolor* A3(2) | | Actinobacteria |
| ECF39 | >2973 | 84494624 | *Janibacter* sp. HTCC2649 | | Actinobacteria |
| ECF40 | >3198 | 15610550 | *Mycobacterium tuberculosis* H37Rv | | Actinobacteria |
| ECF40 | >1380 | 62389491 | *Corynebacterium glutamicum* ATCC 13032 | | Actinobacteria |
| ECF41 | >491 | 16127496 | *Caulobacter crescentus* CB15 | Alphaproteobacteria | Proteobacteria |
| ECF41 | >1141 | 77459658 | *Pseudomonas fluorescens* PfO-1 | Gammaproteobacteria | Proteobacteria |
| ECF42 | >3583 | 15596548 | *Pseudomonas aeruginosa* PAO1 | Gammaproteobacteria | Proteobacteria |
| ECF42 | >4454 | 77747962 | *Xanthomonas campestris* pv. *campestris* str. ATCC 33913 | Gammaproteobacteria | Proteobacteria |
| ECF43 | >4437 | 21244845 | *Xanthomonas axonopodis* pv. *citri* str. 306 | Gammaproteobacteria | Proteobacteria |
| ECF43 | >3477 | 109897287 | *Pseudoalteromonas atlantica* T6c | Gammaproteobacteria | Proteobacteria |

In addition to native sigma factors, chimeric or other variant sigma factors can also be used in the method of the invention. For example, in some embodiments, one or more sigma factor are submitted to mutation to generate library of sigma factor variants and the resulting library can be screen for novel DNA binding activities.

In some embodiments, chimeric sigma factors formed from portions of two or more sigma factors can be used. Accordingly, embodiments of the invention provide for generating a library of polynucleotides encoding chimeric sigma factors, wherein the chimeric sigma factors comprise a domain from at least two different sigma factors, wherein each of the domains bind to the −10 or −35 region of a regulatory element; and expressing chimeric sigma factors from the library of polynucleotides, thereby generating a library of chimeric sigma factors. For example, in some embodiments, chimeric sigma factors are generated comprising a "Region 2" from a first sigma factor and a "Region 4" from a second sigma factor, thereby generating chimeric sigma factors with novel DNA binding activities. "Region 2" of sigma factors is a conserved domain that recognizes −10 regions of promoters. "Region 4" is a conserved domain of sigma factors that recognizes −35 regions of promoters. It will be appreciated that chimeric sigma factors can be generated from any two native sigma factors that bind different target DNA sequences (e.g., different promoter sequences). As noted in the Examples, it has been found that chimeric sigma factors formed from the ECF2 and ECF11 subgroups have unique DNA binding activities useful for generating orthogonal sets as described herein. Exemplary chimeric sigma factors include, but are not limited to, ECF11_ECF02 (containing amino acids 1-106 from ECF02_2817 and 122-202 from ECF11_3726) and ECF02_ECF11 (containing amino acids 1-121 from ECF11_3726 and 107-191 from ECF02_2817).

The ECF11_ECF02 amino acid sequence (SEQ ID NO:97) is as follows:

```
  1 MRITASLRTFCHLSTPHSDSTTSRLWIDEVTAVARQRDRDSFMRIYDHFAPRLLRYLTGL

61 NVPEGQAEELVQEVLLKLWHKAESFDPSKASLGTWLFRIARNLYIDSVRKDRGWVQVQNS

121 LEQLERLEAISNPENLMLSEELRQIVERTIESLPEDLRMAITLRELDGLSYEEIAAIMDC

181 PVGTVRSRIFRAREAIDNKVQPLIRR*
```

The ECF02_ECF11 amino acid sequence (SEQ ID NO:98) is as follows:

```
  1 MSEQLTDQVLVERVQKGDQKAFNLLVVRYQHKVASLVSRYVPSGDVPDVVQEAFIKAYRA

61 LDSFRGDSAFYTWLYRIAVNTAKNYLVAQGRRPPSSDVDAIEAENFEQLERLEAPVDRTL

121 DYSQRQEQQLNSAIQNLPTDQAKVLRMSYFEALSHREISERLDMPLGTVKSCLRLAFQKL

181 RSRIEES*
``` iii. RNA Polymerases

In some embodiments, the set of sequence-specific DNA-binding polypeptides comprise polypeptides having DNA binding activity and that are a variant of the T7 RNA polymerase (RNAP). The T7 RNAP amino acid sequence (SEQ ID NO:99) is as follows:

```
  1 mntiniaknd fsdielaaip fntladhyge rlareqlale hesyemgear frkmferqlk 61 agevadnaaa kplittllpk miarindwfe evkakrgkrp tafgflgeik peavayitik 121 ttlacltsad nttvqavasa igraiedear fgrirdleak hfkknveeql nkrvghvykk 181 afmqvveadm lskgllggea wsswhkedsi hvgvrcieml iestgmvslh rqnagvvgqd 241 setielapey aeaiatraga lagispmfqp cvvppkpwtg itgggywang rrplalvrth 301 skkalmryed vympevykai niaqntawki nkkvlavanv itkwkhcpve dipaiereel 361 pmkpedidmn pealtawkra aaavyrkdka rksrrislef mleqankfan hkaiwfpynm 421 dwrgrvyays mfnpqgndmt kglltlakgk pigkegyywl kihgancagv dkvpfperik 481 fieenhenim acaksplent wwaeqdspfc flafcfeyag vqhhglsync slplafdgsc 541 sgiqhfsaml rdevggravn llpsetvgdi ygivakkvne ilqadaingt dnevvtvtde 601 ntgeisekvk lgtkalagqw laygvtrsvt krsvmtlayg skefgfrqqv ledtiqpaid 661 sgkglmftqp nqaagymakl iwesysvtvv aaveamnwlk saakllaaev kdkktgeilr 721 krcavhwvtp dgfpvwqeyk kpiqtrlnlm flggfrlqpt intnkdseid ahkqesgiap
```

```
781 nfvhsqdgsh lrktvvwahe kygiesfali hdsfgtipad aanlfkavre tmvdtyescd 841 vladfydqfa dqlhesqldk mpalpakgnl nlrdilesdf afa
```

The T7 RNAP promoter has also been characterized (see, e.g., Rong et al., *Proc. Natl. Acad. Sci. USA* vol. 95 no. 2 515-519 (1998) and is well known.

As described in the Examples, methods have been discovered for generating orthogonal pairs of RNAP variants and target promoter variants. In some embodiments, one (e.g., 1, 2, 3, 4, 5, 6, 7, 8, 9, etc.) or more different RNA polymerases substantially identical to T7 RNAP is selected for use in an orthogonal set of cognate pairs and/or in a genetic circuit.

Due to toxicity of expression of native T7 RNAP, a series of mutations and modifications were designed such that a library of RNAP variants could be expressed and tested for activity in cells without excessive toxicity. Accordingly, embodiments of the invention provide for one or more of the following modifications (and thus, for example, an embodiment of the invention provides for host cells comprising expression cassettes, or nucleic acids comprising expression cassettes, wherein the expression cassette encodes a RNAP variant substantially identical to T7 RNAP, wherein the expression cassette comprises one or more of the following):

Expression of the T7 RNAP variant can be expressed from a low copy plasmid. Expression of the RNAP can be controlled by a separately encoded protein from a separate vector, thereby blocking expression of the RNAP until a second vector is added to the cells promoting RNAP expression;

Translational control: a GTG start codon; weak ribosomal binding sites (RBSs), and/or random DNA spacers to insulate RNAP expression can be used;

A molecular tag to promote rapid degradation of the RNAP. For example, an Lon N-terminal tag will result in rapid degradation of the tagged RNAP by the Lon protease system.

A mutated RNAP active site (e.g., within amino acids 625-655 of T7 RNAP). For example, it has been discovered that a mutation of the position corresponding to amino acid 632 (R632) of T7 RNAP can be mutated to reduce the RNAP's activity. In some embodiments, the RNAP contains a mutation corresponding to R632S.

Moreover, a variety of mutant T7 promoters have been discovered that can be used in a genetic circuit. Thus, in some embodiments, an expression cassette comprising a promoter operably linked to a second polynucleotide, wherein the promoter comprises a mutant sequence as set forth in FIG. 18, is provided. In some embodiments, a host cell comprises the expression cassette.

A number of different stem loop structures that function as terminators for T7 RNAP have been discovered. See, FIG. 19. Accordingly, an embodiment of the invention provides for expression cassettes comprising a promoter functional to a native T7 RNAP or an RNAP substantially identical thereto, wherein the operably lined polynucleotide encodes a terminator selected from FIG. 19.

Also provided are RNAP variants comprising and altered specificity loop (corresponding to positions between 745 and 761. Thus in some embodiments, an RNAP is provided that is identical or substantially identical to T7 RNAP but has a Loop Sequence selected from those in FIG. 20A between positions 745 and 761. Polynucleotides encoding such RNAPs are also provided. Similarly, an expression cassette comprising a promoter operably linked to a polynucleotide encoding such RNAPs are also provided.

Also provided are expression cassettes comprising a promoter, which promoter comprises a "Promoter Sequence" selected from FIG. 20A, operably linked to a second polynucleotide. As explained in the Examples, FIGS. 20A and 20B set forth orthogonal cognate pairs of RNAP variants and promoters. These pairs can be deployed to form genetic circuits as desired.

iv. Activators Requiring Chaperones

In some embodiments, the set of sequence-specific DNA-binding polypeptides comprise polypeptides having DNA binding activity and that require a separate chaperone protein to bind the sequence-specific DNA-binding polypeptide for the sequence-specific DNA-binding polypeptide to be active. Exemplary transcriptional activators requiring a chaperone for activity include, but are not limited to activator is substantially similar to InvF from *Salmonella typhimurium*, MxiE from *Shigella flexneri*, and ExsA from *Pseudomonas aeruginosa*. These listed activators require binding of SicA from *Salmonella typhimurium*, IpgC from *Shigella flexneri*, or ExsC from *Pseudomonas aeruginosa*, respectively, for activation.

Sequence information for the above components are provides as follows:

| Name | Type | DNA sequence encoding the named polypeptide (SEQ ID NO:) | Optional Mutation |
| --- | --- | --- | --- |
| sicA | Gene | Atggattatcaaaataatgtcagcgaagaacgtgttgcggaaa tgatttgggatgccgttagtgaaggcgccacgctaaaagacgt tcatgggatccctcaagatatgatggacggtttatatgctcat gcttatgagttttataaccagggacgactggatgaagctgaga cgttctttcgtttcttatgcatttatgattttttacaatcccga ttacaccatgggactggcggcagtatgccaactgaaaaaacaa tttcagaaagcatgtgacctttatgcagtagcgtttacgttac ttaaaaatgattatcgccccgttttttttaccgggcagtgtca attattaatgcgtaaggcagcaaaagccagacagtgtttttgaa cttgtcaatgaacgtactgaagatgagtctctgcgggcaaaag cgttggtctatctggaggcgctaaaaacggcggagacagagca gcacagtgaacaagaaaaggaataa (100) | |
| sicA* | Mutant sicA | Atggattatcaaaataatgtcagcgaagaacgtgttgcggaaa tgatttgggatgccgttagtgaaggcgccacgctaaaagacgt tcatgggatccctcaagatatgatggacggtttatatgctcat | The large "t" of the sicA sequence above was mutated to "a" by error-prone PCR. This |

| Name | Type | DNA sequence encoding the named polypeptide (SEQ ID NO:) | Optional Mutation |
|---|---|---|---|
| | | gcttatgagttttataaccagggacgactggatgaagctgaga cgttctttcttacttatgcatttatgattttttacaatcccgat tacaccatgggactggcggcagtatgccaactgaaaaaacaat ttcagaaagcatgtgacctttatgcagtagcgtttacgttact taaaaatgattatcgccccgttttttttaccgggcagtgtcaa ttattaatgcgtaaggcagcaaaagccagacagtgttttgaac ttgtcaatgaacgtactgaagatgagtctctgcgggcaaaagc gttggtctatctggaggcgctaaaaacggcggagacagagcag cacagtgaacaagaaaaggaataa (101) | mutation was made to reduce cross talk between SicA and MxiE. |
| invF | Gene with new start codon | Atgctaaatacgcaggaagtacttaaagaaggagagaagcgga aaatccgcagcccggaagcatggtttatacagacgtgttccgc gcaaaagctgcatatgtcattttctgaaagccgacacaatgaa aattgcctgattcaggaaggcgcgctgcttttttgcgagcagg ccgttgtcgcaccagtatcaggagacctggttttttcgaccgtt aaaaattgaagtactcagcaaattactggcatttatcgatggc gcaggattagtggacacgacatatgctgaatccgataaatggg ttttgctgagtcctgagtttcgcgctatttggcaagatcgtaa acgctgcgagtactggttttttgcagcaaattattacgccttct ccggccttcaataaggtactggcgctgttacgaaaaagcgaga gttactggttggttggctatttactcgctcagtcaaccagcgg caacacgatgagaatgctgggagaagactatggcgtttcttat acccattttcgtcgtttgtgcagcagagcgttgggcggaaaag cgaagagtgaattacgaaactggcgtatggcgcaatcgctgct gaatagtgtagaaggccacgagaacatcacccaattagccgtt aatcatggttactcatcgccttcacatttttctagtgagatca aagagctgatcggcgtttcgccgcggaaattatcaaatattat tcaattggcagacaaatga (102) | The accepted start codon (the large "atg") was determined to be incorrect and a correct upstream start codon was found. |
| psicA | Promoter | Ccacaagaaacgaggtacggcattgagccgcgtaaggcagtag cgatgtattcattgggcgttttttgaatgttcactaaccaccg tcggggtttaataactgcatcagataaacgcagtcgttaagtt ctacaaagtcggtgacagataacaggagtaagta (103) | |
| ipgC | Gene | Atgtctttaaatatcaccgaaaatgaaagcatctctactgcag taattgatgcaattaactctggcgctacactgaaagatattaa tgcaattcctgatgatatgatggatgacatttattcatatgct tatgacttttacaacaaaggaagaatagaggaagctgaagttt tcttcaggttttttatgtatatcgacttttacaatgtagacta cattatgggactcgcagctatttatcagataaaagaacagttc caacaagcagcagaccctttatgctgtcgcttttgcattaggaa aaaatgactatacaccagtattccatactggacaatgtcagct tcggttgaaagccccccttaaaagctaaagagtgcttcgaactc gtaattcaacacagcaatgatgaaaaattaaaaataaaagcac aatcatacttggacgcaattcaggatatcaaggagtaa (104) | |
| mxiE | Gene with codon optimization | atgagtaaatataaaggcctgaacaccagcaacatgttctaca tctacagctctggtcatgaaccggtgaacgttgaactggtgaa agataaagaacgtaacatcatcgaactggcaccggcgtggaaa ggcttttctttgtgcgtaaccagaacatcaaattcagcgata acgttaactaccactaccgcttcaacatcaactcttgcgcaaa attcctggcgttttgggattattttagcggcgccctggttgaa cattctcacgcagaaaaatgcatccattttctaccacgaaaacg atctgcgtgatagctgtaatacggaatctatgctggataaact gatgctgcgcttcattttttagtagcgatcagaacgtgtctaat gccctggcaatgatccgtatgaccgaaagttatcatctggttc tgtacctgctgcgtacgattgaaaaagaaaaagaagtgcgcat caaaagcctgaccgaacactatggcgttctgaagcgtactttt cgtagtctgtgtcgcaaagcgctgggtgccaaagtgaaagaac agctgaacacgtggcgcctggtgaatggcctgctggatgttttt cctgcataaccagaccattacgagcgcggccatgaacaatggt tatgcgtctaccagtcacttcagcaatgaaattaaaacgcgtc tgggctttagtgcccgcgaactgagcaacatcaccttcctggt gaagaaaattaatgaaaaaatctaa (105) | The wide type gene has "tttttttt" in this enlarged sequence region. One more "t" was added to make "ttttttttt" and then the entire gene was codon optimized by GenScript. The additional "t" was added to make this ORF in-frame. In addition, the wide-type gene starts with "g" and this synthetic gene starts with "a." |
| pipaH9.8 | Promoter | gcgaaaatgacatcaaaaacgccattaacctgatgttctgggg aatataaatgtcaggctagggtcaaaaatcgtggcggttgaca aaatggctgcgttacgtcattgagcatatccaggactggccgg caaaccgggtacgcgatctgttgccttggaaagttgatctgac ctctcagtaaatatcaatacggttctgacgagccgcttaccgt tcaaatatgaagtacgatgtttaactaaccgaaaaacaagaac aatacggtgcaaacaggccattcacggttaactgaaacagtat cgttttttttacgccaatttgtttatcctttattaataaaaa atgct (106) | |

-continued

| Name | Type | DNA sequence encoding the named polypeptide (SEQ ID NO:) | Optional Mutation |
| --- | --- | --- | --- |
| pipaH9.8* | Promoter with mutation | gcgaaaatgacatcaaaaacgccattaacctgatgttctgggg aatataaatgtcaggctagggtcaaaaatcgtggcgttgacaa aatgctgcgttacgtcattgagcatatccaggactggccggc aaaccgggtacgcgatctgttgccttggaaagttgatctgacc tctcagtaaatatcaatacggttctgacgagccgctaccgttc aaatatgaagtacgatgtttaactaaccgaaaaacaagaacaa tacggtgcaaacaggccattcacggttaactgaaacagtatcg ttttttttacagccaattttgtttatccttattaagataaaaaaa gtgct (107) | The enlarged "ta" above of pipaH9.8 was mutated to "ag" by saturation mutagenesis. This mutation was made to reduce leaky expression of pipaH9.8. |
| exsC | Gene | atggatttaacgagcaaggtcaaccgactgcttgccgagttcg caggccgtatcggtttgccttccctgtccctcgacgaggaggg catggcgagcctcctgttcgacgaacaggtgggcgtcaccctg ttgctgctcgccgagcgcgagcgtctgttgctggaggccgatg tggcgggcatcgatgtgctgggcgaggggatctttcgccagct cgccagcttcaaccgccattggcaccgtttcgatctgcatttc ggcttcgacgagctgaccggcaaggtccagttgtatgcgcaga ttctcgcagcgcaactgaccctcgaatgcttcgaggcgacctt ggccaatctgctcgatcacgccgagttctggcagcgcctgctg ccgtgcgacagtgatcgcgaggcggtcgctgcggtcggcatga gggtttga (108) | |
| exsD | Gene | atggagcaggaagacgataagcagtactcccgagaagcggtgt tcgctggcaggcgggtatccgtggtgggctcggacgcccgctc gcggggtcgggtgccgggttacgcatcgagcagtttgtatcgt gagtccggaatcatcagtgcgcggcaactggcgttgctgcagc ggatgctgccgcgcctgcgcttggagcaactgttccgctgcga gtggttgcagcagcgcctggcgcgcggcctggcgctggggcgc gaagaggtgcggcagattctcctctgcgcggcgcaggacgacg acggctggtgctccgaactgggcgacccgggtcaacctcgccgt gccgcagtcgatgatcgactgggtcctgctgccggtctatggc tggtggggaaagcctgctcgaccaggcgatccccggctggcgcc tgtcgctggtggagctggagacccagtcccggcaactgcgagt caagtccgaattctggtcccgcgtggccgagctggagccggag caggcccgcgaggaactggccagggtcgccaagtgccaggcgc gcaccaggaacaggtggccgaactggccggcaagctggagac ggcttcggcactggcgaagagcgcctggccgaactggcagcgg ggcatggcgacgctgctcgcagcggcgggctggccggcttcg agccgatccccgaggtcctcgaatgcctctggcaacctctctg ccggctggacgacgacgtcggcgcggcggacgccgtccaggcc tggctgcacgaacgcaacctgtgccaggcacaggatcacttct actggcagagctga (109) | |
| exsA | Gene | atgcaaggagccaaatctcttggccgaaagcagataacgtctt gtcattggaacattccaactttcgaatacagggtaaacaagga agagggcgtatatgttctgctcgagggcgaactgaccgtccag gacatcgattccacttttttgcctggcgcctggcgagttgcttt tcgtccgccgcggaagctatgtcgtaagtaccaagggaaagga cagccgaatactctggattccattatctgcccagtttctacaa ggcttcgtccagcgcttcggcgcgctgttgagtgaagtcgagc gttgcgacgagcccgtgccgggcatcatcgcgttcgctgccac gcctctgctggccggttgcgtcaaggggttgaaggaattgctt gtgcatgagcatccgccgatgctcgcctgcctgaagatcgagg agttgctgatgctcttcgcgttcagtccgcaggggccgctgct gatgtcggtcctgcggcaactgagcaaccggcatgtcgagcgt ctgcagctattcatggagaagcactacctcaacgagtggaagc tgtccgacttctcccgcgagttcggcatggggctgaccaccttt caaggagctgttcggcagtgtctatggggtttcgccgcgcgcc tggatcagcgagcggagaatcctctatgcccatcagttgctgc tcaacagcgacatgagcatcgtcgacatcgccatggaggcggg cttttccagtcagtcctatttcacccagagctatcgccgccgt ttcggctgcacgccgagccgctcgcggcaggggaaggacgaat gccgggctaaaaataactga (110) | |
| pexsD | Promoter | gaaggacgaatgccgggctaaaaataactgacgttttttgaaa gcccggtagcggctgcatgagtagaatcggcccaaat (111) | |
| pexsC | Promoter | gatgtggcttttttcttaaaagaaaagtctctcagtgacaaaa gcgatgcatagcccggtgctagcatgcgctgagcttt (112) | |
| rfp | Gene | atggcttcctccgaagacgttatcaaagagttcatgcgtttca agttcgtatggaaggttccgttaacggtcacgagttcgaaat cgaaggtgaaggtgaaggtcgtccgtacgaaggtacgcagacc gctaaactgaaagttaccaaaggtggtccgctgccgttcgctt gggacatcctgtccccgcagttccagtacggttccaaagctta cgttaaacacccggctgacatcccggactacctgaaactgtcc | |

| Name | Type | DNA sequence encoding the named polypeptide (SEQ ID NO:) | Optional Mutation |
|---|---|---|---|
| | | ttcccggaaggtttcaaatgggaacgtgttatgaacttcgaag acggtggtgttgttaccgttacccaggactcctccctgcaaga cggtgagttcatctacaaagttaaactgcgtggtactaacttc ccgtccgacggtccggttatgcagaaaaaaaccatgggttggg aagcttccaccgaacgtatgtacccggaagacggtgctctgaa aggtgaaatcaaaatgcgtctgaaactgaaagacggtggtcac tacgacgctgaagttaaaaccacctacatggctaaaaaaccgg ttcagctgccgggtgcttacaaaaccgacatcaaactggacat cacctcccacaacgaagactacaccatcgttgaacagtacgaa cgtgctgaaggtcgtcactccaccggtgctgcagcaaacgacg aaaactacgcttaa (113) | |

In some embodiments, one (e.g., 1, 2, 3, 4, 5, 6, 7, 8, 9, etc.) or more transcriptional activators requiring chaperones (e.g., those substantially identical to a transcriptional activator listed above), as well as its corresponding chaperone is selected for use in an orthogonal set of cognate pairs and/or in a genetic circuit.

B. Transcriptional Repressors i. General

It is believed that any class of transcriptional repressors can be adapted for use in the methods described herein.

ii. Tet Repressors

In some embodiments, the set of sequence-specific DNA-binding polypeptides comprise polypeptides having DNA binding activity and that are a variant of the Tet Repressor (TetR). The Tet R protein and operator sequences are provided in, e.g., Postle et al., *Nucl. Acid Res.* 12:4849-4863 (1984); Hillen et al., *Ann. Rev. Microbiol.* 48:345-369 (1994); Wissmann et al., *J Mol. Biol.* 202:397-406 (1988)). A wide variety of organisms have repressor proteins with homology to $Tet^R$ that bind target DNA sequences other than the classical Tet operator. Thus, a diversity of $Tet^R$ homologs are available to generate a set of polypeptides that are substantially identical to $Tet^R$. As demonstrated in the Examples, $Tet^R$ homologs can be identified in metagenomic gene searches and then tested to determine their target DNA sequence(s) (as further discussed below). Table 2 provides a selected (non-limiting) list of potential $Tet^R$ homologs. Table 3 provides a list target DNA sequences (labeled in the table as "operators") to which the listed $Tet^R$ homologs bind.

TABLE 2

| Repressor | SwissProt ID | Organism |
|---|---|---|
| AcrR | P0ACT0 | *Escherichia coli* |
| AmeR | Q9F8V9 | *Agrobacterium tumefaciens* |
| AmrR | Q9RG61 | *Pseudomonas aeruginosa* |
| AmtR | Q9S3L4 | *Corynebacterium glutamicum* |
| ArpA | Q54189 | *Streptomyces griseus* |
| ArpR | Q9KJC4 | *Pseudomonas putida* |
| BarA | Q9LBV6 | *Streptomyces virginiae* |
| BarB | O24739 | *Streptomyces virginiae* |
| BetI | P17446 | *Escherichia coli* |
| BM1P1 | O68276 | *Bacillus megaterium* |
| BM3R1 | P43506 | *Bacillus megaterium* |
| BpeR | Q6VV70 | *Burkholderia pseudomallei* |
| ButR | Q9AJ68 | *Streptomyces cinnamonensis* |
| CalR1 | Q8KNI9 | *Micromonospora echinospora* |
| CampR | Q93TU7 | *Rhodococcus erythropolis* |
| CasR | Q9F6W0 | *Rhizobium etli* |
| CprB | O66129 | *Micrococus luteus* |
| CymR | O33453 | *Psudomonas putida* |
| Cyp106 | Q59213 | *Bacillus megaterium* |
| DhaR | Q9RAJ1 | *Mycobacterium sp. GP1* |
| Ef0113 | Q8KU49 | *Enterococcus faecalis* |

TABLE 2-continued

| Repressor | SwissProt ID | Organism |
|---|---|---|
| EnvR | P0ACT2 | *Escherichia coli* |
| EthR | P96222 | *Mycobacterium tubercolosis* |
| FarA | O24741 | *Streptomyces lavendulae* |
| HapR | O30343 | *Vibrio cholerae* |
| HemR | P72185 | *Propionibacterium freudenreichii* |
| HlyIIR | Q63B57 | *Bacillus cereus* |
| IcaR | Q9RQQ0 | *Staphylococcus aureus* |
| IcaR | Q8GLC6 | *Staphylococcus epidermidis* |
| IfeR | O68442 | *Agrobacterium tumefaciens* |
| JadR2 | Q56153 | *Streptomyces venezuelae* |
| KstR | Q9RA03 | *Rhodococcus erythropolis* |
| LanK | Q9ZGB7 | *Streptomyces cyanogenus* |
| LitR | Q8KX64 | *Vibrio fischeri* |
| LmrA | O34619 | *Bacillus subtilis* |
| LuxT | Q9ANS7 | *Vibrio harveyi* |
| McbR | Q8NLK1 | *Corynebacterium glutamicum* |
| MmfR | Q9JN89 | *Streptomyces coelicolor* |
| MphB | Q9ZN97 | *Escherichia coli* |
| MphR | Q9EVJ6 | *Escherichia coli* |
| MtrR | P39897 | *Neisseria gonorrhoeae* |
| NonG | Q9XDF0 | *Streptomyces griseus* |
| OpaR | O50285 | *Vibrio parahaemolyticus* |
| Orf2 | Q9XDV7 | *Streptomyces griseus* |
| orfL6 | Q8VV87 | *Terrabacter sp. DBF63* |
| PaaR | Q9FA56 | *Azoarcus evanssi* |
| PhaD | Q9F9Z7 | *Pseudomonas resinovorans* |
| PhlF | Q9RF02 | *Pseudomonas fluorescens* |
| PqrA | Q9F147 | *Streptomyces coelicolor* |
| PsbI | Q9XDW2 | *Rhodopseudomonas palustris* |
| PsrA | Q9EX90 | *Pseudomonas putida* |
| Q9ZF45 | Q9ZF45 | *Lactococcus lactis* |
| QacR | P0A0N4 | *Staphylococcus aureus* |
| RmrR | Q9KIH5 | *Rhizobium etli* |
| ScbR | O86852 | *Streptomyces coelicolor* |
| SmcR | Q9L8G8 | *Vibrio vulnificus* |
| SmeT | Q8KLP4 | *Stenotropomonas maltophilia* |
| SrpR | Q9R9T9 | *Pseudomonas putida* |
| TarA | Q9RPK9 | *Streptomyces tendae* |
| TcmR | P39885 | *Streptomyces glaucescens* |
| ThlR | O85706 | *Clostridium acetobutylicum* |
| TtgR | Q9AIU0 | *Pseudomonas putida* |
| TtgW | Q93PU7 | *Pseudomonas putida* |
| TylP | Q9XCC7 | *Streptomyces fradiae* |
| TylQ | Q9ZHP8 | *Streptomyces fradiae* |
| UidR | P0ACT6 | *Escherichia coli* |
| UrdK | Q9RP98 | *Streptomyces fradiae Tu2717* |
| VanT | Q8VQC6 | *Vibrio anguillarum* |
| VarR | Q9AJL5 | *Streptomyces virginiae* |
| YdeS | P96676 | *Bacillus subtilis* |
| YDH1 | P22645 | *Xanthobacter autotrophicus* |
| YixD | P32398 | *Bacillus subtilis* |
| YjdC | P0ACU7 | *Escherichia coli* |

TABLE 3

| Repressor | Operator sequence (SEQ ID NO:) | Length |
|---|---|---|
| McbR | TGAACAGCTTGGTCTA (114) | 16 |
| UidR | CTATTGGTTAACCAATTT (115) | 18 |
| BM3R1 | CGGAATGAACGTTCATTCCG (116) | 20 |
| AmtR | ATTATCTATAGATCGATAGAAA (117) | 22 |
| BetI | TTATATTGAACGTCCAATGAAT (118) | 22 |
| HapR | TTATTGATTTTTAATCAAATAA (119) | 22 |
| HlyIIR | TTTAAACAAGAATTTTAAATAT (120) | 22 |
| SmcR | TTATTGATAAATCTGCGTAAAA (121) | 22 |
| AcrR | TACATACATTTATGAATGTATGTA (122) | 24 |
| ArpA | CGACATACGGGACGCCCCGTTTAT (123) | 24 |
| LmrA | AGATAATAGACCAGTCACTATATT (124) | 24 |
| BarA | AGATACATACCAACCGGTTCTTTTGA (125) | 26 |
| QacR | CTTATAGACCGATCGCACGGTCTATA (126) | 26 |
| TylP | ATACAAACCGCGTCAGCGGTTTGTAA (127) | 26 |
| MtrR | TTTTTATCCGTGCAATCGTGTATGTAT (128) | 27 |
| FarA | GATACGAACGGGACGGACGGTTTGCAGC (129) | 28 |
| IcaR Se | ACAACCTAACTAACGAAAGGTAGGTGAA (130) | 28 |
| SchR | GAAAAAAACCGCTCTAGTCTGTATCTTA (131) | 29 |
| PhlF | ATGATACGAAACGTACCGTATCGTTAAGGT (132) | 30 |
| SmeT | GTTTACAAACAAACAAGCATGTATGTATAT (133) | 30 |
| MphR | GAATATAACCGACGTGACTGTTACATTTAGG (134) | 31 |
| LuxT | TTCGGTTTACTTTGTTTAGAATACCCACGTCT (135) | 32 |
| PsrA | AGCAGGGCTGAAACGTATGTTTCAAACACCTGTTTCTG (136) | 38 |
| ItgR | CAGCAGTATTTACAAACAACCATGAATGTAAGTATATTCC (137) | 40 |
| VarR | CACTTGTACATCGTATAACTCTCATATACGTTGTAGAACAG (138) | 41 |
| EthR | GTGTCGATAGTGTCGACATCTCGTTGACGGCCTCGACATTACG TTGATAGCGTGG (139) | 55 |

In some embodiments, one (e.g., 1, 2, 3, 4, 5, 6, 7, 8, 9, etc.) or more repressors from Table 2 (or substantially identical to a repressor in Table 2) is selected for use in an orthogonal set of cognate pairs and/or in a genetic circuit.

iii. Tal Effectors

In some embodiments, the set of sequence-specific DNA-binding polypeptides comprise Tal effectors. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcript (see Kay et al (2007) *Science* 318:648-651). These proteins contain a DNA binding domain and a transcriptional activation domain. One of the most well characterized TAL-effectors is AvrBs3 from *Xanthomonas campestgris* pv. *vesicatoria* (see Bonas et al (1989) *Mol Gen Genet* 218: 127-136 and WO2010079430). TAL-effectors contain a centralized domain of tandem repeats, each repeat containing approximately 34 amino acids, which control the DNA binding specificity of these proteins. In addition, they contain a nuclear localization sequence and an acidic transcriptional activation domain (for a review see Schomack S, et al (2006) *J Plant Physiol* 163(3): 256-272).

Specificity of TAL effectors depends on the sequences found in the tandem repeats. The repeated sequence comprises approximately 102 bp and the repeats are typically 91-100% homologous with each other. Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the code for DNA recognition of these TAL-effectors has been determined such that an HD sequence at positions 12 and 13 leads to a binding to cytosine (C), NG binds to T, NI to A, C, G or T, NN binds to A or G, and IG binds to T. These DNA binding repeats have been assembled into proteins with new combinations and numbers of repeats, to make artificial transcription factors that are able to interact with new sequences and activate the expression of a reporter gene in plant cells (Boch et al (2009) *Science* 326:1509-1512d). Accordingly, the set of sequence-specific DNA-binding polypeptides can comprise native or non-natural Tal effectors.

In some embodiments, one (e.g., 1, 2, 3, 4, 5, 6, 7, 8, 9, etc.) or more Tal effectors is selected for use in an orthogonal set of cognate pairs and/or in a genetic circuit.

iv. Zinc Fingers

In some embodiments, the set of sequence-specific DNA-binding polypeptides comprise zinc finger DNA binding domains. Zinc finger binding domains can be engineered to recognize and bind to any nucleic acid sequence of choice. See, for example, Beerli et al. (2002) *Nat. Biotechnol.* 20:135-141; Pabo et al. (2001) *Ann. Rev. Biochem.* 70:313-340; Isalan et al. (2001) *Nat. Biotechnol.* 19:656-660; Segal et al. (2001) *Curr. Opin. Biotechnol.* 12:632-637; Choo et al. (2000) *Curr. Opin. Struct. Biol.* 10:411-416; Zhang et al. (2000) *J. Biol. Chem.* 275(43):33850-33860; Doyon et al. (2008) *Nat. Biotechnol.* 26:702-708; and Santiago et al. (2008) *Proc. Natl. Acad. Sci. USA* 105:5809-5814. An engineered zinc finger binding domain can have a novel binding specificity compared to a naturally-occurring zinc finger protein. Engineering methods include, but are not limited to, rational design and various types of selection. Rational design includes, for example, using databases comprising doublet, triplet, and/or quadruplet nucleotide sequences and individual zinc finger amino acid sequences, in which each doublet, triplet or quadruplet nucleotide sequence is associated with one or more amino acid sequences of zinc fingers which bind the particular triplet or quadruplet sequence. See, for example, U.S. Pat. Nos. 6,453,242 and 6,534,261. Alternative methods, such as rational design using a nondegenerate recognition code table may also be used to design a zinc finger binding domain to target a specific sequence (Sera et al. (2002) *Biochemistry* 41:7074-7081). Publically available web-based tools for identifying potential target sites in DNA sequences and designing zinc finger binding domains may be found at http://www.zincfingertools.org and http://bindr.gdcb.iastate.edu/ZiFiT/, respectively (Mandell et al. (2006) *Nuc. Acid Res.* 34:W516-W523; Sander et al. (2007) *Nuc. Acid Res.* 35:W599-W605).

A zinc finger DNA binding domain may be designed to recognize a DNA sequence ranging from about 3 nucleotides to about 21 nucleotides in length, or from about 8 to about 19 nucleotides in length. In some embodiments, the zinc finger binding domains comprise at least three zinc finger recognition regions (i.e., zinc fingers). In one embodiment, the zinc finger binding domain may comprise four zinc finger recognition regions. In another embodiment, the zinc finger binding domain may comprise five zinc finger recognition regions. In still another embodiment, the zinc finger binding domain may comprise six zinc finger recognition regions. A zinc finger binding domain may be designed to bind to any suitable target DNA sequence. See for example, U.S. Pat. Nos. 6,607,882; 6,534,261 and 6,453,242.

Exemplary methods of selecting a zinc finger recognition region may include phage display and two-hybrid systems, and are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in WO 02/077227.

Zinc finger recognition regions and/or multi-fingered zinc finger proteins may be linked together using suitable linker sequences, including for example, linkers of five or more amino acids in length. See, U.S. Pat. Nos. 6,479,626; 6,903,185; and 7,153,949, for non-limiting examples of linker sequences of six or more amino acids in length. The zinc finger binding domains described herein may include a combination of suitable linkers between the individual zinc fingers of the protein.

In some embodiments, one (e.g., 1, 2, 3, 4, 5, 6, 7, 8, 9, etc.) or more zinc fingers is selected for use in an orthogonal set of cognate pairs and/or in a genetic circuit.

III. Optimizing Expression of Sequence-Specific DNA Binding Polypeptides

Once a set of sequence-specific DNA binding polypeptides have been identified, in some embodiments, expression of the polypeptides is optimized for expression in a heterologous host cell. Optimization will generally include a determination of polynucleotides encoding the polypeptides in the set (and ideally no additional promoter or terminator sequences) and then alteration of the polynucleotide for expression in the host cell.

Optimizing involves alteration of one or more codon in the coding sequence. The codon changes can result in codon optimization for the host cell, i.e., the cell in which the polynucleotide is to be expressed for testing and/or for expressing as part of a genetic circuit. Methods of codon optimization are known (e.g., Sivaraman et al., *Nucleic Acids Res.* 36:e16 (2008); Mirzahoseini, et al., Cell Journal (Yakhteh) 12(4):453 Winter 2011; U.S. Pat. No. 6,114,148) and can include reference to commonly used codons for a particular host cell. In some embodiments, one or more codon is randomized, i.e., a native codon is replaced with a random codon encoding the same amino acid. This latter approach can help to remove any cis-acting sequences involved in the native regulation of the polypeptide. In some embodiments, an algorithm is used to eliminate transcriptionally functional sequences in a gene encoding the polypeptide. For example, in some embodiments, ribosome binding sites, transcriptional regulatory elements, terminators, or other DNA sequences bound by proteins are removed from the native coding sequence. Notably, the functional sequences removed can be functional in the native species (from which the sequence was originally derived), from the heterologous host cell, or both. In some embodiments, optimizing comprises removal of sequences in the native coding sequence that are functional for other sequence-specific DNA binding polypeptides in the set of sequence-specific DNA binding polypeptides.

In some embodiments, as noted above, optimization will depend on the host cell used. Host cells can be any prokaryotic cell (including but not limited to *E. coli*) or eukaryotic cell (including but not limited to yeast cells, mammalian cells, avian cells, amphibian cells, plant cells, fish cells, and insect cells).

In some embodiments, expression of the sequence-specific DNA binding polypeptides is optimized for a particular host cell for production of the polypeptide for testing (e.g., identification of target DNA sequences of the polypeptides) and also optimized for expression in a second host cell in which the ultimate genetic circuit will be expressed.

IV. Identification of Target DNA Sequences to which Sequence-Specific DNA Binding Polypeptides Bind Once a set of sequence-specific DNA binding polypeptides have been provided and expressed, the polypeptides can be tested to identify DNA sequences to which the polypeptides bind ("target DNA sequences"). Identification of target DNA sequences can be performed in vitro or in vivo.

A. In Vitro

In some embodiments, the target DNA sequence(s) for polypeptides are determined in vitro. For example, sequence-specific DNA binding polypeptides can be expressed (e.g., via optimized expression from a host cell), optionally purified as needed, labeled, and contacted to an array of polynucleotides under conditions to allow for sequence-specific binding of the polypeptide to any target polynucleotides present on the array. The location of the label on the array can subsequently to used to determine the identity of the target polynucleotide bound. A variety of different arrays (e.g., comprising 100s, to 1000s, millions, or more polynucleotides) can be used. In some embodiments, microarray technology is used.

As desired, polynucleotides having random sequences, and/or sequences of random length, can be screened for their ability to bind to the sequence-specific DNA binding polypeptides. In some embodiments, the polynucleotides in the array are rationally designed. For example, in some embodiments, the polynucleotides are designed to include a hairpin structure. For example, the hairpin can contain, and thereby display, the target DNA sequence. Hairpins can be designed to have various lengths and sequences. In some embodiments, the hairpins comprise an inverted repeat. For example, the inverted repeats can have 20, 22, 24, 26, 28, 30, 32, 34, 36 or more nucleotides.

In some embodiments, the inverted sequence has a T at position 14, A at position 13, A at position 7, T at position −7, T at position −13, and A at position −14. The positions are counted backwards starting from the axis of symmetry (center of the probe), which begins with the number 1 (or −1, for the adjacent complement).

In some embodiments, the polynucleotides are designed to allow for a sufficient sequence diversity while making a limited number of polynucleotides (e.g., when the number of positions on an array are limited). In some embodiments, the hairpin sequences are designed to have no more than a particular GC content, thereby limiting the possible number of sequences without significantly altering the available diversity. In some embodiments, the GC content of the hairpin is equal or less than 25% 40%, 35%, 30%, 25%, 20% or less.

In some embodiments, an in vitro or in vivo method can be used for identifying target DNA sequences (e.g., operators). For example, in some embodiments, a library of putative transcriptional activator (e.g., sigma factor) binding polynucleotide sequences, which are predicted to bind to a particular transcriptional activator or portions thereof, is constructed. The library can comprise randomized, putative transcriptional activator binding polynucleotide sequences inserted into plasmids without terminator sequences. When contacted with the transcriptional activator and RNA polymerase (e.g., E. coli RNA polymerase), the plasmid is transcribed, thereby creating RNA transcripts complementary to the DNA sequence of the plasmid. Since the plasmids of the library do not have transcriptional terminators, transcription of the plasmids will not end until the RNA polymerase is no longer in contact with the plasmid. In some instances, an increase in quantity of RNA will indicate that the transcriptional activators have successfully bound to transcriptional operators and generated RNA transcripts. In other instances, the absence of an increase in RNA quantity will suggest that the transcriptional activators and RNA polymerase may not have bound to operator sequences to activate transcription. In some embodiments, an in vitro transcription assay is used to determine the level of transcription from the plasmids of the library when in the presence of the sigma factor. In other embodiments, an in vivo transcription assay is used to identify the plasmids in the library constructed with sigma factor target binding polynucleotide sequences. For example, plasmids of the library can be transformed in the host cells expressing sigma factors, chimeric sigma factors, or portions thereof, and then RNA transcripts generated from the plasmid can be quantified. The RNA transcripts from transcription assays can be quantified by methods, including, but not limited to, high-throughput sequencing, RNA-seq, next-generation RNA sequencing, microarray, or quantitative RT-PCR.

B. In Vivo

In some embodiments, the target DNA sequence(s) for polypeptides are determined in vivo. For instance, in vivo methods for identifying target DNA sequences can include generation of synthetic transcriptional regulatory elements comprising potential DNA target sequences operably linked to a reporter gene (thereby forming a reporter expression cassette), and testing such reporter expression cassette in a host cell for transcriptional response to a sequence-specific DNA binding polypeptide expressed in the cell. The particular expression response will depend on whether the sequence-specific DNA binding polypeptide is an activator (in which case increased expression is a positive response) or a repressor (in which case reduced expression is a positive response).

In some embodiments, a synthetic regulatory element library is constructed wherein library members comprise different target DNA sequence(s). The base regulatory element will comprise at least a minimal promoter functional in the host cell and can optionally comprise further cis-acting regulatory elements. The potential target DNA sequence(s) can be position anywhere within the regulatory element useful for testing promoter activity. The position of the potential target DNA sequence will depend, in part, on the particular type of sequence-specific DNA binding polypeptide being tested. In some embodiments, the regulatory element comprises −10 and −35 regions and the potential target DNA sequence binding region is located between the −10 and −35 regions of the regulatory element. In some embodiments, the potential target DNA sequence comprises one or both of the −10 or −35 regions of the regulatory element. In some embodiments, the position of the target DNA sequence in the regulatory element is selected from: at the −10 or −35 region of the regulatory element, in the UP-region of the regulatory element, upstream of the −35 site, between the −10 and −35 sites. between the −10 and transcriptional start site, overlapping the transcriptional start site, and overlapping an activator binding site.

Potential target DNA sequences in the library of regulatory elements can be generated, for example, by design or random mutagenesis.

The regulatory element (e.g., minimal promoter) can be function in a prokaryotic cell, a eukaryotic, or both. Sequences within the regulatory element can be derived from eukaryotic promoters, prokaryotic promoters, or can be synthetic variants of such sequences.

Once the library of regulatory elements has been generated, the library can be screened in host cells to determine whether, and/or to what extent, expression of a sequence-specific DNA binding polypeptide results in activation or repression of transcription from the library expression cassettes. Once library members are identified with the desired activity, the target DNA sequences within the regulatory element can be determined (e.g., by reference to a database of library members, or nucleotide sequencing, etc.).

V. Generation of Synthetic Transcriptional Regulatory Elements

Once target DNA sequence(s) bound by a sequence-specific DNA binding polypeptide are identified, the activity of one or more of the target DNA sequences can be tested to confirm the cognate sequence-specific DNA binding polypeptide binds to the target DNA sequence in the context of the regulatory element and/or regulates expression controlled by the regulatory element. In some embodiments, this activity test will have been completed in the target DNA sequence identification process (see, e.g., the in vivo screening process discussed above). However, even in situations in which target DNA sequences have been found to function in regulatory elements, it may be desirable to modify the position of the DNA sequence in the regulatory element and/or test the DNA sequence in one or more additional regulatory elements.

VI. Design of Cognate Pairs

Embodiments of the invention also provides for generation of sets of cognate sequence-specific DNA binding polypeptide-target DNA sequence pairs for use in a genetic circuit. It will be appreciated that in essentially any initial set of sequence-specific DNA binding polypeptides and their target DNA sequences, there will be "overlap" in target DNA sequences between different polypeptides. Therefore, embodiments of the invention provides for methods of generating a set of cognate orthogonal sequence-specific DNA binding polypeptide-target DNA sequence pairs, i.e., pairs of polypeptides/DNA sequences that do not interact with each other. In view of knowledge (e.g., from empirical data) regarding the DNA binding sequence of each sequence-specific DNA binding polypeptide of interest, one can design a set of cognate pairs.

In some embodiments, the method comprises identifying a set of sequence-specific DNA-binding polypeptides that do not bind to each other's target DNA sequences.

Design of sets of cognate sequence-specific DNA binding polypeptide-target DNA sequence pairs can, in some embodiments, involve maximizing the size of the set of orthogonal sequence-specific DNA binding polypeptide-target DNA sequence pairs. This sort of design can involve, for example, bioinformatic algorithms to maximize the set based on the cognate pairs available. For example, bioinformatic models can be employed that maximize the diversity between target DNA sequences in the set of orthogonal sequence-specific DNA binding polypeptide-target sequence pairs. In some embodiments, sequence entropy, also sometimes known as a "Shannon information entropy," is used in analysis of target DNA sequences, e.g., when polypeptides bind to more than one target DNA sequence. The more sequences to which a polypeptide binds, the higher the information entropy. This type of analysis provides a quantitative method to measure the percent overlap between the target DNA sequences to which two polypeptides bind. A higher joint information entropy means that there are more sequences to which two polypeptides can bind. In graph theory, the polypeptides are "nodes" and the "edges" are how close they are (e.g., a measured by their different binding sequences). In some embodiments, algorithms, including but not limited to, graph partitioning algorithms, can be used to identify the largest connected network of nodes. In some embodiments, a graph partitioning algorithm, k-means clustering, position weight matrices, hidden markov models, neural networks, or other algorithms are employed. These algorithms maybe performed by a processor executing instructions encoded on a computer-readable storage medium.

Ultimately, a set of orthogonal cognate sequence-specific DNA binding polypeptide-target DNA sequence pairs are provided. The set of orthogonal pairs can then be used as "tools" to generate a genetic circuit as desired.

In some embodiments, control elements adapted for a particular host cell can be used in host cells derived from other species. In other embodiments, some or all of the control elements may not be optimized for use in a second host cell. In such cases, standardized assays as described herein can be used to identify control elements for the second host cell.

VII. Design of Genetic Circuits

Genetic circuits are comprised of an array of logic gates that process one or more input signals, process the input, and generate an output according to a logic design. Generation of logic gates can be generated using expression cassettes that respond to biological inputs, wherein the expression cassettes are regulated using combinations of repressors and activators. A variety of logic gates using such expression cassettes have been described. See, Tamsir et al., Nature, 469(7329): 212-215 (2011). The genetic circuit can function as, for example, a switch, oscillator, pulse generator, latch, flip-flop, feedforward loop, or feedback loop.

The term "gate" is used to refer to a device or molecular mechanism that produces a particular (predetermined) output in response to one or more inputs. Thus, for example, an AND gate produces a HIGH output only when all inputs are HIGH. An OR gate produces a HIGH output when any input is HIGH and a LOW output only when all inputs are LOW. A NOT function returns a HIGH when input is LOW and a LOW when input is HIGH. Logic Gates and their uses are well known to those of skill in the art (see, e.g. Horowitz and Hill (1990) The Art of Electronics, Cambridge University Press, Cambridge). In some embodiments, the genetic circuits generated from the identified set of orthogonal pairs comprise 1, 2, 3, 4, 5, 6, 7, 8, 9 or more logic gates. Exemplary logic gates include, e.g., AND, NAND, NOR, OR, NOT, XOR, EQUALS, AND, IMPLIES, and ANDN gates. For example, NOR gates can comprise a transcriptional repressors and a transcriptional repressor target DNA sequence. AND gates can comprise a transcriptional activator and a transcriptional activator target DNA sequence.

In some embodiments, a genetic circuit is designed with the aid of an algorithm. For example, a logic minimization algorithm can be used to identify the minimum number of parts (e.g., repressors, activators, operators, etc.) for achievement a particular logic circuit. Algorithms may be performed by a processor by executing instructions encoded on a computer-executable storage medium. An exemplary algorithm can be in a VLSI design, for example the ESPRESSO program. See, e.g., Rudell, R L: *Multiple-Valued Logic Minimization for PLA Synthesis*. Berkeley, Calif.: UC-Berkeley; 1986. In some embodiments, The output of the logic minimization tool feeds into programs, such as Logic Friday (e.g., Wu Y, et al. Nature 461:104-108 (2009)), which act as a visualization tool and enable constraints to be applied to the construction of a circuit diagram. See, Clancy and Voigt, *Current Opinion in Biotechnology* 21:1-10 (2010). In some embodiments, the genetic circuit is determined using a hardware descriptive language. In some embodiments, the hardware descriptive language is VHDL or Verilog.

Once a genetic circuit is designed and implemented, the genetic circuit can be tested by challenging the circuit with a variety of inputs to confirm that the expected outputs are generated. This can assist to confirm that no unintended interactions occur within the genetic circuit or between the genetic circuit and the host cell in which the genetic circuit is expressed.

VIII. Computer Implemented Methods

Embodiments of the invention as described above can be implemented in the form of control logic using hardware and/or using computer software, firmware, or combinations thereof, in a modular or integrated manner. For example, the logic minimization methods for determining the genetic circuit, sequence similarity algorithms, and motif finding algorithms, can be implemented via the various forms above. Based on the disclosure and teachings provided herein, a person of ordinary skill in the art will know and appreciate other ways and/or methods to implement the present invention using hardware and a combination of hardware and software.

Computing system 700 can include one or more processors, such as a processor 704. Processor 704 can be implemented using a general or special purpose processing engine such as, for example, a microprocessor, controller or other control logic. In this example, processor 704 is connected to a bus 702 or other communication medium.

Memory 706 (which may be organized as a database) can store the classification information (e.g., functional roles and activities) of the sequences and assay data used to design the genetic circuit. Any data mentioned herein (e.g., classification information) can be downloaded from remote memory (e.g., from a network drive or a server that can be considered to be part of the computer system) and stored in a local memory that is more quickly accessible to a processor on which certain steps of methods are being implemented. Conversely, data generated by such a processor can be uploaded to the remote memory.

Further, it should be appreciated that a computing system 700 of FIG. 22 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 700 can include a conventional network system including a client/server environment and one or more database servers, distributed networks, or integration with LIS/LIMS infrastructure. A number of conventional network systems, including a local area network (LAN) or a wide area network (WAN), and including wireless and/or wired components, are known in the art. Additionally, client/server environments, distributed systems, database servers, and networks are well documented in the art.

Computing system 700 may include bus 702 or other communication mechanism for communicating information, and processor 704] coupled with bus 702 for processing information.

Computing system 700 also includes a memory 706, which can be a random access memory (RAM) or other dynamic memory, coupled to bus 702 for storing instructions to be executed by processor 704. The instructions may include instructions for performing methods of embodiments described herein. Memory 706 also may be used for storing temporary variables or other intermediate information during execution of instructions to be executed by processor 704. Computing system 700 further includes a read only memory (ROM) [708] or other static storage device coupled to bus 702 for storing static information and instructions for processor 704.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Computing system 700 may also include a storage device 710, such as a magnetic disk, optical disk, or solid state drive (SSD) is provided and coupled to bus 702 for storing information and instructions. Storage device 710 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 710 may include other similar instrumentalities for allowing computer programs or other instructions or data to be loaded into computing system 700. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 710 to computing system 700.

Computing system 700 can also include a communications interface 718. Communications interface 718 can be used to allow software and data to be transferred between computing system 700 and external devices. Examples of communications interface 718 can include a modem, a network interface (such as an Ethernet or other NIC card), a communications port (such as for example, a USB port, a RS-232C serial port), a PCMCIA slot and card, Bluetooth, etc. Software and data transferred via communications interface 718 are in the form of signals which can be electronic, electromagnetic, optical or other signals capable of being received by communications interface 718. These signals may be transmitted and received by communications interface 718 via a channel such as a wireless medium, wire or cable, fiber optics, or other communications medium. Some examples of a channel include a phone line, a cellular phone link, an RF link, a network interface, a local or wide area network, and other communications channels.

Computing system 700 may be coupled via bus 702 to a display 712, such as a cathode ray tube (CRT) or liquid crystal display (LCD), for displaying information to a computer user. An input device 714, including alphanumeric and other keys, is coupled to bus 702 for communicating information and command selections to processor 704, for example. An input device may also be a display, such as an LCD display, configured with touchscreen input capabilities.

Execution of the sequences of instructions contained in memory [706] causes processor [704] to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" as used herein generally refers to any media that is involved in providing one or more sequences or one or more instructions to processor 704 for execution. Such instructions, generally referred to as "computer program code" (which may be grouped in the form of computer programs or other groupings), when executed, enable the computing system 700 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 710. Volatile media includes dynamic memory, such as memory 706. Transmission media includes coaxial cables, copper wire, and fiber optics, including the wires that comprise bus 702. A computer product can be or include the computer-readable medium. For example, a computer product can be a computer system that includes one or more processors and a computer readable medium that has instructions for controlling the one or more processors to perform any of the methods described herein.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 704 for execution. For example, the instructions may initially be carried on magnetic disk of a remote computer. The remote computer can load the instructions into its dynamic memory and send the instructions over a network. The instructions received by memory 706 may optionally be stored on storage device 710 either before or after execution by processor 704.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

IX. Computational Implementation of Genetic Circuit Design

Genetic Element Data & Data Models

Much of biological data is reported in a standardized way. Many of these data formats support an implicit data model, facilitating understanding of the data by humans and use of that data in computational analysis. In this embodiment, genetic element data may represent a standardized way for reporting and transferring data. The implicit data model will include a standardized representation of basic information. Genetic element data may contain a standardized representation of classification data which provides identification of functional regions of the sequence, as well as the functional description of that sequence. Finally, genetic element data may provide a standardized classification of the experimental characterization information associated with the part. In some embodiments, genetic element data can be added, removed, modified or updated over time. Genetic element data may be updated on a server and downloaded locally.

Classification of Genetic Design Elements, Devices and Circuits

Genetic element data can be characterized using standardized terms, such as the features seen in GenBank records. Such terms can be used automation systems based upon controlled vocabularies, or ontology based terms.

Characterization Based Upon Experimental Measurements

Performance of a genetic design element, device or genetic circuit can be based upon use of measurement data. Meta data associated with a given assay can be used to classify the types of experimental investigations performed upon the element. Raw data can be reported managed, and stored in a standardized format. This in turn permits the comparison of elements that have gone through similar experimental investigations and provides a means to use data from several such investigations as a way to sort, filter, compare and select elements with appropriate performance characteristics for genetic circuit design.

Development and Use of Design Template

A design template is a general solution to a design problem that recurs repeatedly in many projects. Software designers adapt the template solution to their specific project. Templates use a formal approach to describing a design problem, its proposed solution, and any other factors that might affect the problem or the solution. A successful template should have established itself as leading to a good solution in three previous projects or situations.

In embodiments described herein, design templates can be developed from genetic element data in order to identify genetic circuit elements, devices and genetic circuits that have certain characteristics. Such characteristics can be annotated through use of ontology or controlled vocabulary terms. According to embodiments described herein, designs can be searched and identified and reused or modified to suit the purposes of new designs. The corresponding DNA sequences can be identified and experimental manipulations can be performed upon them to introduce new desired functionality.

Computer Aided Design Algorithms

According to various embodiments, genetic circuit elements may be classified and characterized and their data stored. This may permit the data to be used in a genetic compiler program. A genetic compiler program is a software program, computer executable instructions, that may allow a system to use genetic circuit element data to design, develop, verify and validate genetic circuits. The types of algorithms supporting a design methodology used in such a genetic compiler program may include the following steps:

Receiving the specification of genetic circuits based upon desired inputs and resultant outcomes, the identification of design constraints or requirements affecting that specification.

Design of the processing of the inputs to result in desired outcomes.

Analysis and design for orthogonality checks between the circuit design elements, the proposed devices, the proposed genetic circuit and the proposed target genome.

Identification and compositional arrangement of appropriate genetic circuit elements.

Assembly and Experimental verification and validation of the design.

According to various embodiments described herein, the design process is an interactive process, supporting simultaneous development of similar solutions for desired performance characteristics.

Development of Standardized Assays

According to various embodiments described herein characterization of genetic circuit elements, devices and genetic circuits may be through use of standardized assays, designed to measure the performance of an identified element as compared to a set of variant elements. Description of such experiments will be encoded in a standardized fashion for use in the software.

Orthogonality & Interaction Checks for Computational Designs

According to various embodiments described herein, data may be collected to identify possible design constraints during device and genetic circuit design and development. In some embodiments, this may include checks for genetic element design, development and usage. In some embodiments, this may include checks for device design, development and usage. In some embodiments, this may include checks for genetic circuit design, development and usage. In some embodiments, this may include checks for genetic circuit element, device and genetic circuit, development and usage within identified hosts. In some embodiments this will include checks for genetic circuit element, device and genetic circuit, development and usage within identified populations of hosts.

Assembly, Validation & Verification of Computational Designs

According to various embodiments described herein, data may be collected to identify possible design constraints during device and genetic circuit assembly, validation and verification. In some embodiments, this may include checks for assembly constraints. In some embodiments this may include checks for verification constraints. In some embodiments, this may include checks for validation constraints.

Modeling & Simulation

According to various embodiments described herein, data may be collected to identify possible functioning of the genetic circuit element, device or genetic circuit. This data may be used to demonstrate the functioning of the design during modeling. Models may be used to query the performance of the design under different condition during simulations.

Incorporation of Performance Data into Models & Simulations

According to various embodiments described herein, data may be collected to identify the actual performance of the genetic circuit element, device or genetic circuit in the host system. As described in the section for assay standardization, performance data may be collected and reported for use in a computer analysis in a standardized fashion. This data may be used to demonstrate the actual functioning of the design as compared to predicted functioning of the device during modeling. Models may be used to query the actual performance of the design as compared to the predicted performance of the device under different conditions during simulations.

EXAMPLES

The following examples are offered to illustrate, but not to limit the claimed invention.

Example 1. Orthogonal Sigmas for Programmable Transcriptional Regulation

Engineering synthetic gene circuits requires a library of "parts" that serve to regulate gene expression and can be reliably combined together to build complex programs (see, Voigt, C. A., Curr. Opin. Biotechnol., 17(5): 548-57, (2006)). Promoters are an essential "part" that control gene expression by regulating the rate of mRNA production. Large genetic circuits require many promoters that can be individually controlled. This enables conditional control of gene expression across a circuit and requires a library of orthogonal promoter systems in which regulators target specific promoters with no cross-talk across the circuit.

Figure 1:
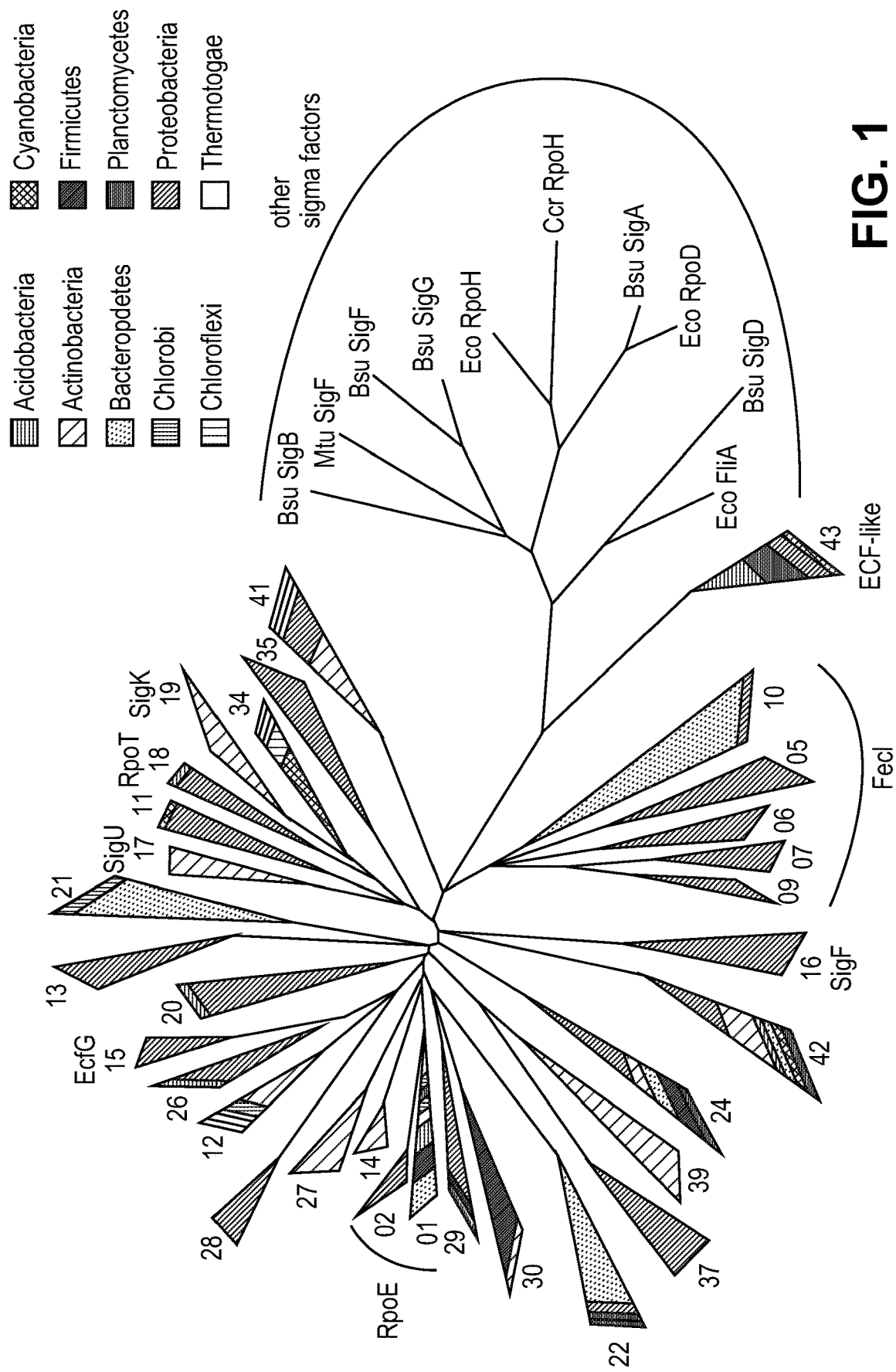
FIG. 1 is a diagram illustrating the phylogenetic tree of ECF σs. ECF σs have been classified into 43 groups (32 shown in FIG. 1) based on their amino acid sequence. Each clade is color coded according to the phylogenetic distribution of the ECF σ factors. Figure taken from Staron, A., H. J. Sofia, et al.

To achieve orthogonal regulation, we are using sigma (σ) factors to construct orthogonal σ-promoter systems. Sigma factors recruit RNA polymerase (RNAP) to specific promoter sequences to initiate transcription. The σ 70 family consist of 4 groups: Group 1 are the housekeeping σs and are essential; Groups 2-4 are alternative σs that direct cellular transcription for specialized needs (see, Gruber, T. M. and C. A. Gross, Annu. Rev. Microbiol., 57: 441-66, (2003)). Group 4 σs (also known as ECF σs; extracytoplasmic function) constitute the largest and most diverse group of σs, and have been classified into 43 subgroups (FIG. 1; see, Staron, A., H. J. Sofia, et al., Mol. Microbiol., 74(3): 557-1, (2009)). Each subgroup is thought to recognize different promoter sequences, making these σs ideal for constructing orthogonal σ-promoter systems. We have constructed a library of ECF σs that can be expressed in E. coli and are using both computational and experimental methods to identify promoter sequences and demonstrate orthogonal regulation.

A. Constructing the ECF Sigma Library

The ECF σ library was constructed as follows: 2 σ candidates were selected from each ECF subgroup (FIG. 1) to maximize promoter diversity to create a library of 86 σs (Table 1). Each candidate was chosen from an organism closely related to E. coli to maximize the likelihood of the functionally binding to E. coli RNAP (note σ-RNAP interactions are highly conserved and σs from Bacillus subtilis have been shown to function with E. coli RNAP). Where possible, σs were selected that have a known cognate anti-σ. These are specific negative regulators of σs, thereby increasing the regulatory utility of each σ for engineering genetic circuits. For each σ the DNA coding sequences were refactored and codon optimized for E. coli by Geneart. DNA fragments were synthesized by Geneart containing the refactored coding sequences with the flanking restriction sites Nde I overlapping the start codon (CAT<u>ATG</u>; Nde I site with start codon underlined) and a Bam HI and Hind III site immediately downstream of the TAA stop codon. The synthesized DNA fragments were cloned on Nde I-Hind III sites in to a pET21a-derived expression vector (Novagen) enabling the σ genes to be expressed from a T7 promoter. In the vector the genes were cloned in-frame and downstream of an N-terminal His6 (SEQ ID NO:140) tag coding sequence with a cleavable PreScission protease cleavage site to enable protein purification. Thus, all σs in our library contain the additional N-terminal sequence: MGSSHHHHHHSSGLEVLFQGPH (SEQ ID NO:141) (PreScission protease cleavage site underlined).

B. Expressing the ECF Sigma Library and Measuring Toxicity in *E. coli* Host

Figure 2:
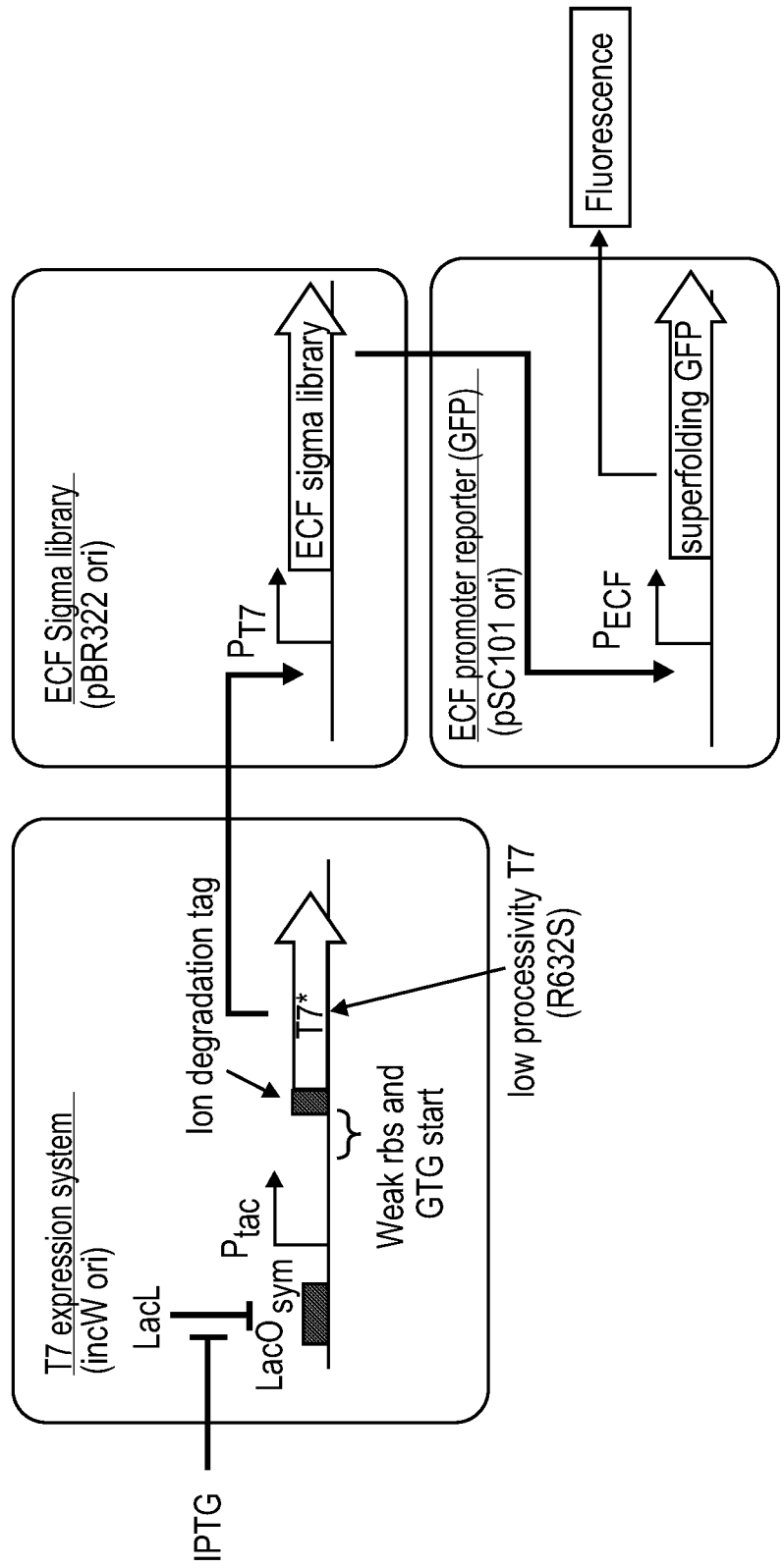
FIG. 2 is a diagram illustrating the three-plasmid expression system to enable controlled induction of ECF σs and measurement of target promoter activity

Expression of the ECF σ library was monitored using a 3 plasmid system encoding a T7 expression system, ECF σ library, and target promoter reporter transformed in DH10b cells (see, FIG. 2). The T7 expression system is encoded on a low copy plasmid (pN565; incW ori: K. Temme) and is tightly regulated using a Ptae promoter containing a symmetrical Lac operator (lacO$_{sym}$). This enables a tight OFF state when uninduced, and graded T7 induction with IPTG. The T7 gene encodes a modified non-toxic form of T7 RNAP that has a low processivity substitution (R632S), an N-terminal Lon degradation tag, and is weakly expressed using the low activity GTG start codon and a weak ribosome binding site. The ECF σs are individually carried on derivatives of the T7 expression vector, pET21a (pBR322 ori). The ECF promoter reporter vector (low copy, pSC101 ori), carries ECF-specific promoters fused to a superfolding gfp reporter, enabling fluorescent measurements of a activity.

Figure 3:
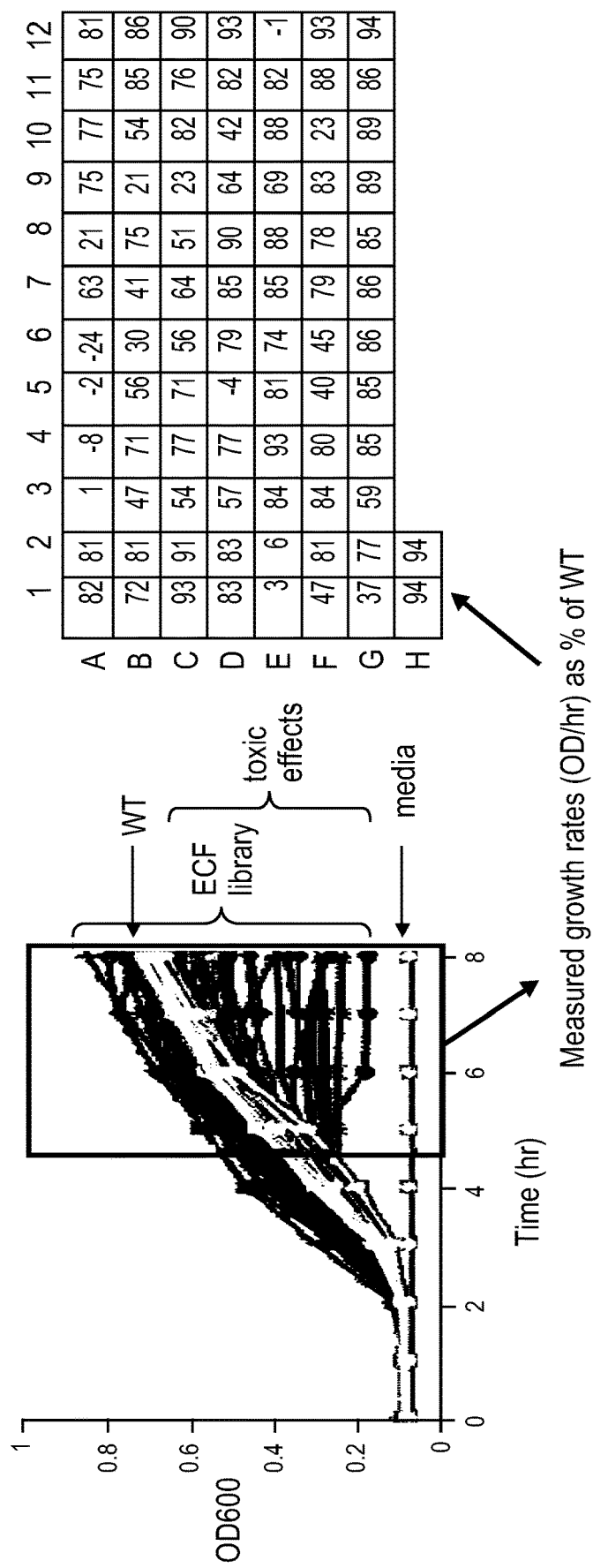
FIG. 3 illustrates the growth rates of strains over-expressing the ECF σ library in 96-well format.

Only small numbers of a molecules (~100s) are required in a cell to observe gene expression; however, expression of foreign proteins in *E. coli* can be toxic. Sigmas may be toxic due to erroneous gene expression or by binding strongly to RNA polymerase, preventing gene expression by host σs. Toxicity was determined by measuring the changes in growth rate from over-expressing each member of the ECF σ library in DH10b host *E. coli* cells assayed in 96-well format both in exponentially growing cultures and colony sizes on agar plates. FIG. 3 (left side) illustrates typical growth plots of DH10b strains carrying different ECF σs after high induction (100 μM IPTG) for 8 hrs in LB at 37° C. shaking in 96-well plates at 480 rpm, 6 mm diameter, in a Varioskan 96-well plate reader. Over-expression of only 15% of σs in our library result in large growth defects, similar results are observed on colony sizes on agar plates (data not shown).

C. Identifying Target Promoters

Figure 4:
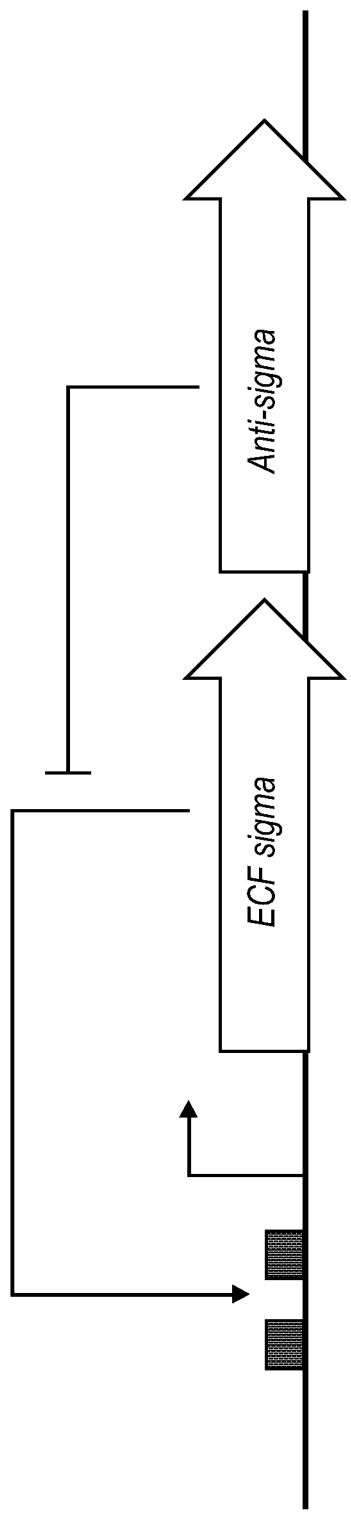
FIG. 4 is an illustration of the autoregulation of many ECF σs by an upstream promoter.
Figure 5A:
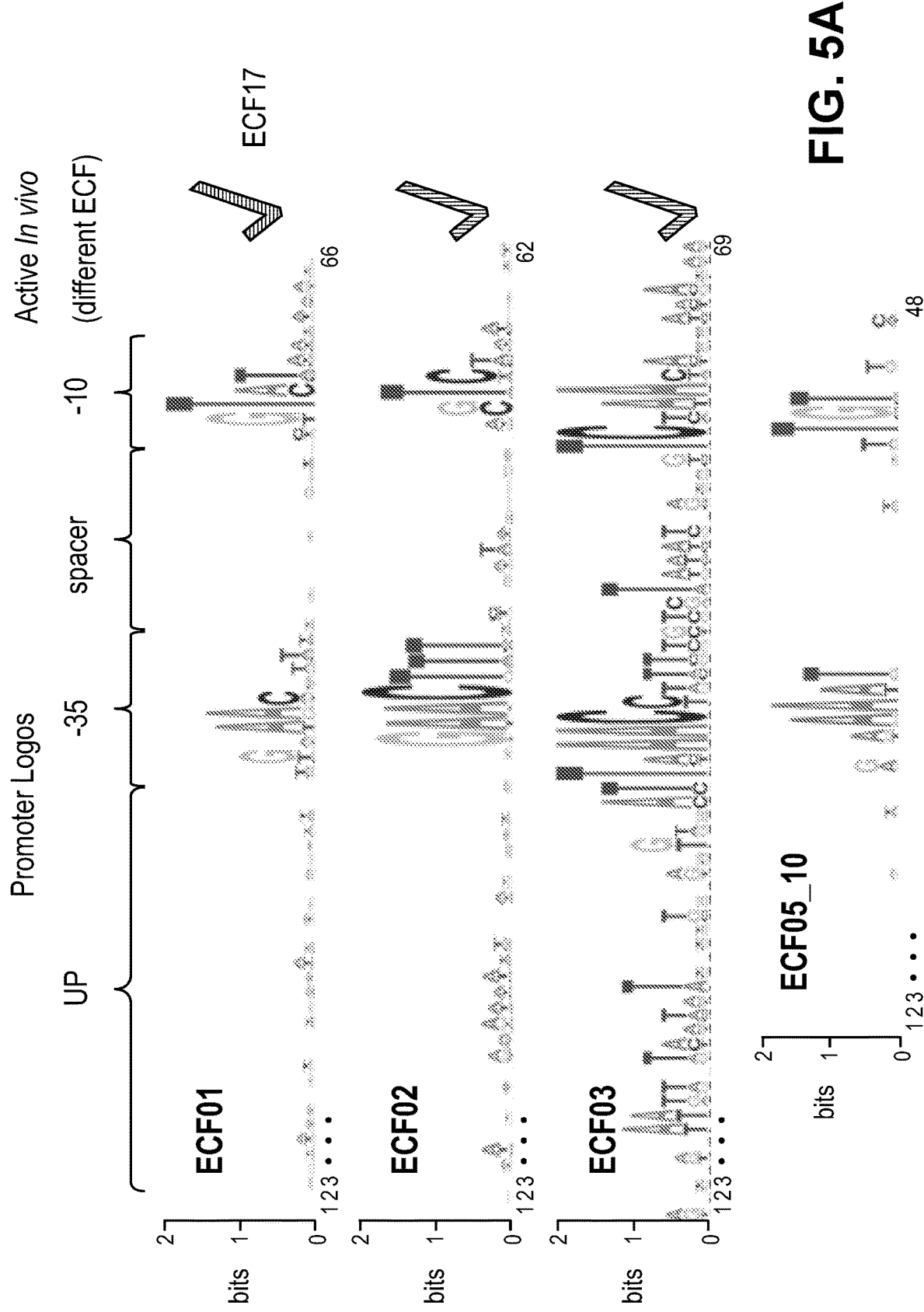
FIGS. 5A-5H illustrate sequence logos of promoters found upstream of 34 ECF σ subgroups (SEQ ID NOS:1-29). For each sequence logo, the key promoter motifs (UP, -35, spacer, -10) are indicated. Promoters shown to be functional in vivo are indicated by a tick mark: a tick followed by an ECF designation indicates the promoter could only be activated by a sigma from another subgroup.
Figure 5B:
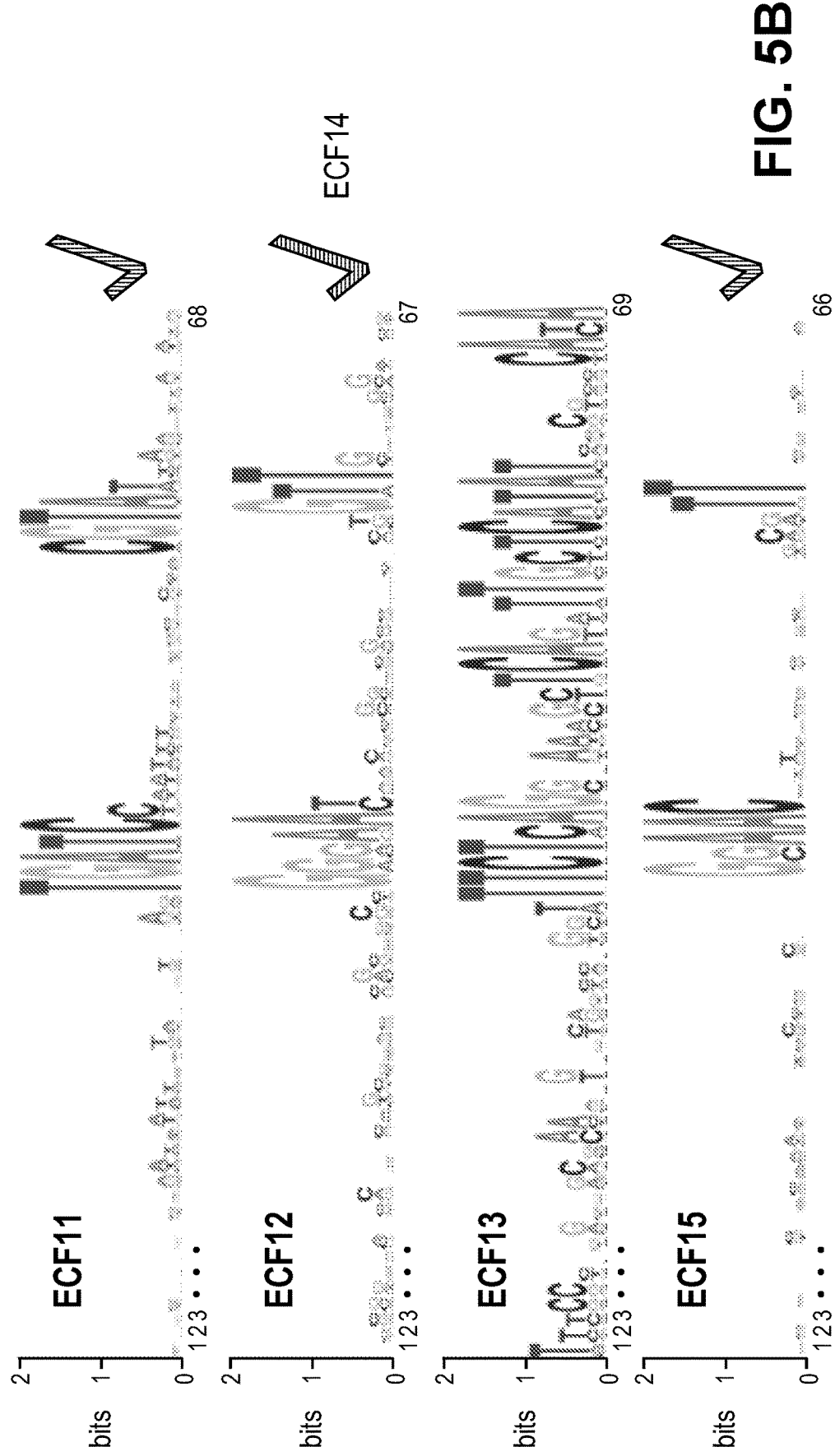
Figure 5C:
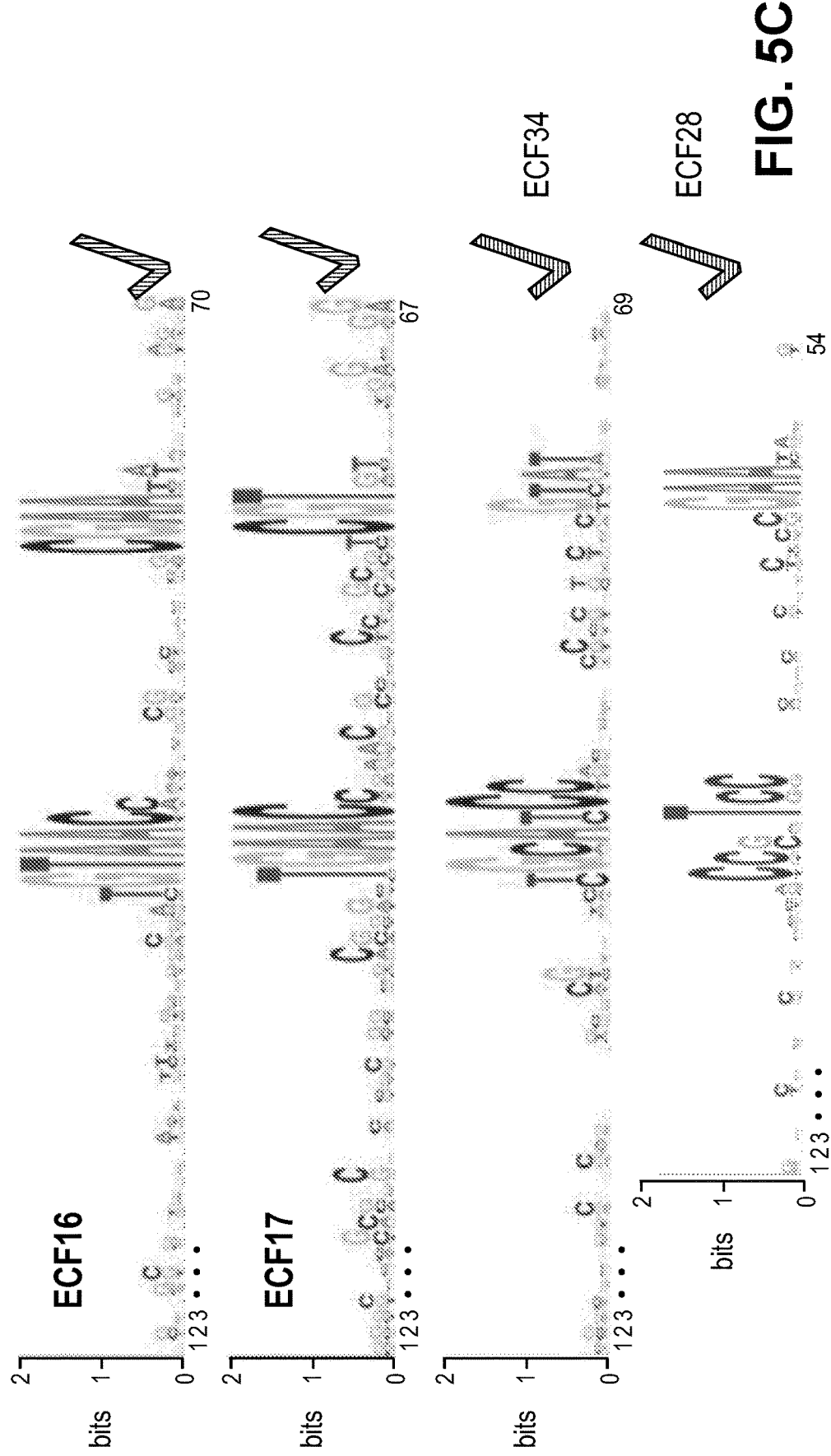
Figure 5D:
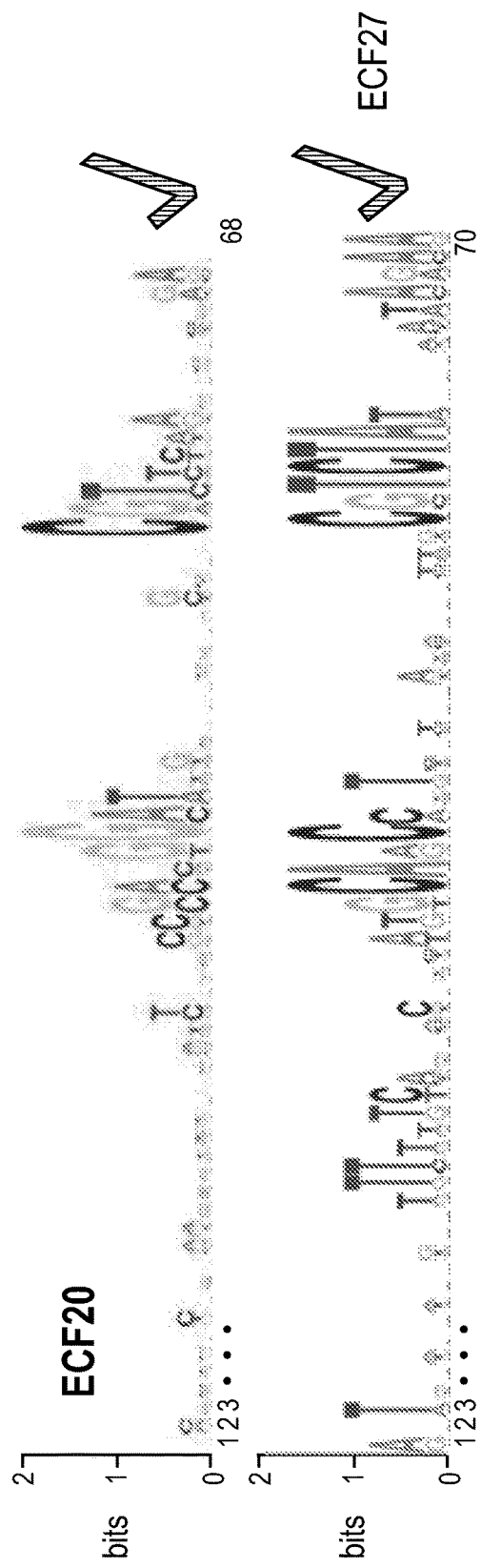
Figure 5E:
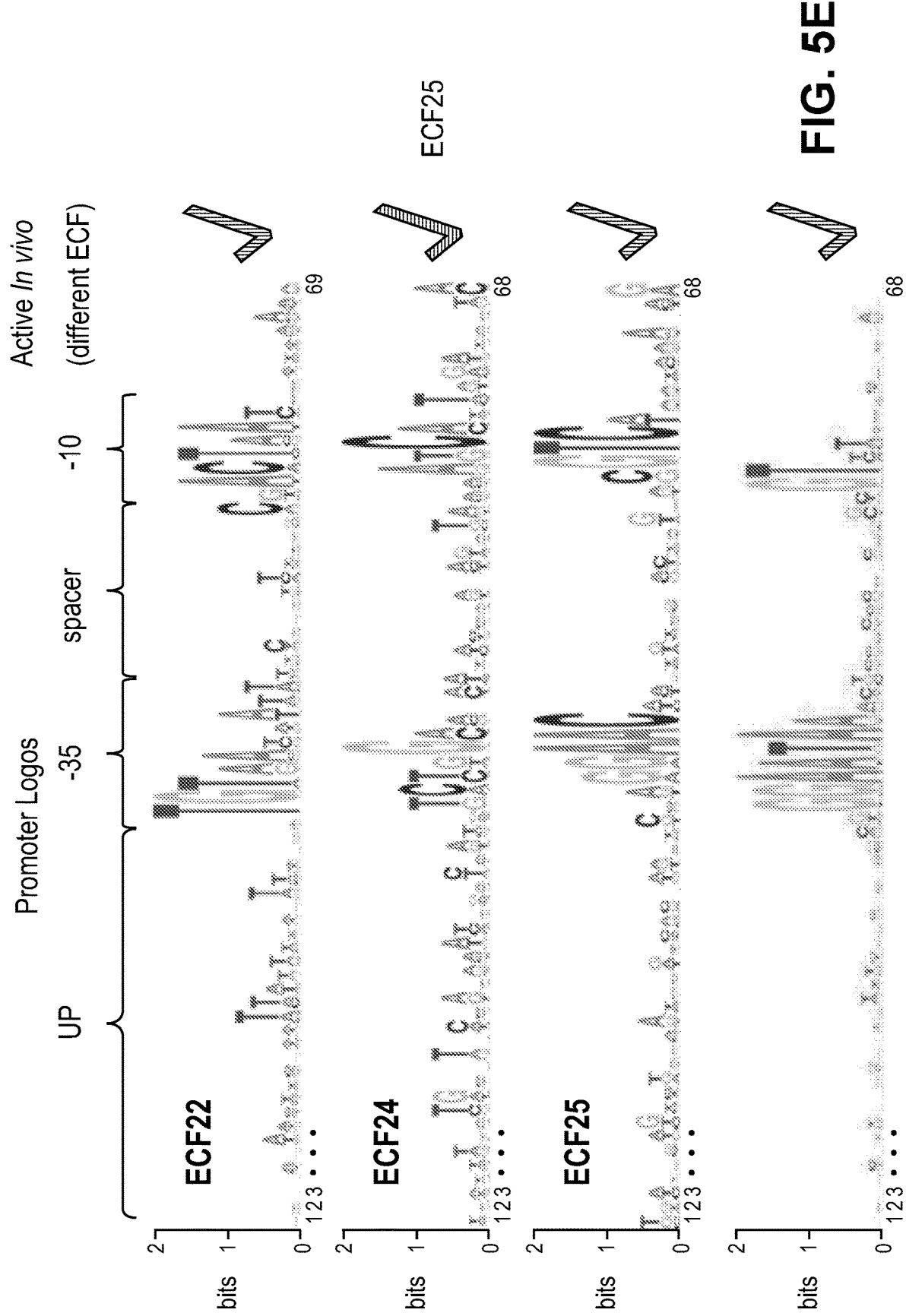
Figure 5F:
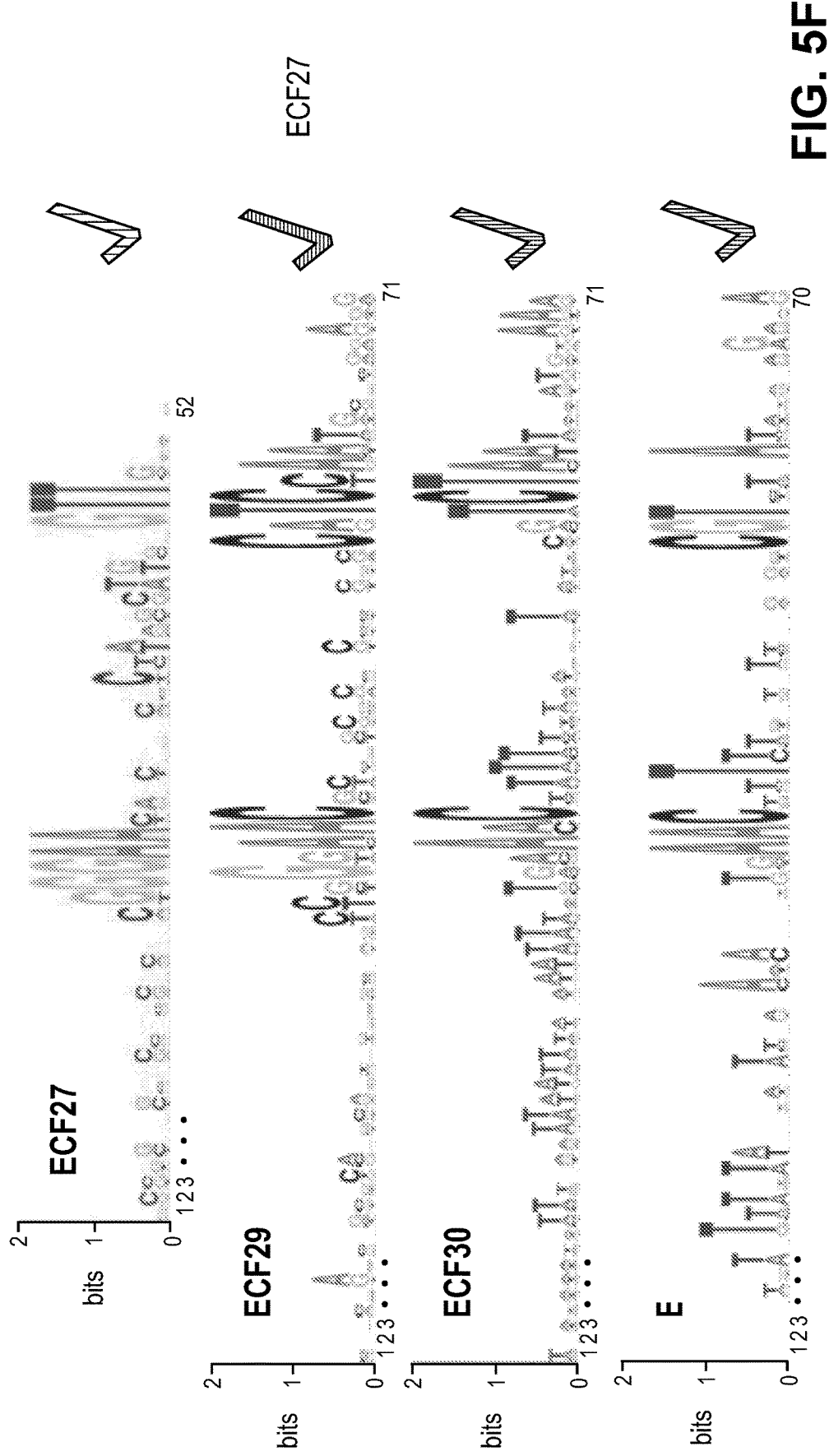
Figure 5G:
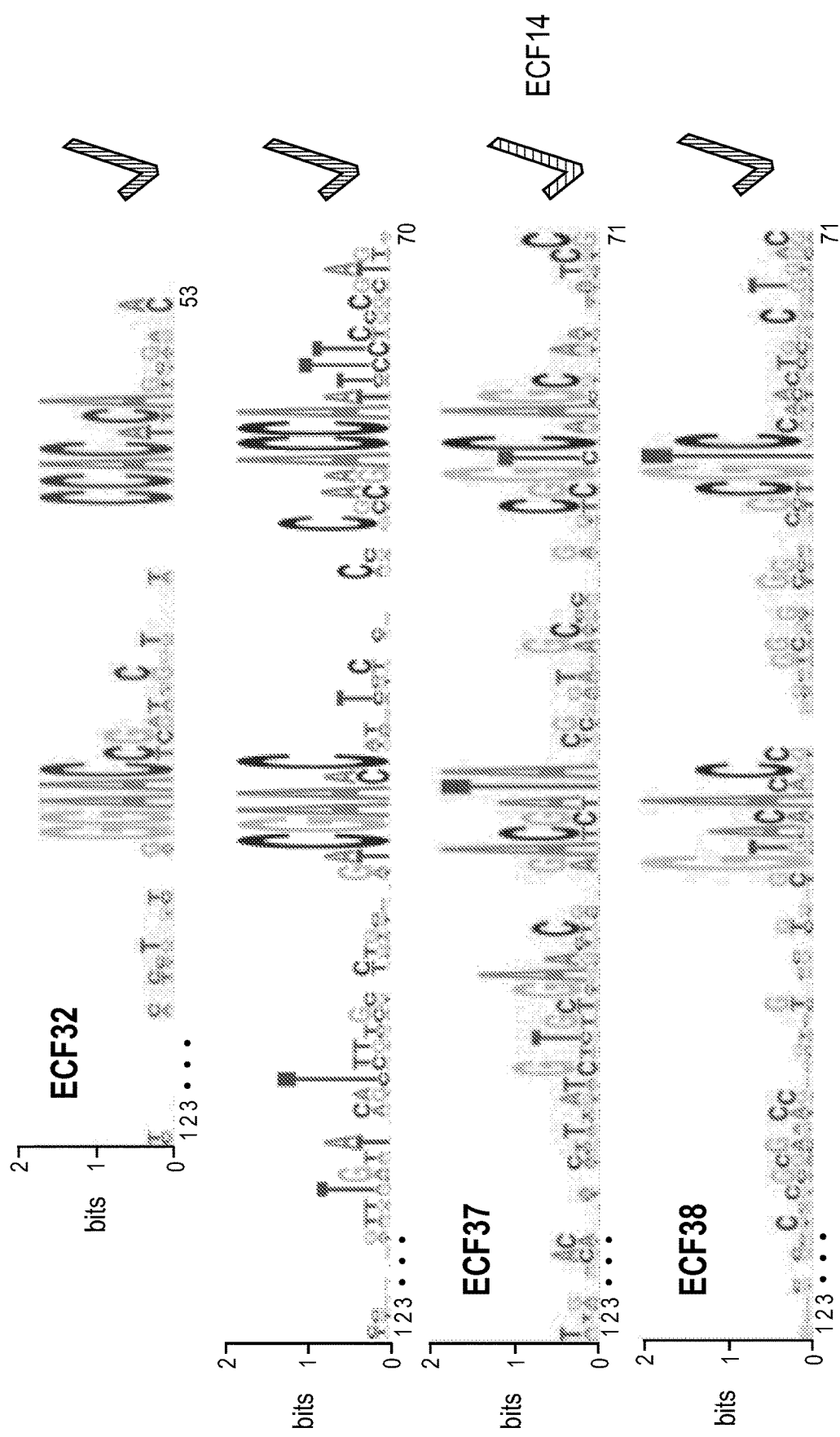
Figure 5H:
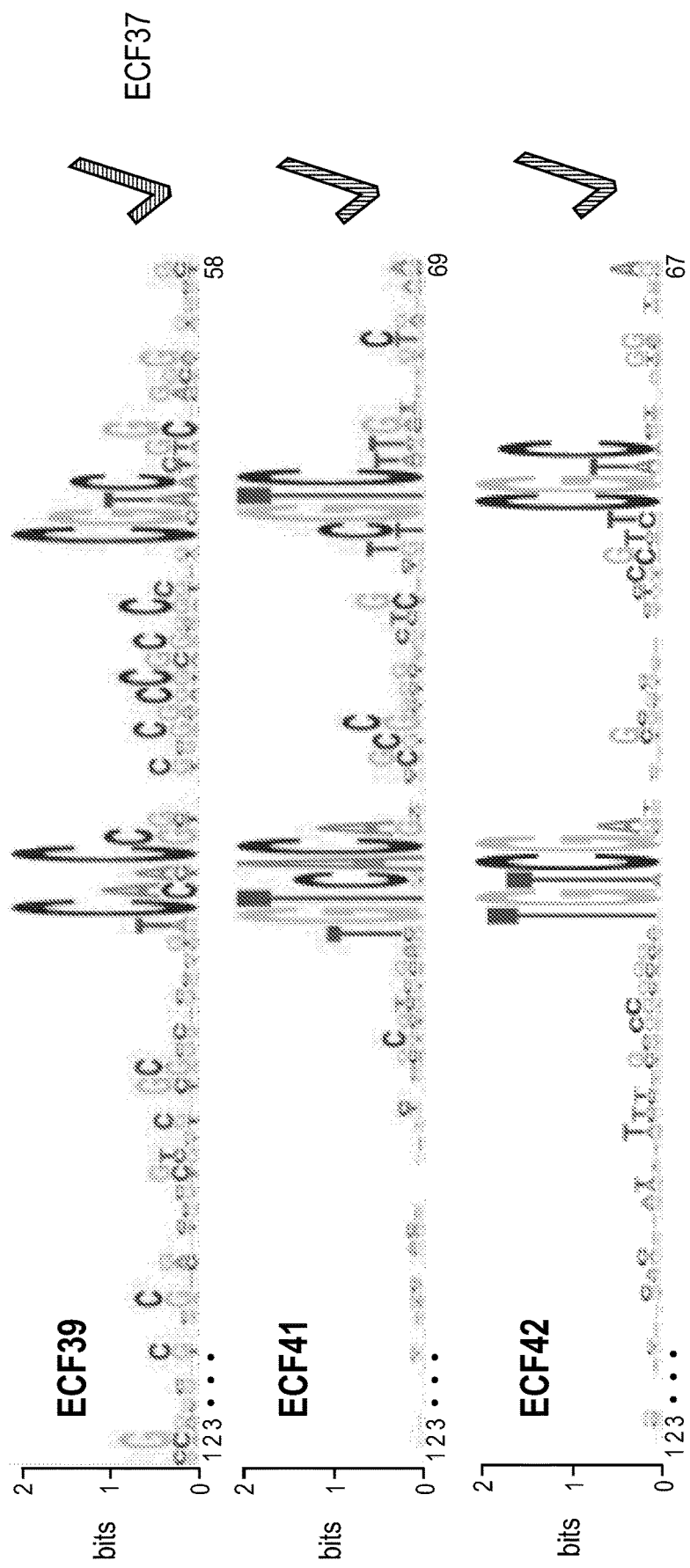

Many ECF σs autoregulate their own gene expression (FIG. 4). Since each ECF σ subgroup is thought to recognize different promoter sequences, promoters can be found by searching upstream of a genes within each subgroup for conserved motifs. Promoters have been identified for 13 subgroups (see, Staron, A., H. J. Sofia, et al., *Mol. Microbiol.*, 74(3): 557-1, (2009)); computational searches are in progress to identify promoter motifs for the remaining subgroups. The currently identified promoter sequences have been used to construct promoter models in which the key -10 and -35 promoter motifs are defined using two-block motif searcher, BioProspector (see, Liu, X., D. L. Brutlag, et al., *Pac. Symp. Biocomput.*, 2001: 127-38, (2001)) and the variable length spacing between the motifs quantified using histograms (FIGS. 5A-5H).

D. Predicting Promoter Orthogonality

The 34 promoter models were used to predict whether σs from the different ECF subgroups were able to recognize promoters from another subgroup (cross-talk) or if they were specific to just their own subgroup (orthogonal). For promoters from each subgroup, scoring models were constructed as described in Rhodius, V. A. & V. K. Mutalik, *Proc Natl. Acad. Sci. U.S.A.*, 107(7):2854-9, (2010) using Position Weight Matrices (PWMs) for the -35 and -10 motifs, and a penalty term for suboptimal distances between the -35/-10 motifs:

Score=PWM$_{-35}$+PWM$_{-10}$+spacer penalties

This model can then be used to "score" promoter sequences: the resultant score has been shown to be proportional to promoter strength (rate of mRNA production) (Rhodius, V. A. & V. K. Mutalik, *Proc Natl. Acad. Sci. U.S.A.*, 107(7):2854-9, (2010)), i.e.

Score ∝ log(promoter strength)

Figure 6:
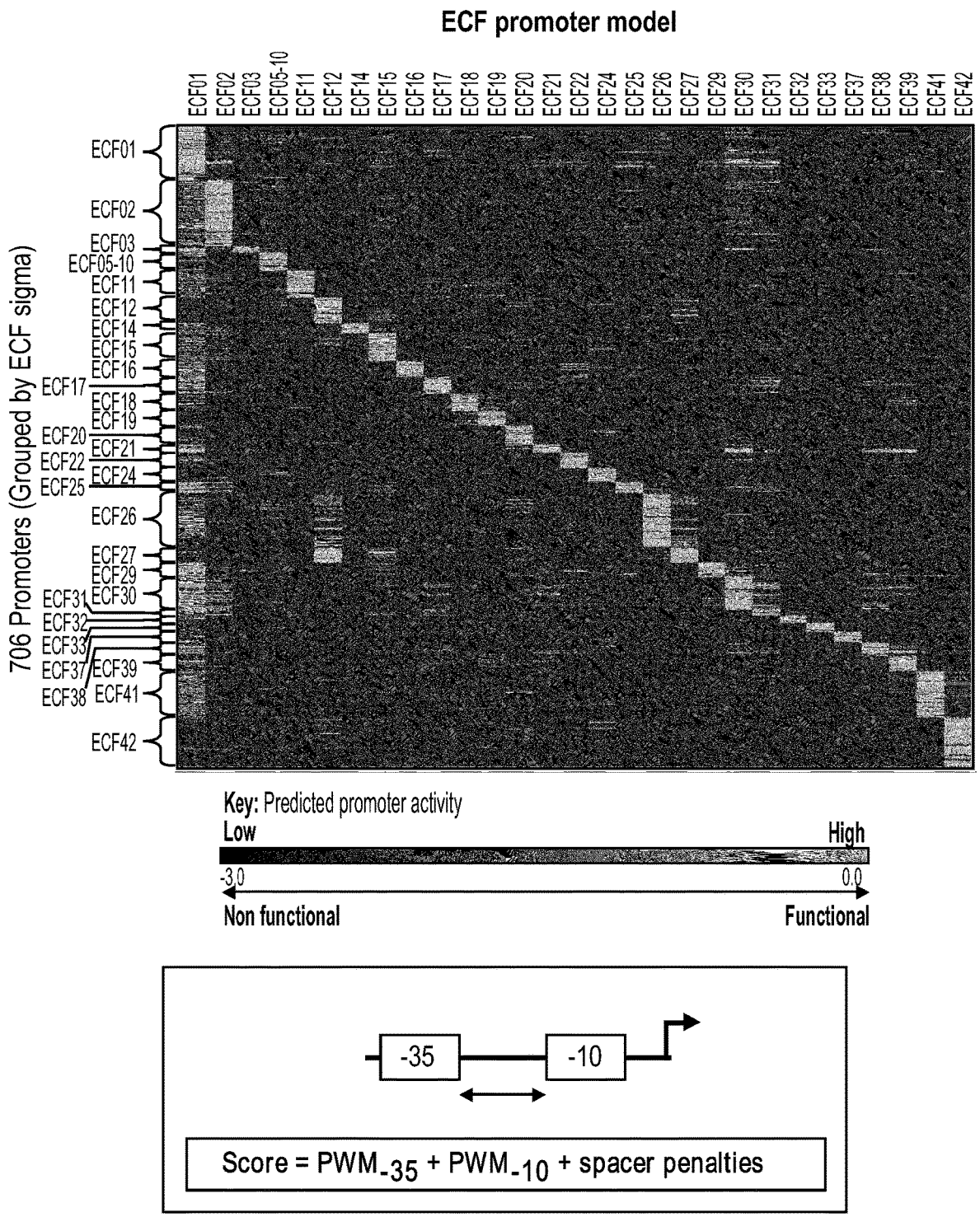
FIG. 6 Heatmap of predicted promoter activity with different ECF σs. 706 promoters (vertical axis) were score by promoter models for each ECF σs (horizontal axis). Predicted promoter activity is displayed as a sliding black to green scale (shown here in grayscale), where green (lighter) indicates active and black inactive (non-functional).

The 34 promoter scoring models were used to score 706 promoter sequences from all 34 ECF σs to predict specificity of promoter recognition. We find that in general the σs are highly specific, mainly recognizing promoters from their own subgroup (FIG. 6)

E. Testing Sigma-Promoter Orthogonality

Figure 7:
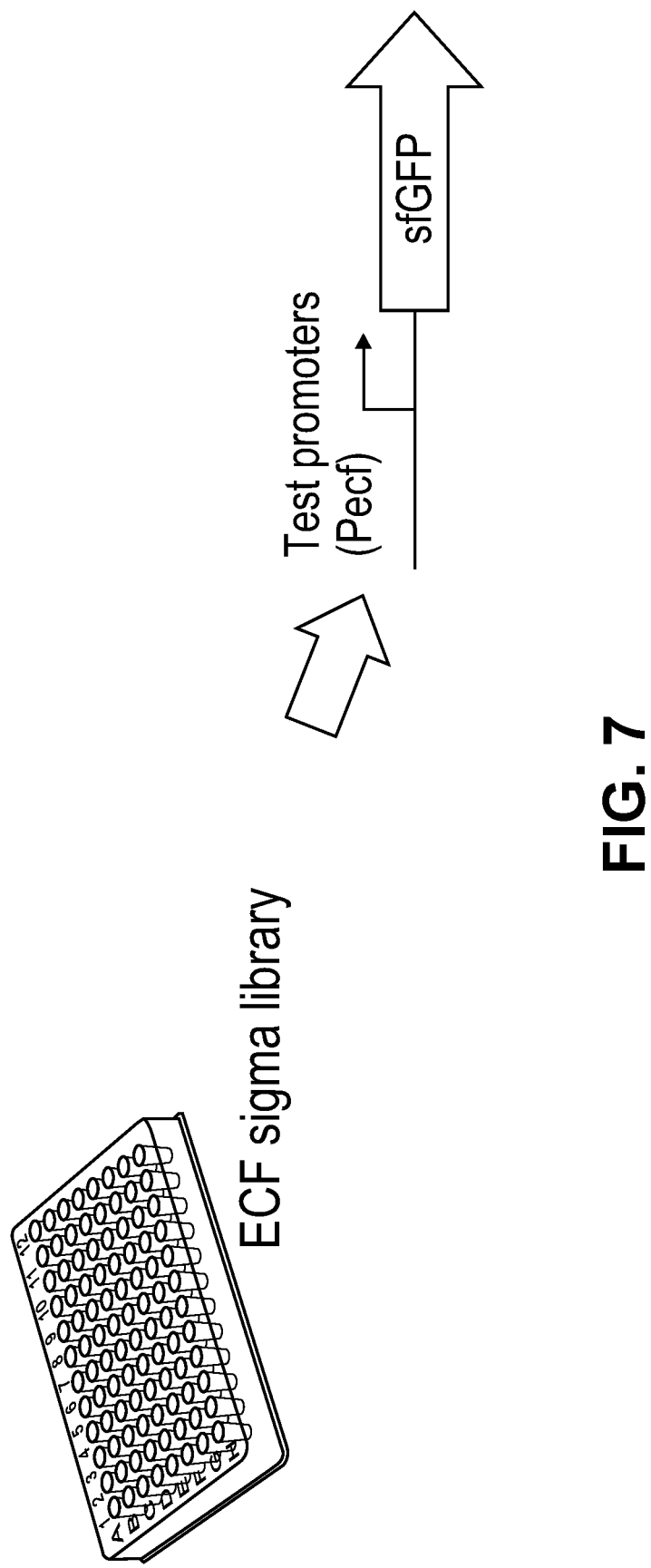
FIG. 7 illustrates in vivo screening of ECF σ library in 96-well format against candidate promoters fused to super-folding GFP.

Next, we tested the orthogonality of the ECF σ-promoter pairs. Using our promoter scoring models to predict orthogonal promoters, for each ECF σ subgroup we constructed candidate promoters fused to gfp. Each promoter was then screened in vivo against the entire ECF σ library in 96-well format using our σ expression system to measure promoter activity (see FIGS. 2 and 7).

Figure 8:
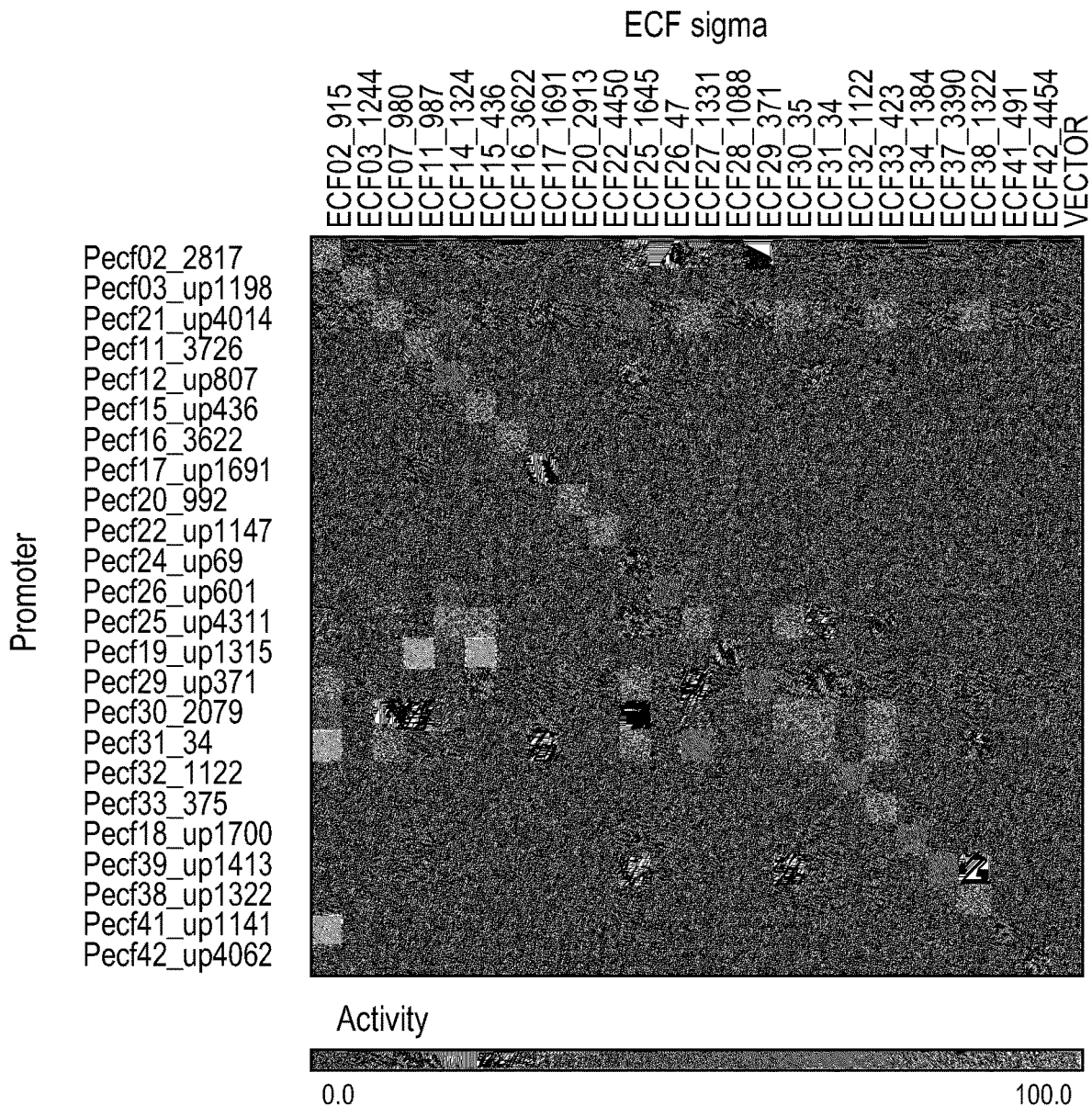
FIG. 8 illustrates a heatmap of in vivo promoter activities against ECF σs. Only the most active and orthogonal σ-promoter pairs are illustrated.

Using this approach we identified 24 orthogonal σ-promoter systems (FIG. 8). Functional promoters are listed in the Table below. Our results show that the ECF σs are highly orthogonal with the σs very specific to their cognate promoter, making them ideal orthogonal regulators.

Sequence of functional ECF promoters from -60 to +20. The core -35 and -10 motifs are underlined.

```
Promoter      Sequence (-60 to +20) (SEQ ID NOS: 221-244)

Pecf02_2817   CATGACAAACAAAAACAGATGCGTTACGGAACTTTACAAAAACGAGACACTCTAACCCTTTGCTTGCTCAAATTGCAGCT Pecf03_UP1198 CAGTACAAAATTTTTAGATGCGTTTTTAACTTCGTTCCTTTTCGGCGTTCTAATAACCAAAGCTCAGAAATAATAGATG Pecf11_3726   ATGCCTCCACACCGCTCGTCACATCCTGTGATCCACTCTTCATCCCGCTACGTAACACCTCTGCATCGCGAACCAAACC Pecf12_UP807  CAGTACAAAATTTTTAGATGCGTTGCGGGAATCTCCCCGGCCGATGGGCCGTTTCCCAGGTCGAGTGGCCTGAATCGGA Pecf15_UP436  CAGTACAAAATTTTTAGATGCGTTCTTGGGAACCGAACGCCGGTGCCCGCGTTCGGTTCCGGGGATCTTATCAACTTTT Pecf16_3622   CTTGGATGAAAAGAAACCCACCGACGGTGTAACCCTGGCGGCCGATGCAACGAACTAACTCACAGGACGTGCTCAGCACC Pecf17_UP1691 CAGTACAAAATTTTTAGATGCGTTTGGTGAACCAAACTCTTACTCGACTCGTGTCAGTAAGCGGGAGGTGATCGCGTGG Pecf18_UP1700 CAGTACAAAATTTTTAGATGCGTTTGCATCCAGATTGTCTCGGCGGCGGTAATGCCATAAGCAATGTTCGATGGCGCAG Pecf19_UP1315 CAGTACAAAATTTTTAGATGCGTTTCCTCCCGCTCCTGTGGAGCACGATCGAACGCGAACGCGGTCACTATACCCATGC
```

-continued

| Promoter | Sequence (-60 to +20) (SEQ ID NOS: 221-244) |
|---|---|
| Pecf20_992 | GCGCGGATAAAAATTTCATTTGCCCGCGACGGATTCCCCGCCCATCTATCGTTGAACCCATCAGCTGCGTTCATCAGCGA |
| Pecf21_UP4014 | CAGTACAAAATTTTTAGATGCGTTAGGCAACCCTTTTTCATCCGGCTTCGTCTATATCTATAGAAACCGACACCAAACC |
| Pecf22_UP1147 | CAGTACAAAATTTTTAGATGCGTTGTTGTGAGGAATCGCGCTCCTGCGCGAATCATCCCGTGTCGTCCCTTCACCTGCC |
| Pecf24_UP69 | CAGTACAAAATTTTTAGATGCGTTACGGAACGCAGTCTTTTCGTCTGTATCAACTCCAAAATTCATCGTGCCTAAACAT |
| Pecf25_UP4311 | CAGTACAAAATTTTTAGATGCGTCGAGGAACTCAAACTGCGCCATTATCGTCTAGCTAACAGAGGTTCTGCTTGGGAGG |
| Pecf26_UP601 | CAGTACAAAATTTTTAGATGCGTTTGGAATAACCGGTCGCCTCCATCCGTTTACATACCGAATCCCGGCAGCGCCGGCC |
| Pecf29_UP371 | CAGTACAAAATTTTTAGATGCGTTCCGGGAACCTTTTGTCGGCACGAACATCCAATTGGCGGATGAAACACTTTGTCTG |
| Pecf30_2079 | ACCATCCGTATTTTTTAGGGATTTATAAAACTTTTCCATGGCGTGCGTCGTCTAATAAATGGGAAGGAGGAAATGATGT |
| Pecf31_34 | CAATGGCTGAAAAGAATTGTAAAAAAGATGAACGCTTTTGAATCCGGTGTCGTCTCATAAGGCAGAAAAACAAAAAAGGG |
| Pecf32_1122 | GCGACTTTATTTAACAGCGGCATGGCCAGGGAACCGATGCGTCAATCGCACCACACAATGACAACTGCTCTCATCATTGA |
| Pecf33_375 | TAAGTTGAACAATTTTGCACCTTCCGTCGAACCGTCCGCTGCATCGACCCGACCAACCTTGCGAGACGGCCTTTGAGCGT |
| Pecf38_UP1322 | CAGTACAAAATTTTTAGATGCGTTGTACAACCCTCACGGGGTGGACGTGTCCAACTGGCGTGGCAGAGGTTCTCGATT |
| Pecf39_UP1413 | CAGTACAAAATTTTTAGATGCGTTTGTCAACCGTCCACGACGCGCTGGCGTCTGGAAGGGTGACCCAGCCAGACCAGCG |
| Pecf41_UP1141 | CAGTACAAAATTTTTAGATGCGTTCACGTCACAAACCCGAAAGCTGAATCGTCATCCCGTTGAATCCCTCAAACACGGA |
| Pecf42_UP4062 | CAGTACAAAATTTTTAGATGCGTTCGCTGTCGATCCGGCCCGTCGTCGTTCGTCGTACCCCCGAGAGCCCGCGAAAGGC |

In summary, we have constructed a library of 86 ECF σ factors for controlled expression in an *E. coli* host. Overexpression of the majority of these σs has little effect on growth in *E. coli* demonstrating their suitability for use as regulators in this host. Using computational approaches we have identified and constructed promoter models for 34 ECF subgroups. In vivo assays show that the ECF σ-promoter systems are highly orthogonal, with 24 orthogonal systems identified to date. We suggest that these σs are ideal candidates for constructing orthogonal regulatory systems for genetic engineering.

Example 2. Screening a Repressor Library to Build Orthogonal Circuits

This examples describes the construction of chimeric sigmas as a means to diversify available orthogonal regulatory systems. Our work with ECF sigmas demonstrates that they are ideal tools for constructing orthogonal regulatory systems.

ECF sigmas contain 2 highly conserved DNA binding domains. Conserved Region 2 recognizes the promoter −10 sequence and conserved Region 4 recognizes the promoter −35 sequence (FIG. 9). We selected 2 ECF sigmas that each recognized different −10 and −35 sequences (sigmas ECF02_2817 from *Escherichia* coli and ECF11_3726 from *Pseudomonas syringae*; FIG. 9) and constructed chimeric proteins by swapping their DNA binding domains. The domains were connected within the unstructured "linker" region with a seamless join so that no additional amino acids were added or removed. Our most successful chimeric constructs were (FIG. 10): ECF11_ECF02 (containing amino acids 1-106 from ECF02_2817 and 122-202 from ECF11_3726) and ECF02_ECF11 (containing amino acids 1-121 from ECF11_3726 and 107-191 from ECF02_2817).

Figure 11:
FIG. 11 shows the sequences of parental (SEQ ID NOS:32 and 33) and chimeric promoters (SEQ ID NOS:34 and 35).
Figures 12, 13:
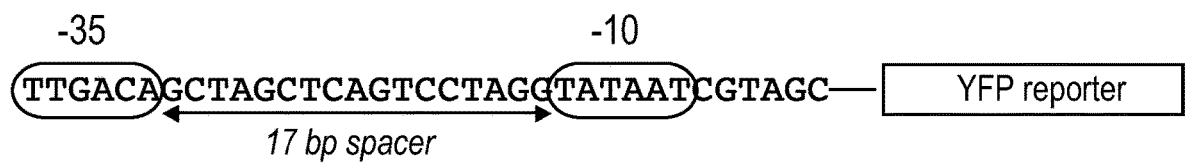
FIG. 12 shows the activity of the parental and chimeric sigmas against their cognate wild type and chimeric promoters. The promoters were fused to gfp reporters and the data represents promoter activity as measured by fluorescence from exponentially growing cells in the presence of each sigma. The data is presented as a heatmap, promoter activity is displayed as fold-change over background and also with a sliding yellow-green scale: yellow is inactive, green is active. Note, not all promoter-sigma combinations have been tested yet.
FIG. 13 shows the operator sequences inserted between the -35/-10 elements of the J23119 promoter (SEQ ID NO:36), which is present upstream of a fluorescent reporter gene (YFP). Modifying promoter sequence content results in subsequent alteration of promoter activity.

Cognate chimeric promoters were also constructed in which the upstream −35 region (sequences −60 to −21) and the downstream −10 region (−19 to +20) were swapped (FIGS. 10 and 11). The activity of parental and chimeric sigmas were assayed in vivo at the wild type and chimeric promoters (FIG. 12). We found that our chimeric sigma factors were able to initiate transcription at their respective chimeric promoters, but not at the "opposite" chimeric promoter, demonstrating that the chimeras are both functional and specific to their target promoters. The high-specificity of the chimeric sigmas demonstrates that this is an effective strategy to dramatically expand the diversity of orthogonal sigma-promoter systems for genetic circuits.

Example 3. Screening a Repressor Library to Build Orthogonal Circuits

This examples demonstrates a method of characterizing a library of repressor proteins belonging to the TetR family. Genetic circuits are often constructed using prokaryotic repressor proteins. Currently, only a few well-characterized repressors are implemented within circuit designs, which severely limit the number and complexity of programs that result. To expand the toolbox of programmable orthogonal operator-repressor pairs, we are characterizing a library of repressor proteins belonging to the TetR family. The newly characterized repressors will allow for the generation of transcriptional circuits of increasing complexity.

A. Generation of the Repressor Library

The Tetracycline repressor (TetR) represents one of the most well characterized microbial regulators. Based on the robust transcriptional control exhibited by TetR, this family of repressors is well suited for use in the programming of genetic circuits. To date, TetR itself is the only repressor within this family that has been used for such purposes. To expand the toolbox of programmable transcriptional repressor proteins, we are characterizing a library of 73 GENEART-synthesized repressors belonging to the TetR family (Table 2).

Using a metagenomic approach, the repressors included within our library originate from 47 distinct prokaryotic organisms, and were selected based on two criteria: 1) homology to TetR, and 2) predicted variation in target sequence recognition. Each gene was refactored and codon optimized for production in *E. coli*. Post-synthesis, repressor coding sequences were inserted downstream of the T7 promoter, into a pET expression vector that contains an amino-terminal 6×-His (SEQ ID NO:141) tag.

B. Repressor Library Characterization Using In Vivo Reporter Assays

The operator sequences recognized by 26 repressors included in our library have been previously identified (Table 3). These operators range 16-55 bp in length, and typically contain inverted repeat sequences. To determine whether these repressors promote repression when paired with their properly matched operator sequences, reporters containing each operator sequence were constructed. Using in vivo reporter assays, constructs were then screened against the library in 96 well format.

Reporters containing 23 of the known operator sequences were constructed, whereby each operator sequence is inserted into a strong constitutive promoter (J23119) that is situated upstream of the yellow fluorescent protein (YFP) reporter gene (FIG. 13). Specifically, operator sequences are inserted into the 17 bp spacer that is present between the −35 and −10 regions of the J23119 promoter sequence. Because known operators are typically larger than 17 bp, the −35 or −10 region must be modified to accommodate each operator (which may render the resulting construct inactive).

Figure 14:
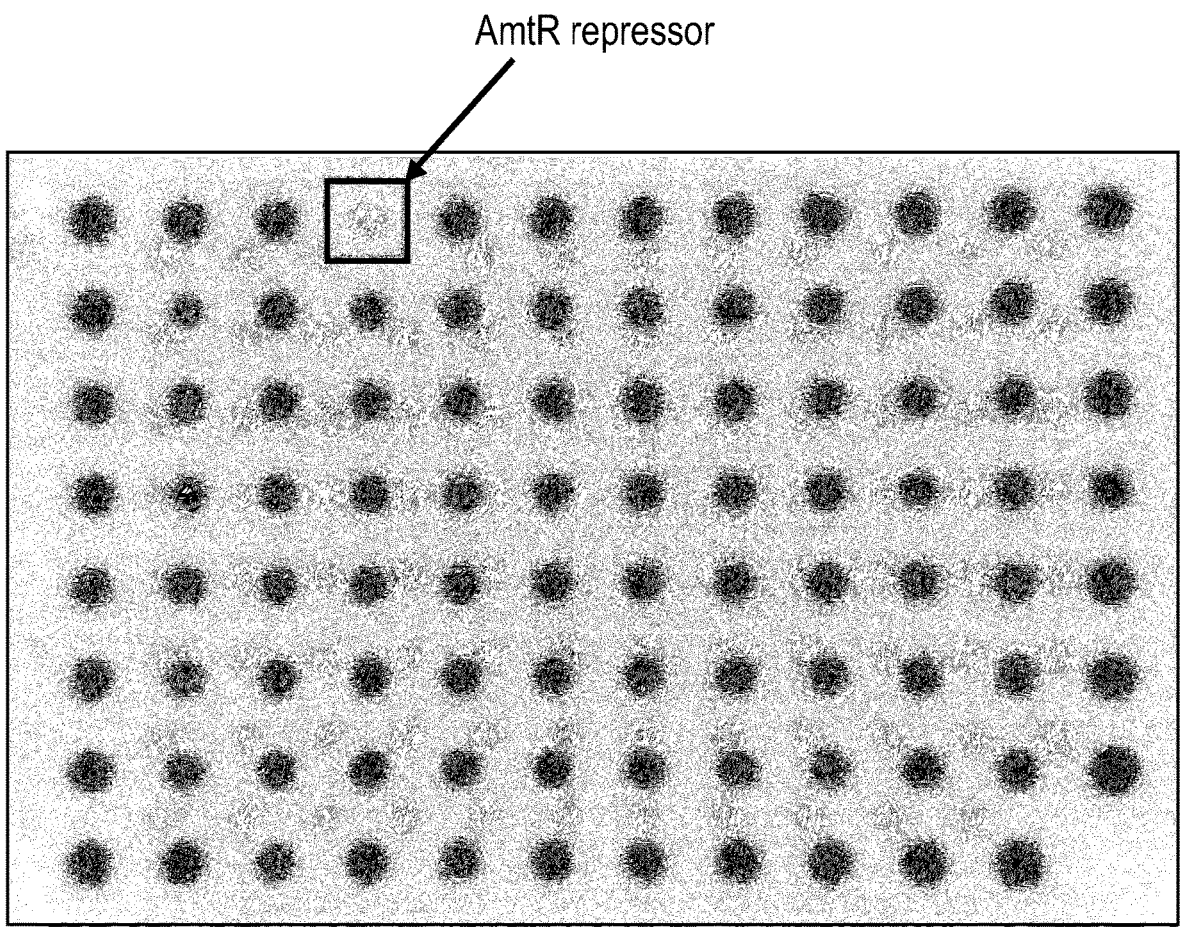
FIG. 14 illustrates repression from the AmtR operator/reporter construct in an in vivo reporter assay. The AmtR operator was inserted into the J23119 promoter and the resulting reporter was screened against the repressor library. Only the AmtR repressor causes repression from the AmtR operator/reporter construct. Each spot corresponds to a different repressor transformed into cells containing the AmtR reporter.

Those reporters that render an active/fluorescent construct are then screened against the library in 96-well format. Specifically, the repressor library is transformed into cells containing an individual reporter and the T7 polymerase gene. A blue light transilluminator is then used to visualize fluorescence and subsequent repression of the transformation plate (FIG. 14). Flow cytometry is used to quantify the level of observed repression (FIG. 15). Of the constructs screened to date, orthogonal repression has been observed for the AmtR, BarB, BetI, ButR, BM3R1, CymR, IcaR, LmrA, McbR, PhlF, QacR, TarA, and TetR repressors. Furthermore, the observed repression is orthogonal; high-levels of repression are observed only in the presence of the properly matched repressor (FIG. 31). Further construction and screening of the known operator sequences is being carried out, and it is expected that additional, orthogonal repressor-operator pairs will be identified.

C. Identifying Sequences Bound by Uncharacterized Repressors

Figure 16:
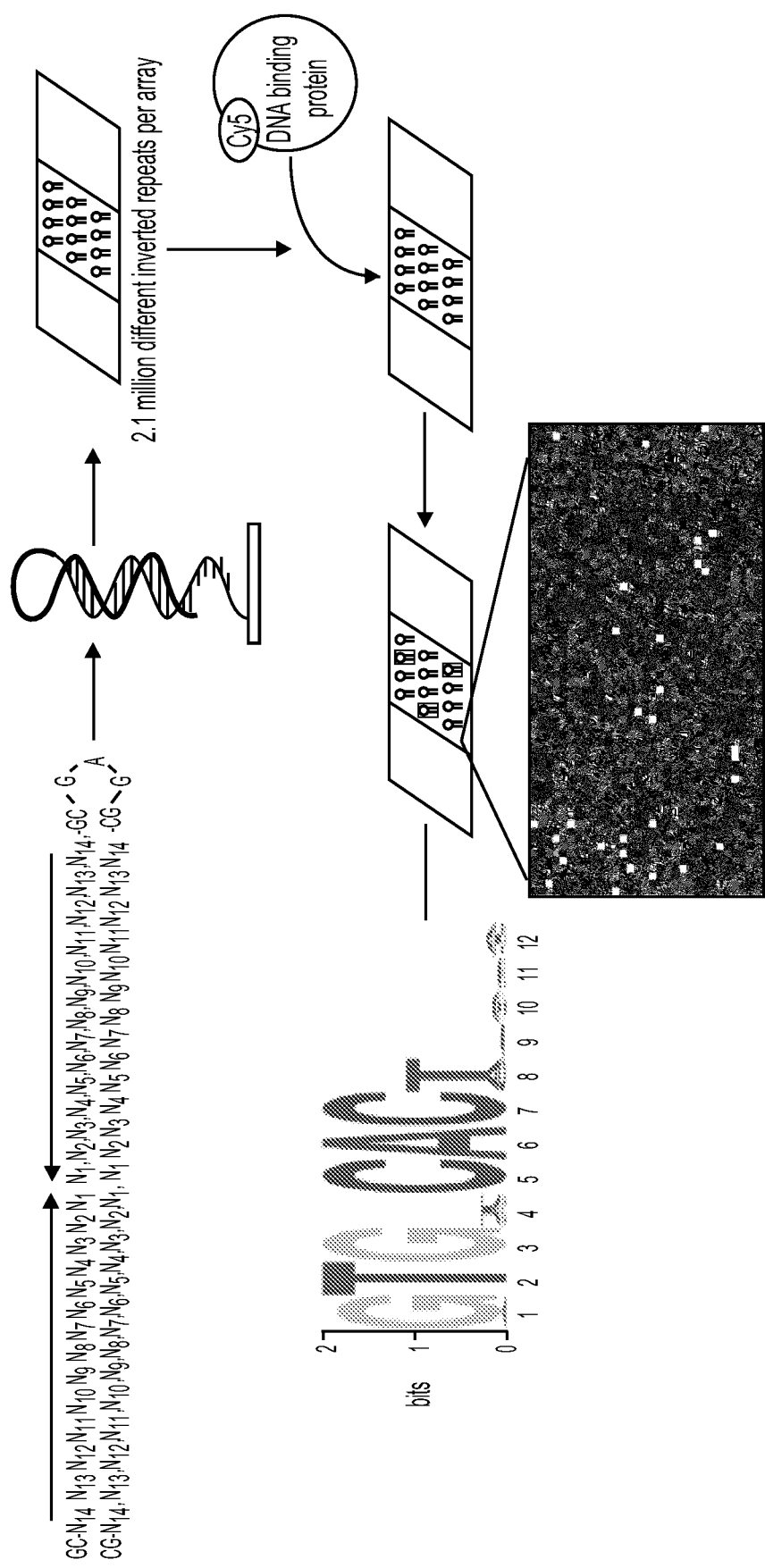
FIG. 16 depicts an array-based approach for identifying synthetic operator sequences. A snapshot of the array, revealing that the purified McbR protein exhibits binding to a 2.1M array, is represented towards the bottom of the figure. Each square in the array represents a distinct sequence. Squares harboring brighter intensities indicate higher affinity sites. Inverted repeat=SEQ ID NO:37; repressor consensus sequence=SEQ ID NO:38.

While some of the operators for repressors included in our library have been characterized, the majority are unknown. To determine the sequences bound by the previously uncharacterized repressors, newly designed protein binding arrays are being utilized. Each array contains 2.1 million distinct 28-mer inverted repeat sequences. A purified, fluorescently labeled repressor is applied to each array; each sequence becomes associated with an intensity value upon repressor binding. Data extraction and motif analysis reveal consensus sequences that are bound with high affinity (FIG. 16). To date, consensus sequences for the AmeR, ArpA, BarA, BarB, ButR, CasR, DhaR, EnvR, and McbR repressors have been identified (FIG. 29).

Using these 2.1M arrays, each repressor within the library is purified and its binding profile extracted. Consensus sequences representing those bound with high affinity, referred to as synthetic operator sequences are then inserted into the J23119 promoter (FIG. 13) and screened for repression. The behavior of those repressors exhibiting high levels of repression are then tuned using a RBS library, to select for those constructs exhibiting a high 'ON' state and a low 'OFF' state (FIG. 30). The transfer function of the newly identified and tuned operator repressor pair is then examined for orthogonality against our library.

In summary, we have constructed and are characterizing a library of 73 TetR homologs. Utilizing both in vivo reporter assays and protein binding arrays, we are determining the sequences bound by each repressor, building reporters, and screening the orthogonality of each newly determined binding sequence against our library in vivo (FIG. 31). Initial results demonstrate that repression is highly specific for the properly matched repressor, and that our library exhibits orthogonal behavior. Complete characterization of the transcriptional repressor library will drastically increase the number of parts available for genetic circuit design, and will thereby enhance the complexity of circuits that may be constructed.

Example 4. Generation of Orthogonal RNAP:Promoter Interactions and Promoters of Different Strengths This example describes a physical library of RNA Polymerases (RNAPs) that bind orthogonal promoter sequences and mutations in these promoters that elicit different strengths of expression. This example also illustrates a method of constructing a T7 RNAP "scaffold" with reduced host toxicity to serve as a platform for creating orthogonal variants. In addition, this example describes the generation of orthogonal RNAP-promoter interaction by analyzing phage genomes to guide mutations to the RNAP scaffold and a region of the T7 promoter. Furthermore, this example describes the generation of promoters of different strengths by mutating a different region of the T7 promoter. Methods herein can be applied to extend the existing library or to create new libraries based on protein-DNA interactions.

The T7 RNAP and promoter have historical utility in gene expression applications and recent utility in synthetic biology genetic circuits. There is value in identifying orthogonal RNAP-promoter interactions as well as promoter variants of differing strengths.

Previous efforts to generate orthogonal RNAP-promoter interactions have fallen into two categories: 1) sourcing RNAP from different phage and characterizing their orthogonality based on which promoters they bind, or 2) mutating the T7 RNAP in an attempt to generate RNAPs that bind different promoters. Previous efforts to generate promoters of different strengths were based on non-specific mutations throughout the entire promoter structure. We have created both orthogonal RNAP-promoter interactions and also numerous phage promoters with different transcriptional strengths.

An embodiments of the invention consists of a physical library of RNAPs that bind orthogonal promoter sequences and mutations to these promoters that elicit different strengths of expression. It can be divided into three primary aspects. Firstly, we constructed a T7 RNAP "scaffold" with reduced host toxicity to serve as a platform for creating orthogonal variants. Secondly, we generated promoters of different strengths by mutating a different region of the T7 promoter. And thirdly, we generated orthogonal RNAP-promoter interactions by analyzing phage genomes to guide mutations to the RNAP scaffold and a region of the T7 promoter. In certain embodiments, the methodology described herein can be applied to extend the existing library or to create new libraries based on protein-DNA interactions.

A. T7 RNAP Scaffold: RNAP Backbone Mutations

We constructed a T7 RNAP "scaffold" with reduced host toxicity to serve as a platform for creating multiple orthogonal variants. We were able to achieve better control of T7 RNAP activity by adopting functional design elements based on four key molecular mechanisms, including physical isolation, translational control, degradative control and processivity modulation. FIG. 17 highlights several of the T7 RNAP scaffolds with varying levels of toxicity.

The physical isolation mechanism allows for the activation of an engineered genetic circuit in host cells that do not carry the T7 RNAP plasmid. We cloned the T7 RNAP on a low copy plasmid, separate from any T7 promoters and/or genes we wished to express. Then, we co-transformed our genetic circuit plasmid and T7 RNAP plasmid into host cells, and were able to activate the circuit.

The translational control mechanism is based on minimizing T7 RNAP concentration by using weak ribosome binding sites, the sequence GTG as an suboptimal start codon, and random DNA spacers which insulate T7 RNAP expression from changes in upstream promoter activity.

The degradative control is achieved by using an N-terminal tag to promote rapid degradation of the T7 RNAP by the Lon protease system. Our tag is based on the N-terminal sequence of the UmuD protein from $E.\ coli$.

It is known by those skilled in the art that naturally, T7 RNAP transcribes DNA approximately eight times faster than the native $E.\ coli$ RNAP. It has been determined that the active site mutations affect both promoter escape and transcription rate. We have characterized mutations located in the O-helix of T7 RNAP that spans residues 625-655. Studies of RNAP mutants have been described from Rui Sousa's laboratory (see, Bonner et al., $EMBO\ J$, 11(10), 3767-75 (1992), Bonner et al., $J\ Biol.\ Chem.$, 269(40), 25120-8 (1994), and Makarova et al., $Proc.\ Natl.\ Acad.\ Sci.\ U.S.A$, 92(26), 12250-4 (1995)). Based on this analysis and our design, we created a library of T7 RNAP mutants and tested their processivity. The best mutation we identified is R632S, which has not been mentioned in any reference to date. We identified the R632S mutation while creating an RBS library. This particular R to S mutation at position 632 has not been studied before.

B. Promoter Strength Library

We developed and utilized a method of modulating RNAP specificity and promoter strength simultaneously by introducing mutations in different domains of the T7 promoter. T7 RNAP recognizes and initiates transcription from 17 promoters in the T7 phage. These promoters vary in sequence, and the consensus sequence is known as the T7 promoter. A number of groups have mutated the T7 promoter to produce variation in promoter activity. The variance is the result of altered binding affinity of the RNAP for the promoter, altered efficiency of transcript initiation, or a combination of the two. Further characterization of the interaction between T7 RNAP and promoter has identified a recognition domain between bases −17 and −5, as well as an initiation domain between bases −4 and +6 (see, Ikeda et al., $Nucleic\ Acids\ Research$, 20(10), 2517-2524 (1992) and McGinness and Joyce, $J\ Biol.\ Chem.$, 277(4), 2987-2991 (2002)). Protein structures have shown that the T7 RNAP initially binds to the recognition domain of the promoter and subsequently interacts with the initiation domain to melt the DNA and form a transcription bubble. Recently, a study from the Ellington lab showed in vitro that mutations of the initially transcribed region (+1 to +6) result in a library of promoters with varying activity (see, Davidson et al., $Symposium\ on\ Biocomputing$, 15, 433-443 (2010)).

We hypothesized that mutations in the recognition domain of the T7 promoter would primarily influence RNAP:DNA binding and mutations in the initiation domain predominately influence rate of transcription initiation. Therefore, we adopted a strategy to modularize the T7 promoter for the purpose of changing RNAP specificity and promoter strength simultaneously. We developed a promoter library by randomly mutating the T7 promoter from bases −2 to +3 (see FIG. 18). The promoter library was cloned into a plasmid vector containing RFP and co-transformed with a mutant T7 RNAP scaffold. We assessed library activity by screening colonies for RFP expression using flow cytometry (see FIG. 18).

C. Terminator Library

To avoid repeated use of the same transcriptional components in the synthetic genetic circuits, we created numerous T7 promoter and transcriptional terminator derivatives. Since duplication of a sequence can hamper in vitro cloning methods or lead to homologous recombination in vivo, each transcriptional unit in the circuit ideally requires a unique transcriptional terminator.

We developed a library of synthetic terminators that facilitate T7 RNAP transcription. Using the naturally occurring T7 phage terminator as a seed sequence, we developed a degenerate terminator sequence that was predicted to form stem-loop structures. We cloned the terminator library between GFP and RFP. When co-transformed with a mutant T7 RNAP scaffold, we observed a reduction in RFP expression for many clones. We assessed termination efficiency across the library by screening colonies for reduction of RFP expression using flow cytometry (see FIG. 19).

D. Methodology for Generating Orthogonal RNAP:Promoter Interactions

We created a methodology to generate orthogonal RNAP:promoter interactions and identified synthetic RNAP:promoter combinations that are mutually orthogonal.

The T7 RNAP specificity loop is a beta-hairpin that extends from approximately residue 730 to approximately residue 770. This loop is the primary determinant of RNAP:DNA binding, and previous crystal structures have shown direct major-groove DNA interactions with residues 746, 748, 756 and 758. Previous research focused on changing these four residues to influence specificity of RNAP binding and to recognize novel promoters.

We hypothesized that specificity loop conformation and DNA interaction are the influenced by the entire loop, not simply the four residues implicated by previous studies. In particular, we thought that random mutagenesis of a few residues within the loop could detrimentally alter the ability of the RNAP specificity loop adopt a conformation that can interact with the major groove of the promoter. However, we also believed that mutations elsewhere in the loop could compensate for mutations to the residues that interact with DNA. These compensating mutations would confer on the loop the ability recover proper conformation for interacting with the promoter and potentially confer specificity for alternative DNA sequences.

An exhaustive search of all possible loop sequences is not feasible (i.e., no. of residues to the power of the no. of 20 amino acids; $\sim 40^{20} = 1 \times 10^{32}$). We believed that we could best source alternative loop sequences from biology. By identifying phage related to T7 in sequence databases, we created library of alternative specificity loop candidates sourced from homologous RNAP. Each RNAP contains a functional specificity loop that is divergent in sequence and possibly in structure from T7 RNAP. Additionally, many of the consensus promoters for phage found in sequence databases diverge from the T7 consensus promoter.

We grafted alternative specificity loops in place of the T7 RNAP specificity loop to produce a library of synthetic RNAP. We found that in many cases this library recognized the consensus promoter for the source phage, rather than the T7 consensus promoter. In four cases, this methodology produced RNAP:promoter combinations that are mutually orthogonal.

The methodology for generating orthogonal binding pairs comprises computational and experimental steps, including identification of RNAP and promoters from phage genomes in sequence databases, alignment of the specificity loop region from all RNAP, creation of synthetic RNAPs and synthetic promoters, and experimental testing for orthogonality.

In certain embodiments, we identified RNAP and promoters from phage genomes in sequence databases. For instance, we selected RNAP sequences based on annotation or sequence homology to T7 RNAP. We selected promoters based on annotations or using a promoter identification algorithm we developed. This algorithm can scan phage genomes and identify regions containing a particular "seed" sequence. For example, a seed sequence we used was the highly conserved core of the T7 consensus promoter, CACTA. We aligned the regions surrounding the seed and eliminated highly divergent sequences.

In certain embodiments, we aligned the specificity loop region from all RNAP based on amino acid sequence. We derived a cladogram from the alignment and used it to identify families of specificity loops. We generated consensus promoters for each phage using sequence logos. Then, we grouped consensus promoters into families based on recognition domain sequence. We observed perfect correlation between the RNAP families and promoter families.

We created synthetic RNAPs by replacing the specificity loop sequence between residues 745 and 761 with a consensus loop sequence from a given phage family. FIG. 20A highlights some of the synthetic RNAPs and their mutated specificity loops. Note that he phage families are named for a representative phage from the family. In certain embodiment, the RNAP based on phage N4 family and retaining the T7 residue 745 was found to exhibit better orthogonality.

We created synthetic promoters by replacing bases −12 to −7 in the T7 consensus promoter with the corresponding bases from the phage family consensus promoter.

We co-transformed synthetic RNAP with synthetic promoters controlling RFP expression. We observed orthogonal activity as expected. Substantially more RFP was produced when synthetic RNAP were co-transformed with the synthetic promoters from the same phage family (see FIG. 20B).

E. Combinatorial Promoters

The methodology described herein was applied to improve the previous iterations of the synthetic promoter library. Combining mutations that confer orthogonality with mutations conferring altered strength into a single promoter greatly extends the utility of our invention. It is possible to utilize multiple RNAP in a single cell, each controlling multiple transcriptional units with a range of specified transcription rates.

Using the methodology described herein, we demonstrated that we could combine orthogonal promoters responsive to T7 RNAP or T3 RNAP with the promoter strength library to achieve predictable outcomes. The combinatorial promoters were assembled from the T7 or T3 synthetic recognition domain and the synthetic initiation domain of the promoter strength library. The experiments demonstrated that promoters showed activity only when co-transformed with the RNAP specified by their recognition domain (see FIG. 21). Additionally, the strength of activity was proportional to that encoded by their initiation domain.

Example 5. 5' UTR Sequences

A complex transcriptional regulatory circuit can be decomposed into several basic modules. These basic modules can consist of a regulatory gene and its regulated promoter. In such basic module, both input and output are promoter activities, and their relation can be described by a transfer function. A task for synthetic biologists is to characterize the transfer function. Unfortunately, transfer function we investigated are context-dependent ("context-dependent" means the same basic module owns different transfer functions in different contexts). In our experiments, the testing module is a NOT logic gate that consists of cI repressor and its repressed pOR1 promoter (sequence: tttgacatacctctggcggtgatatataatggttgc; SEQ ID NO:142). After generating this module, the NOT gate module was connected to three different upstream inducible promoters. The three promoters were:

```
Pbad
(sequence: agaaaccaattgtccatattgcatcagacattgccgtcac tgcgtatttactggctcttctcgctaaccaaaccggtaacccccgcttatt aaaagcattctgtaacaaagcgggaccaaagccatgacaaaaacgcgtaa caaaagtgtctataatcacggcagaaaagtccacattgattatttgcacg gcgtcacactttgctatgccatagcattttttatccataagattagcggat cctacctgacgcttttatcgcaactctctactgtttctccatacccg;

SEQ ID NO: 143),

Ptac
(sequence: ggcaaatattctgaaatgagctgttgacaattaatcatc ggctcgtataatgtgtggaattgtgagcggataacaatttcacac;

SEQ ID NO: 144)
and

Modified-Ptac
(sequence: ggcaaatattctgaaatgagctgataaatgtgagcggat aacattgacattgtgagcggataacaagatactgagcac;

SEQ ID NO: 145).
```

We found that, under the three different promoters, the same NOT gate generated three completely different transfer functions. Experimentally, the input and output promoter activities were measured by the same super-fold gfp(gfp) gene with a same ribosome binding sequence (SDA: actagaaggaggaaaaaaatg; SEQ ID NO:146). See FIG. 23.

We knew that usually a piece of upstream promoter regions are transcribed into message RNA of regulatory genes. It is possible they change the translation rate and/or stability of the mRNA and ultimately change the regulatory gene expression in comparison with reporter gene's, so a fused cI-gfp gene (stop codon of cI is deleted, a short linker sequence "GGCGGTGGCGGT" (SEQ ID NO:147) is added, and the start codon of gfp is removed too) was constructed to monitor the regulatory gene expression. Experimental data indicated the relation between GFP and CI-GFP under Pbad and Ptac promoter are linear but with different slopes (slope of Pbad is 2.31, while slope of Ptac is 0.25). This means that the ratio between the regulatory gene (cI-gfp) and reporter gene (gfp) expression is 2.31 under Ptac promoters, but is 0.25 under Pbad promoter. See FIG. 23. On the other hand, if the transcribed promoter sequence was removed, the inherent properties of promoters were changed by the 5'UTR of the downstream gene region. Our Modified-Ptac promoter belongs to such a case. The Modified-Ptac promoter has a moved LacI binding site from a transcribed promoter region to an un-transcribed promoter region (Ref: Lutz R, Bujard H. *Nucleic Acids Res* 1997, 25:1203-1210). The relation between GFP and CI-GFP was not linear any more. See FIG. 23. With the promoter activity releasing, the expression of GFP increases normally, but the expression of CI-GFP ceases to increase further after a shortly normal increasing, so the inherent dynamical range of Modified-Ptac promoter are changed by CI-GFP with a ribosome binding sequence (SDmut: actagaaccatgaaaaaagtg; SEQ ID NO:148). Therefore, some additional sequence must be identified and inserted between promoter and the downstream gene to insulate them each other.

We have shown that transcriptional modules could seriously interfere with each other when being connected, and some optimized sequences as spacers must be found to prevent such interference. We collected about sixty 5'UTR sequences from the scientific literature and tested their properties by the Modified-Ptac-{spacer}-(gfp/cI-gfp) system. See FIG. 24. Their sequences are listed below. All the sixty sequences can be sorted into five different classes: stem loops, high-transcription escape, anti-escaping sequences, carbon utilization and T5/T7 bacteriophage. Most of the spacers could recover the linear relation between GFP and CI-GFP (their slopes and R-squares are listed below). In the whole spacer library, the best spacer was a ribozyme that can remove 5' leading sequences that come from the upstream promoter region after transcribed into mRNA (bottom and right of FIG. 24).

| Num/names | Sources | Sequence (SEQ ID NO:) | Slope | Statistics (Adj. $R^2$) | References |
|---|---|---|---|---|---|
| 1 pD/E20J | T5 phage | Agttcgatgagagcgataacccctctacaaataatttttg tttaa (149) | 0.913 | 0.999 | [Ref 1] |
| 2 pH207J | T5 phage | ataaattgataaacaaaaacctctacaaataatttttgt ttaa (150) | 0.679 | 0.991 | [Ref 1] |
| 3 pN25J | T5 phage | ataaatttgagagaggagttcctctacaaataatttttg tttaa (151) | 0.349 | 0.991 | [Ref 2] |
| 4 pG25J | T5 phage | attaaagaggagaaattaaccctctacaaataatttttg tttaa (152) | 0.370 | 0.998 | [Ref 1] |
| 5 pJ5J | T5 phage | aaacctaatggatcgaccttcctctacaaataatttttg tttaa (153) | 6.49 | 0.996 | [Ref 1] |
| 6 pA1J | T7 phage | atcgagagggacacggcgacctctacaaataatttttgt ttaa (154) | 0.421 | 0.996 | [Ref 1] |
| 7 pA2J | T7 phage | gctaggtaacactagcagccctctacaaataatttttgt ttaa (155) | 0.862 | 0.998 | [Ref 1] |
| 8 pA3J | T7 phage | atgaaacgacagtgagtcacctctacaaataatttttgt ttaa (156) | 1.407 | 0.990 | [Ref 1] |
| 9 phi10J | T7 phage | agggagaccacaacggtttccctctacaaataatttttg tttaa (157) | 0.582 | 0.995 | [Ref 3] |
| 10 DG146aJ | High-transcription escape | attaaaaaacctgctaggatcctctacaaataatttttg tttaa (158) | 1.693 | 0.995 | [Ref 4] |
| 11 DG122J | High-transcription escape | ataaaggaaaacggtcaggtcctctacaaataatttttg tttaa (159) | N/A | N/A | [Ref 4] |
| 12 DG131aJ | High-transcription escape | ataggttaaaagcctgtcatcctctacaaataatttttg tttaa (160) | 2.708 | 0.996 | [Ref 4] |
| 13 MhpR3hppJ | Carbon utilization | acaataaaaaatcatttacatgtttcctctacaaataa ttttgtttaa (161) | 2.215 | 0.884 | [Ref 10] |
| 14 GlcCJ | Carbon utilization | agaagcagcgcgcaaaaatcagctgcctctacaaataa ttttgtttaa (162) | 0.319 | 0.990 | [Ref 10] |
| 15 FucRPfucPJ | Carbon utilization | atgagttcatttcagacaggcaaatcctctacaaataa ttttgtttaa (163) | 1.336 | 0.996 | [Ref 10] |
| 16 FuncRPfucAJ | Carbon utilization | aacttgcagttatttactgtgattacctctacaaataa ttttgtttaa (164) | 0.899 | 0.998 | [Ref 10] |
| 17 ChbRNagCJ | Carbon utilization | agccacaaaaaagtcatgttggttcctctacaaataa ttttgtttaa (165) | 1.104 | 0.971 | [Ref 10] |

-continued

| Num/names | Sources | Sequence (SEQ ID NO:) | Slope | Statistics (Adj. $R^2$) | References |
|---|---|---|---|---|---|
| 18 AraCJ | Carbon utilization | acacagtcacttatctttttagttaaaaggtcctctaca aataattttgtttaa (166) | 0.961 | 0.998 | [Ref 10] |
| 19 AntiescapeJ | Anti-escaping sequences | atccggaatcctcttcccggcctctacaaataattttg tttaa (167) | 2.245 | 0.995 | [Ref 5] |
| 20 LeiQiJ | | aacaaaataaaaaggagtcgctcaccctctacaaataa ttttgtttaa (168) | 0.112 | 0.396 | [Ref 6] |
| 21 pD/E20RBS | T5 phage | agttcgatgagagcgataacagttccagattcaggaac tataa (169) | 0.216 | 0.994 | [Ref 1] |
| 22 pH207RBS | T5 phage | ataaattgataaacaaaaaagttccagattcaggaact ataa (170) | 0.509 | 0.999 | [Ref 1] |
| 23 pN25RBS | T5 phage | ataaatttgagagaggagttagttccagattcaggaac tataa (171) | 1.058 | 0.998 | [Ref 2] |
| 24 pG25RBS | T5 phage | attaaagaggagaaattaacagttccagattcaggaac tataa (172) | 0.806 | 0.999 | [Ref 1] |
| 25 pJ5RBS | T5 phage | aaacctaatggatcgaccttagttccagattcaggaac tataa (173) | 0.454 | 0.999 | [Ref 1] |
| 26 pA1RBS | T7 phage | atcgagagggacacggcgaagttccagattcaggaact ataa (174) | 2.532 | 0.999 | [Ref 1] |
| 27 pA2RBS | T7 phage | gctaggtaacactagcagcagttccagattcaggaact ataa (175) | N/A | N/A | [Ref 1] |
| 28 pA3RBS | T7 phage | atgaaacgacagtgagtcaagttccagattcaggaact ataa (176) | N/A | N/A | [Ref 1] |
| 29 phi10RBS | T7 phage | agggagaccacaacggttttcagttccagattcaggaac tataa (177) | 0.363 | 0.999 | [Ref 3] |
| 30 DG146aRBS | High-transcription escape | attaaaaaacctgctaggatagttccagattcaggaac tataa (178) | 1.779 | 0.997 | [Ref 4] |
| 31 DG122RBS | High-transcription escape | ataaaggaaaacggtcaggtagttccagattcaggaac tataa (179) | 0.514 | 0.998 | [Ref 4] |
| 32 DG131aRBS | High-transcription escape | ataggttaaaagcctgtcatagttccagattcaggaac tataa (180) | 0.118 | 0.997 | [Ref 4] |
| 33 MhpR3hppRBS | Carbon utilization | acaataaaaaatcatttacatgtttagttccagattca ggaactataa (181) | 3.849 | 0.998 | [Ref 10] |
| 34 GlcCRBS | Carbon utilization | agaagcagcgcgcaaaaatcagctgagttccagattca ggaactataa (182) | 0.329 | 0.989 | [Ref 10] |
| 35 FucRPfucPRBS | Carbon utilization | atgagttcatttcagacaggcaaatagttccagattca ggaactataa (183) | 0.388 | 0.999 | [Ref 10] |
| 36 FuncRPfucARBS | Carbon utilization | aacttgcagttatttactgtgattaagttccagattca ggaactataa (184) | 0.248 | 0.994 | [Ref 10] |
| 37 ChbRNagCRBS | Carbon utilization | agccacaaaaaaagtcatgttggttagttccagattca ggaactataa (185) | N/A | N/A | [Ref 10] |
| 38 AraCRBS | Carbon utilization | acacagtcacttatctttttagttaaaaggtagttccag attcaggaactataa (186) | 0.539 | 0.959 | [Ref 10] |
| 39 AntiescapeRBS | Anti-escaping sequences | atccggaatcctcttcccggagttccagattcaggaac tataa (187) | 5.543 | 0.983 | [Ref 5] |
| 40 LeiQiRBS | | aacaaaataaaaaggagtcgctcacagttccagattca ggaactataa (188) | N/A | N/A | [Ref 6] |
| 41 OmpA4 | Stem loops | gatcaccagggggatcccccggtgaaggat (189) | 0.369 | 0.949 | [Ref 7] |

| Num/names | Sources | Sequence (SEQ ID NO:) | Slope | Statistics (Adj. $R^2$) | References |
|---|---|---|---|---|---|
| 42 OmpA952 | Stem loops | gatcgcccaccggcagctgccggtgggcgatcaaggat (190) | 0.282 | 0.691 | [Ref 7] |
| 43 OmpA29 | Stem loops | gatcatcggtagagttaatattgagcagatcccccggt gaaggat (191) | 4.039 | 0.994 | [Ref 7] |
| 44 papA | Stem loops | attgatctggttattaaaggtaatcgggtcatttta (192) | 1.583 | 0.990 | [Ref 7] |
| 45 pufBA | Stem loops | gttctccacgggtgggatgagccctcgtggtggaaat gcg (193) | 2.353 | 0.975 | [Ref 7] |
| 46 gene32 | Stem loops | agcatgaggtaaagtgtcatgcaccaa (194) | 0.052 | 0.767 | [Ref 7] |
| 47 pHP4 | Stem loops | acgtcgacttatctcgagtgagatattgttgacggtac (195) | 1.381 | 0.972 | [Ref 8] |
| 48 pHP10 | Stem loops | acgtcgacttatctcgagtgagataagttgacggtac (196) | 1.620 | 0.999 | [Ref 8] |
| 49 pHP17 | Stem loops | acgtcgacttatctcgagactgcagttcaatagagata ttgttgacggtac (197) | 0.155 | 0.961 | [Ref 8] |
| 50 Ribo50 | Stem loops (Ribozyme) | gactgtcaccggatgtgctttccggtctgatgagtccg tgaggacgaaacag (198) | 0.341 | 0.971 | [Ref 9] |
| 51 OmpA952J | Stem loops | gatcaccaggggatcccccggtgaaggatcctctaca aataattttgtttaa (199) | 0.908 | 0.991 | [Ref 7] |
| 52 OmpA64J | Stem loops | Gatcgcccaccggcagctgccggtgggcgatcaaggat cctctacaaataattttgtttaa (200) | N/A | N/A | [Ref 7] |
| 53 OmpA29J | Stem loops | gatcatcggtagagttaatattgagcagatcccccggt gaaggatcctctacaaataattttgtttaa (201) | 0.776 | 0.958 | [Ref 7] |
| 54 papAJ | Stem loops | attgatctggttattaaaggtaatcgggtcattttacc tctacaaataattttgtttaa (202) | 0.049 | 0.671 | [Ref 7] |
| 55 pufBAJ | Stem loops | Gttctccacgggtgggatgagccctcgtggtggaaat gcgcctctacaaataattttgtttaa (203) | 0.046 | 0.699 | [Ref 7] |
| 56 gene32 | Stem loops | agcatgaggtaaagtgtcatgcaccaacctctacaaat aattttgtttaa (204) | 0.667 | 0.937 | [Ref 7] |
| 57 pHP4J | Stem loops | Acgtcgacttatctcgagtgagatattgttgacggtacc ctctacaaataattttgtttaa (205) | 1.125 | 0.952 | [Ref 8] |
| 58 pHP10J | Stem loops | Acgtcgacttatctcgagtgagataagttgacggtacc ctctacaaataattttgtttaa (206) | 0.070 | 0.447 | [Ref 8] |
| 59 pHP17J | Stem loops | acgtcgacttatctcgagactgcagttcaatagagata ttgttgacggtaccctctacaaataattttgtttaa (207) | 0.546 | 0.986 | [Ref 8] |
| 60 RiboJ | Stem loops (Ribozyme) | gactgtcaccggatgtgctttccggtctgatgagtccg tgaggacgaaacagcctctacaaataattttgtttaa (208) | 1.050 | 0.996 | [Ref 9] |

1. Deuschle U, Kammerer W, Gentz R, Bujard H: Promoters of *Escherichia coli*: a hierarchy of in vivo strength indicates alternate structures. *EMBO J* 1986, 5:2987-2994.
2. Kammerer W, Deuschle U, Gentz R, Bujard H: Functional dissection of *Escherichia coli* promoters: information in the transcribed region is involved in late steps of the overall process. *EMBO J* 1986, 5:2995-3000.
3. Davis J H, Rubin A J, Sauer R T: Design, construction and characterization of a set of insulated bacterial promoters. *Nucleic Acids Res* 2011, 39:1131-1141.
4. Hsu L M, Cobb I M, Ozmore J R, Khoo M, Nahm G, Xia L, Bao Y, Ahin C: Initial transcribed sequence mutations specifically affect promoter escape properties. *Biochemistry* 2006, 45:8841-8854.
5. Chan C L, Gross C A: The anti-initial transcribed sequence, a portable sequence that impedes promoter escape, requires sigma70 for function. *J. Biol. Chem* 2001, 276:38201-38209.
6. Lynch S A, Desai S K, Sajja H K, Gallivan J P: A high-throughput screen for synthetic riboswitches reveals mechanistic insights into their function. *Chem. Biol* 2007, 14:173-184.
7. Emory S A, Bouvet P, Belasco J G: A 5'-terminal stem-loop structure can stabilize mRNA in *Escherichia coli*. *Genes Dev* 1992, 6:135-148.
8. Carrier T A, Keasling J D: Library of synthetic 5' secondary structures to manipulate mRNA stability in *Escherichia coli*. *Biotechnol. Prog* 1999, 15:58-64.

9. Nelson J A, Shepotinovskaya I, Uhlenbeck O C: Hammerheads derived from sTRSV show enhanced cleavage and ligation rate constants. *Biochemistry* 2005, 44:14577-14585.
10. Website: on the world wide web biocyc.org/.

We tested the Ribozyme spacer (RiboJ) under all three tested upstream promoters. For all three promoters, the riboJ spacer can process the transcribed mRNA and remove the transcribed promoter region from the mRNA. As a result, the transcripts of gfp, cI-gfp and cI genes become unique, even though their promoter region and transcribed 5'leading sequence of mRNA are completely different. Our experimental data showed the slope for GFP and CI-GFP relation converged into a same value (about 1.16) after adding the RiboJ spacer. The slope for the Pbad promoter increased from 0.25 to 1.19, while the slope for Ptac promoter decrease from 2.31 to 1.14. See, FIG. 25. Notably, the nonlinear relation between CI and CI-GFP under Modified-Ptac promoter became linear with the similar slope (1.11) in comparison with two previous promoters. When we inserted the RiboJ spacer between the NOT gate module and the three upstream inducible promoters, the relation between input and output promoter activity become unique. This means that the NOT gate has the same transfer function in different contexts and can become easily predicted. We also tested other three NOT gate modules (cI-POR222, cILVA-PORI and cILVA-POR222), all of them having a unique transfer function in three different contexts. In summary, this spacer-added assembling method can dramatically promote the construction of more complex transcriptional circuits.

Part Mining Additional Insulator Parts

Genetic programs are getting larger, requiring the functional connection of multiple genetic circuits. The reliable connection of these circuits will require the routine incorporation of insulator parts into the circuit design. The ribozyme function is locally implemented, so orthogonality and crosstalk is not a problem as it is in the scale-up of the number of circuits. However, re-using the same 75 bp part in a design could lead to homologous recombination and evolutionary instability (Galdzicki, M., Rodriguez, C., Chandran, D., Sauro, H. M. & Gennari, J. H. Standard Biological Parts Knowledgebase. *PLoS One* 6, (2011)). To expand the number of available insulators, the NCBI sequence database was searched for sequences similar to the sTRSV-ribozyme. Nine additional ribozymes were identified and screened for their insulating capability (see table below). These sequences share only an average of 75% sequence identity.

Each ribozyme was tested for its ability to produce the same ratio of CI-GFP to GFP, whether under the control pTAC or pBAD (Table 2). Each ribozyme differed in its capability to rectify the ratios. Out of this library, five were identified that function as insulators: sLTSV+ (Forster, A. C. & Symons, R. H. Cell 50, 9-16 (1987)), Scc+ (Di Serio, F., Darós, J. A., Ragozzino, A. & Flores, R. *J Virol.* 71, 6603-6610 (1997)), SarMV+ (Kaper, J. M., Tousignant, M. E. & Steger, G. *Biochem. Biophys. Res. Commun.* 154, 318-325 (1988)), PLMVd-(Hernández, C. & Flores, R. *Proc. Natl. Acad. Sci. U.S.A.* 89, 3711-3715 (1992)), sVT-MoV+ (Roossinck, M. J., Sleat, D. & Palukaitis, P. Satellite RNAs of plant viruses: structures and biological effects. *Microbiol. Rev.* 56, 265-279 (1992)). This demonstrates that the insulating function is a general property of the ribozyme function, and not specific to the sTRSV-ribozyme.

| | Performance of Ribozymes Obtained via Part Mining | | |
|---|---|---|---|
| Name[a] | Sequence (SEQ ID NOS: 209-218)[b] | Slope[c] pBAD | Slope[c] pTAC |
| LtsvJ | AGTACGTCTGAGCGTGATACCCGCTCACTGAAGATGGCCCGGTAGGGCCGAAACGTACCTCTACAAATAATTTTGATTAA | 0.6 | 0.6 |
| SccJ | AGATGCTGTAGTGGGATGTGTGATCTCACCTGAAGAGTACAAAAGTCCGAAACGGTATCCTCTACAAATAATTTAGTTTAA | 1.1 | 1.2 |
| RiboJ | AGCTGTCACCGGATGTGCTTTCCGGATCTGATGAGTCCGTGAGGACGAAACAGCCTCTACAAATAATTTTGTTTAA | 1.4 | 1.3 |
| SarJ | AGACTGTCGCCGGATGTGTATCCGACCTGACGATGGCCCAAAAGGGCCGAAACAGTCCTCTACAAATAATTTTGTTTAA | 2.2 | 2.4 |
| PlmJ | AGTCATAAGTCTGGGCTAAGCCCACTGATGAGTCGCTGAAATGCGACGAAACTTATGACCTCTACAAATAATTTTGTTTAA | 1.6 | 1.8 |
| VtmoJ | AGTCCGTAGTGGATGTGTATCCACTCTGATGAGTCCGAAAGGACGAAACGGACCTCTACAAATAATTTTGTTTAA | 1.0 | 1.3 |
| ChmJ | AGAAGAGGTCGGCACCTGACGTCGGTGTCCTGATGAAGATCCATGACAGGATCGAAACCTCTTCCTCTACAAATAATTTTGTTTAA | 1.9 | 2.4 |
| ScvmJ | AGTACTGTCGCCAGACGTGGACCCGGCCTGATGAGTCCGAAAGGACGAAACAGTACCTCTACAAATAATTTTGTTTAA | 0.8 | 1.4 |
| SltJ | AGGACGTATGAGACTGACTGAAACGCCGTCTCACTGATGAGGCCATGGCAGGCCGAAACGTCCCTCTACAAATAATTTTGTTTAA | 2.2 | 1.4 |

-continued

Performance of Ribozymes Obtained via Part Mining

| Name[a] | Sequence (SEQ ID NOS: 209-218)[b] | Slope[c] pBAD | Slope[c] pTAC |
|---|---|---|---|
| PlmvJ | AGGAAGAGTCTGTTGCTAAGCACACTGACGAGTCTCTGAGATGA-GACGAAACTCTTCCCTCTACAAATAATTTTGTTTAA | 2.0 | 5.9 |

[a]All the names were changed on the base of their original names in the reference[7,8], as an additional hairpin was added to expose the SD sequence in the RBS.
[b]The green residues forming the stem I, the blue residues forming the stem II and the red residues as the conserved catalytic core come from these ribozymes. The pink residues forming the stem III come from the additional hairpin.
[c]The slope of the expression of gfp and cI-gfp genes under the control of two promoters. The slopes are calculated as the average of at least three experiments on different days. The average error was 14%. The detailed measurements, including standard deviations are provided in the additional table below.

Performances of 10 Ribozyme Spacers

Besides the RiboJ-ribozyme spacer, we also tested nine other ribozymes under the pTAC and pBAD promoter in order to discover alternative insulators. For each spacer, we measured the expression of GFP and CI-GFP for both the pTAC and pBAD inducible systems. The relationship of GFP and CI-GFP was fitted with a linear curve by origin software (OriginLab Inc.). The slopes are provided in Table S3.

Summary of performances of Ribozyme spacers

| | | | Slopes | | | | |
|---|---|---|---|---|---|---|---|
| Rank | Name | promoter name | Day 1 | Day 2 | Day 3 | Day 4 | Mean ± std |
| 1 | LtsvJ | pBAD | 0.603 | 0.587 | 0.547 | 0.566 | 0.575 ± 0.0244 |
| | | pTAC | 0.605 | 0.533 | 0.581 | 0.523 | 0.56 ± 0.039 |
| 2 | SccJ | pBAD | 1.24 | 1.097 | 1.08 | 1.088 | 1.13 ± 0.0762 |
| | | pTAC | 1.389 | 1.09 | 1.172 | 0.936 | 1.15 ± 0.189 |
| 3 | RiboJ | pBAD | 1.13 | 1.68 | 1.37 | 1.59 | 1.44 ± 0.246 |
| | | pTAC | 1.141 | 1.66 | 1.075 | 1.25 | 1.28 ± 0.262 |
| 4 | SarJ | pBAD | 2.36 | 2.27 | 1.95 | 2.19 | 2.19 ± 0.176 |
| | | pTAC | 2.44 | 2.55 | 2.37 | 2.13 | 2.37 ± 0.178 |
| 5 | PlmJ | pBAD | 1.77 | 1.49 | 1.33 | 1.69 | 1.57 ± 0.197 |
| | | pTAC | 1.89 | 1.76 | 1.76 | 1.77 | 1.79 ± 0.0635 |
| 6 | VtmoJ | pBAD | 1.065 | 1.04 | 0.999 | 0.927 | 1.01 ± 0.0603 |
| | | pTAC | 1.43 | 1.25 | 1.226 | 1.162 | 1.27 ± 0.115 |
| 7 | ChmJ | pBAD | 1.91 | 1.82 | 1.85 | 2.11 | 1.92 ± 0.130 |
| | | pTAC | 2.28 | 2.4 | 2.73 | 2.14 | 2.39 ± 0.252 |
| 8 | ScvmJ | pBAD | 0.91 | 0.77 | 0.79 | 0.81 | 0.82 ± 0.0622 |
| | | pTAC | 1.56 | 1.377 | | 1.277 | 1.41 ± 0.144 |
| 9 | SltJ | pBAD | 2.07 | 2.0 | 1.74 | 2.95 | 2.19 ± 0.526 |
| | | pTAC | 1.5 | 1.45 | 1.22 | 1.22 | 1.43 ± 0.149 |
| 10 | PlmvJ | pBAD | 2.32 | 1.96 | 1.39 | 2.42 | 2.02 ± 0.466 |
| | | pTAC | 5.74 | 7.57 | 4.86 | 5.62 | 5.95 ± 1.15 |

Example 6. AND Gates

AND Gates

Three 2-input AND gates have been constructed and fully characterized. See, FIG. 26. All the genetic parts including promoters and genes are from Type III secretion systems. The type III secretion system (T3SS) is a molecular machine, which secretes effector proteins from pathogenic bacteria to eukaryotic cells during infection. This system has a complex regulatory network including activator-chaperone pairs, which can be used for building AND gates. For example (FIG. 26, left top), InvF, an AraC-like activator from the *Salmonella* pathogenicity island 1, interacts with SicA, a chaperone protein. This InvF-SicA complex can activate the sicA promoter (psicA) when the complex binds to the promoter. That is, such activation happens only when the two proteins coexist. Thus, this system acts as an AND gate.

Three other activator-chaperone pairs have been recruited from *Shigella flexneri*, *Yersinia enterocolitica*, and *Pseudomonas aeruginosa*. The YsaE-SycB (activator-chaperone) pair from *Yersinia enterocolitica* did not work in *E. coli* DH10B, but all other three pairs (InvF-SicA, MxiE-IpgC, and ExsDA-ExsC) work as AND gates. The mechanism for the ExsDA-ExsC system is different from that of InvF-SicA and MxiE-IpgC. ExsA is an activator and activates the pexsC promoter without forming complex with chaperone protein. Instead, there is ExsD molecule in the system, which sequesters and prevents ExsA from binding to the promoter. Consequently, when the two genes (exsD and exsA) are under the same promoter control (in this case, pTet), inducing this promoter by adding aTc (inducer) does not lead to activation of pexsC promoter. Once the chaperone ExsC coexists in the system, however, ExsC binds to ExsD more tightly than ExsA does. Thus, if all three proteins coexist and ExsC sequesters ExsD enough to release free ExsA, the pexsC promoter can be turned on.

The AND gates consist of three parts (middle three portion of FIG. 26): two inducible input promoters, activator-chaperone genes under the control of these inducible promoters, and a reporter gene (rfp, red fluorescence protein gene) under the control of the promoter that is activated by the activator-chaperone complex (or by the activator alone for the pexsC case). The three gates have been fully characterized by measuring fluorescence (right three portions of FIG. 26). *E. coli* strain DH10B containing the AND gate was grown in LB medium (Miller, BD Bioscience, San Jose, Calif.) overnight at 37° C. and then transferred to fresh LB medium. The cultures were induced at OD of 0.5 with inducers of different concentrations. The inducer concentrations are as follows: arabinose concentrations (Ara, mM) are 0, 0.0016, 0.008, 0.04, 0.2, 1, 5, and 25 from bottom to top of FIG. 26; 30C6 homoserine lactone concentrations (30C6, nM) are 0, 0.32, 1.6, 8, 40, 200, 1000, and 5000 from bottom to top of FIG. 26; and anhydrotetracycline concentrations (aTc, ng/ml) are 0, 0.0032, 0.016, 0.08, 0.4, 2, 10, and 50 from left to right. Each culture (0.6 ml) was induced for 6 hrs in 96-well plates (deep well plates with total volume capacity of 2 ml) and flow cytometer data were obtained using a BD Biosciences LSRII flow cytometer (BD Bioscience, San Jose, Calif.). The data were gated by forward and side scatter, and each data set consists of at least 10,000 cells. The average fluorescence was calculated using FlowJo (TreeStar Inc., Ashland, Oreg.). The scale bar is in a log scale.

Gate Orthogonality

When the AND gates are connected, these gates should be orthogonal. That is, each activator-chaperone pair should interact only with its cognate partner and promoter, not with the other partners and promoters. All the possible interaction combinations have been tested, and orthogonality of the three AND gates were confirmed (see the middle and right heat-maps of FIG. 27; fluorescence values are normalized by a maximum value and the scale bar is in a linear scale; all the experiments were performed as described above using each strain containing activator-chaperone-promoter as indicated in the figures). The middle and right heat-maps of FIG. 27 show orthogonality of activator/chaperone interaction and activator/promoter binding, respectively.

The wild-type SicA cross-talks (interacts) with MxiE. To eliminate such cross-talk, the sicA gene was mutated and a SicA mutant (SicA*F62Y) was found to be orthogonal to the other partners. To obtain this sicA variant, error-prone PCR was performed and library of SicA mutant proteins was screened as follows:

Random mutations were introduced by PCR reactions which were performed using 1×PCR buffer (Invitrogen, Carlsbad, Calif.) supplemented with 7 mM MgCl$_2$, 0.3 mM MnCl$_2$, 0.2 mM of dATP and dGTP, 1 mM of dCTP and dTTP, and 0.05U Taq DNA polymerase (Invitrogen, Carlsbad, Calif.).

Using the same experimental procedure as described above, strains containing the mutated sicA gene, the invF gene, and psicA promoter were screened, and positive clones with high fluorescence (compared to a positive control that contains wild type sicA-invF-psicA) were selected at 5 mM Ara and 100 ng/ml aTc.

The selected sicA mutant genes were transformed into strains containing MxiE and the pipaH9.8 promoter, and the negative clone (containing SicA*) with low fluorescence (compared to a negative control that contains wild type sicA-invF-pipaH9.8) was selected at 5 mM Ara and 100 ng/ml aTc.

The promoter pipaH9.8 was mutated to reduce its basal expression level. Its high basal expression level can be problematic when the AND gate containing it is connected with other gates. One issue is a so-called impedance matching problem. Imagine a simple cascade circuit where an input promoter of the first module generates an activator, which turns on an output promoter of the second module. If the promoter of the first module has too high a basal activity, the activator is always expressed enough to turn on the output of the second module, and the entire circuit is always on. To improve its dynamic range, the −10 region of the pipaH9.8 promoter was changed from TATAAT to TAAGAT by using saturation mutagenesis. The forward and reverse primers for saturation mutagenesis are as follows: NNATAAAAAGTGCTGAATTCAC (SEQ ID NO:219) and NNATAAGGATAAACAAAATTGGCTG (SEQ ID NO:220), respectively.

4-Input AND Gate

The three 2-input AND gates constructed above (see AND GATE Section) were connected (as shown in the left of FIG. 28) to create a 4-input AND gate. This gate comprises four sensors (6 kb in size), integrated circuits (6 kb in size), and reporter gene (rfp in this diagram). The entire system has 11 orthogonal regulatory proteins in one cell.

The sensor module consists of 4 input promoters (pBAD, pTac, pLux, and pTet) and the genes encoding their regulatory proteins (AraC, Lacd, LuxR, and TetR). The four inputs for the four sensor promoters are Ara, IPTG, AI-1 (30C6), and aTc. Each input promoter is connected with the gene(s) encoding the regulatory protein(s) from T3SS (IpgC, MxiE, ExsC, ExsD/ExsA). Note that the input promoter for mxiE is switched from pTet (see the middle diagram in the Section 1) to pTac. In addition, the output gene rfp for the pipaH9.8 and pexsC promoters (see the middle of FIG. 26) are replaced with sicA* and invF, respectively. Such swapping allows the three 2-input AND gates to be connected to each other (making the integrated circuit module) as well as to the sensor module. As described in the AND GATE Section, each 2-input AND gate is turned on only when both inputs are on (signal 1). Thus, this 4-input AND gate is turned on only when the four input is on. The fluorescence was measured as described above using the *E. coli* strain DH10B containing this 4-input AND gate, and the result is shown in the histogram. The four inducer concentrations used for the "on" input (signal 1) are as follows: Ara (5 mM), IPTG (0.5 mM), 30C6 (5 μM), and aTc (2 ng/ml). The x-axis is fluorescence (arbitrary unit, au) and the y-axis is the normalized cell count. All the DNA parts were assembled using the one-step isothermal DNA assembly method (*Nat. Methods*, 6, 343-345). The strain contains three plasmids with total size of 21 kb:

1. pXCPi-epA containing
   araC and lac under constitutive promoter control,
   ipgC under pBAD control,
   mxiE under pTac control, and
   sicA* under pipaH9.8 control
2. pCDAC-invF containing
   luxR and tetR under constitutive promoter control,
   exsC under pLux control,
   exsDA under pTet control
   invF under pexsC control
3. psicA-rfp containing rfp under psicA control The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A host cell comprising a heterologous genetic circuit comprising at least two orthogonal sequence-specific DNA binding polypeptides, wherein the genetic circuit is a combination of logic gates,
   wherein the logic gates are combined by having a connection promoter that is an output promoter of an upstream gate and an input promoter of a downstream gate,
   wherein a stem loop ribozyme spacer sequence is included after the connection promoter, and
   wherein the stem loop ribozyme spacer sequence comprises any one of SEQ ID NOS:209-218.

2. The host cell of claim 1, wherein the logic gates are selected from the group consisting of AND, NAND, NOR, OR, NOT, XOR, EQUALS, AND IMPLIES, and ANDN gates.

3. The host cell of claim 2, wherein the NOR gates comprise a transcriptional repressor and a transcriptional repressor target DNA sequence.

4. The host cell of claim 1, wherein the at least two orthogonal sequence-specific DNA binding polypeptides are selected from the group consisting of transcription factors, transcriptional activators, RNA polymerases, and transcriptional repressors.

5. The host cell of claim 4, wherein the transcriptional repressors are at least 70% identical to the Tetracycline repressor (TetR).

6. The host cell of claim 1, wherein the sequence-specific DNA binding polypeptides are sigma factors.

7. The host cell of claim 1, wherein the host cell is a prokaryotic cell.

* * * * *

SEQUENCE LISTING

<160> NUMBER OF SEQ ID NOS: 244

<210> SEQ ID NO 1
<211> LENGTH: 66
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(66)
<223> OTHER INFORMATION: n = g, a, c or t

<400> SEQUENCE: 1
nnnntaaann tnnnnaaatn annannntnn tgaaacnttt tnnnnnnnna nnncgtataa    60 naaann                                                               66

<210> SEQ ID NO 2
<211> LENGTH: 62
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(62)
<223> OTHER INFORMATION: n = g, a, c or t

<400> SEQUENCE: 2
nnnaannnan aaaaaattnn annnnnnnnn gaacttttcn aatannnnnn agtctaannn    60 ng                                                                   62

<210> SEQ ID NO 3
<211> LENGTH: 69
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(69)
<223> OTHER INFORMATION: n = g, a, c or t

<400> SEQUENCE: 3
antnanaatt ntaatattnt ttanaggtga ttaaacctttt tgtctaaatn atagtctaac   60 accaaanaa                                                            69

<210> SEQ ID NO 4
<211> LENGTH: 48
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(48)
<223> OTHER INFORMATION: n = g, a, c or t

<400> SEQUENCE: 4
nnnnnnnnnn nnntnngna aaatnnnnnn nnntnnntt gtntnncn                   48

<210> SEQ ID NO 5
<211> LENGTH: 68
<212> TYPE: DNA
<213> ORGANISM: Artificial Sequence
<220> FEATURE:
<223> OTHER INFORMATION: synthetic promoter sequence motif

```
<220> FEATURE:
<221> NAME/KEY: modified_base
<222> LOCATION: (1)...(68)
<223> OTHER INFORMATION: n = g, a, c or t

<400> SEQUENCE: 5
nnnnnnnnnn naataattna tannntnnag tgatccaatt tcnacccgc cacgtattaa      60 ntnanana                                                              68

<210> SEQ ID NO 6
<211> LENGTH: 67
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(67)
<223> OTHER INFORMATION: n = g, a, c or t

<400> SEQUENCE: 6
nncggnaanc cnnncagcgg acncgcggcc gggaataaca cggncgccnn cnctgttgnn      60 nggancg                                                               67

<210> SEQ ID NO 7
<211> LENGTH: 69
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(69)
<223> OTHER INFORMATION: n = g, a, c or t

<400> SEQUENCE: 7
tttcccnggt agcgaaangn acagccnggt ttctcaggna aagctcagat tgctcatatc      60
ccgcccata                                                             69

<210> SEQ ID NO 8
<211> LENGTH: 66
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(66)
<223> OTHER INFORMATION: n = g, a, c or t

<400> SEQUENCE: 8
nnnnnnncna caaaannncn cccnncnnnn ggaacnntnn cnncacnnn gcgttncgnn       60 cnnnnn                                                                66

<210> SEQ ID NO 9
<211> LENGTH: 70
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(70)
<223> OTHER INFORMATION: n = g, a, c or t

<400> SEQUENCE: 9
```

-continued

```
agnngcngnt annnaacntt tnggnggcga tgtaaccaan nncgnccnac ncgcgaataa      60 gnnggnaggg                                                             70

<210> SEQ ID NO 10
<211> LENGTH: 67
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(67)
<223> OTHER INFORMATION: n = g, a, c or t

<400> SEQUENCE: 10
gggcnccgcg gcnncncgcn ggncgcgggc tgaaccgaac ngcngccggc gtcgtgtnnn      60
tggcggg                                                                67

<210> SEQ ID NO 11
<211> LENGTH: 68
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(68)
<223> OTHER INFORMATION: n = g, a, c or t

<400> SEQUENCE: 11
cggcnnnngc nncagnnnnn gcgcggnntc tgcatccacn nnnccgnt ncccgtatnn        60 nnanncnn                                                               68

<210> SEQ ID NO 12
<211> LENGTH: 54
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(54)
<223> OTHER INFORMATION: n = g, a, c or t

<400> SEQUENCE: 12
gnnnncnnnn ncngnccccac cgatccnnnn cancnncnnc tccgaatann nnng           54

<210> SEQ ID NO 13
<211> LENGTH: 68
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(68)
<223> OTHER INFORMATION: n = g, a, c or t

<400> SEQUENCE: 13
ncantnncnn naaaannnnn nnattngncc gacggattgn nnnnnnngnn ncgttcaann      60 nncngann                                                               68

<210> SEQ ID NO 14
<211> LENGTH: 70
<212> TYPE: DNA
<213> ORGANISM: Artificial Sequence
```

```
<220> FEATURE:
<223> OTHER INFORMATION: synthetic promoter sequence motif
<220> FEATURE:
<221> NAME/KEY: modified_base
<222> LOCATION: (1)...(70)
<223> OTHER INFORMATION: n = g, a, c or t

<400> SEQUENCE: 14
antanannan ngnnttttt caanacnnca tgcaaccntc ntnnanannn ttgcgtctat      60 nnnaatagaa                                                            70

<210> SEQ ID NO 15
<211> LENGTH: 69
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(69)
<223> OTHER INFORMATION: n = g, a, c or t

<400> SEQUENCE: 15
nnnnanaant tcnaattatt ttagttannn tgtaataatt tncnnntttn nacgactaat      60 nnataaaaa                                                             69

<210> SEQ ID NO 16
<211> LENGTH: 68
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(68)
<223> OTHER INFORMATION: n = g, a, c or t

<400> SEQUENCE: 16
tnatttnatg cntncnanaa atngacaatg tctggaanaa taccaanaga taaaatcatt      60 agatanta                                                              68

<210> SEQ ID NO 17
<211> LENGTH: 66
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(66)
<223> OTHER INFORMATION: n = g, a, c or t

<400> SEQUENCE: 17
tganngagtc tanaatnnga cacnaantcc aggaacaant gtngnaccag nacgtcaaat      60 aaanag                                                                66

<210> SEQ ID NO 18
<211> LENGTH: 68
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(68)
<223> OTHER INFORMATION: n = g, a, c or t
```

-continued

```
<400> SEQUENCE: 18
nnnncnntnn ngnnantttc gncnnnggcg ggaataaact ccgcccnncn ggcgtttnnn    60 cnnnnann                                                             68

<210> SEQ ID NO 19
<211> LENGTH: 52
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(52)
<223> OTHER INFORMATION: n = g, a, c or t

<400> SEQUENCE: 19
nccggnngcn ccnccncnnc gggaacancn nnccctaagc tggngttgnn nn            52

<210> SEQ ID NO 20
<211> LENGTH: 71
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(71)
<223> OTHER INFORMATION: n = g, a, c or t

<400> SEQUENCE: 20
cnncnancng cgcangcann ngnnacnagc cgggaacgcn ngcnccnccc ncgccatcca    60
atgcacggag g                                                         71

<210> SEQ ID NO 21
<211> LENGTH: 71
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(71)
<223> OTHER INFORMATION: n = g, a, c or t

<400> SEQUENCE: 21
tnataaatat ttnaattaat ttanaaattt atgaaacttt ttttaannnt natncgtcta    60
ataaatgtaa a                                                         71

<210> SEQ ID NO 22
<211> LENGTH: 70
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(70)
<223> OTHER INFORMATION: n = g, a, c or t

<400> SEQUENCE: 22
nnnntgtntt tttannnant tnanaaannn ntgaactttt tgntnttnng nggcgtctna    60 tatanagaaa                                                           70

<210> SEQ ID NO 23
<211> LENGTH: 53
```

```
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(53)
<223> OTHER INFORMATION: n = g, a, c or t

<400> SEQUENCE: 23
tnnnnnnncn cctngtnngg gaaccgatcc gtnnntnnnn ccacacagcg ana          53

<210> SEQ ID NO 24
<211> LENGTH: 70
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(70)
<223> OTHER INFORMATION: n = g, a, c or t

<400> SEQUENCE: 24
ccnnnngttt gtancatttt gcnctgccng acgaaacatn tccncnnncc ncgaaaccaa   60
tttcccgaga                                                         70

<210> SEQ ID NO 25
<211> LENGTH: 71
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(71)
<223> OTHER INFORMATION: n = g, a, c or t

<400> SEQUENCE: 25
ttgnaacnna nctttatgtt gcgaaccgnn gacgatagcg ggtngcccnn gngcggtcaa   60
gcnaanaatc c                                                       71

<210> SEQ ID NO 26
<211> LENGTH: 71
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(71)
<223> OTHER INFORMATION: n = g, a, c or t

<400> SEQUENCE: 26
gnncnccccc gcgaccnggt ngnccnggng gtacacccnn ggcggggngg cncgcgtcca   60
actggcgtga c                                                       71

<210> SEQ ID NO 27
<211> LENGTH: 68
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(68)
<223> OTHER INFORMATION: n = g, a, c or t
```

-continued

```
<400> SEQUENCE: 27
cgggcgcncc ngcccgtnc ngcccncccg tcaaccgnnc ccgccgcgcc ngcgtccggn     60 gggngncg                                                            68

<210> SEQ ID NO 28
<211> LENGTH: 69
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(69)
<223> OTHER INFORMATION: n = g, a, c or t

<400> SEQUENCE: 28
nnnnnncngg cnnnnnnnnn cncgcgtcga tgtcacannc gccgggnctg nctcgtcttg     60 tnngcgnaa                                                            69

<210> SEQ ID NO 29
<211> LENGTH: 67
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(67)
<223> OTHER INFORMATION: n = g, a, c or t

<400> SEQUENCE: 29
nngnnncnnc acaaatnntt tngcccggga tgtcgatnnn gcgcnnnccc gttcgtcccn     60 nggntga                                                              67

<210> SEQ ID NO 30
<211> LENGTH: 50
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(50)
<223> OTHER INFORMATION: n = g, a, c or t

<400> SEQUENCE: 30
naaaaatnca tnannggntg aactttnca anannncnna gtctaaannn                50

<210> SEQ ID NO 31
<211> LENGTH: 50
<212> TYPE: DNA
<213> ORGANISM: Artificial Sequence
<220> FEATURE:
<223> OTHER INFORMATION: synthetic promoter sequence motif
<220> FEATURE:
<221> NAME/KEY: modified_base
<222> LOCATION: (1)...(50)
<223> OTHER INFORMATION: n = g, a, c or t

<400> SEQUENCE: 31
nnantancnn nnnntccngt gatccaaacn nncnncagcn ncgtatnana                50

<210> SEQ ID NO 32
<211> LENGTH: 80
<212> TYPE: DNA
<213> ORGANISM: Artificial Sequence
```

<220> FEATURE:
<223> OTHER INFORMATION: synthetic parental promoter sequence

<400> SEQUENCE: 32
tgcgtaattt attcacaagc ttgcatggaa cttgtggata aaatcacggt ctgataaaac    60
agtgaatgat aacctcgttg                                                80

<210> SEQ ID NO 33
<211> LENGTH: 80
<212> TYPE: DNA
<213> ORGANISM: Artificial Sequence
<220> FEATURE:
<223> OTHER INFORMATION: synthetic parental promoter sequence

<400> SEQUENCE: 33
gcctccacac cgctcgtcac atcctgtgat ccactcttca tcccgctacg taacacctct    60
gcatcgcgaa ccaaaaccag                                                80

<210> SEQ ID NO 34
<211> LENGTH: 80
<212> TYPE: DNA
<213> ORGANISM: Artificial Sequence
<220> FEATURE:
<223> OTHER INFORMATION: synthetic chimeric promoter sequence

<400> SEQUENCE: 34
tgcgtaattt attcacaagc ttgcatggaa cttgtggata tcccgctacg taacacctct    60
gcatcgcgaa ccaaaaccag                                                80

<210> SEQ ID NO 35
<211> LENGTH: 80
<212> TYPE: DNA
<213> ORGANISM: Artificial Sequence
<220> FEATURE:
<223> OTHER INFORMATION: synthetic chimeric promoter sequence

<400> SEQUENCE: 35
gcctccacac cgctcgtcac atcctgtgat ccactctata aaatcacggt ctgataaaac    60
agtgaatgat aacctcgttg                                                80

<210> SEQ ID NO 36
<211> LENGTH: 35
<212> TYPE: DNA
<213> ORGANISM: Artificial Sequence
<220> FEATURE:
<223> OTHER INFORMATION: synthetic J23119 promoter and operator sequence
     insert

<400> SEQUENCE: 36
ttgacagcta gctcagtcct aggtataatc gtagc                               35

<210> SEQ ID NO 37
<211> LENGTH: 67
<212> TYPE: DNA
<213> ORGANISM: Artificial Sequence
<220> FEATURE:
<223> OTHER INFORMATION: synthetic inverted repeat sequence
<220> FEATURE:
<221> NAME/KEY: repeat_unit
<222> LOCATION: (3)...(16)
<223> OTHER INFORMATION: 14-mer repeat unit, N-14 through N-1
<220> FEATURE:
<221> NAME/KEY: repeat_unit
<222> LOCATION: (17)...(30)
<223> OTHER INFORMATION: 14-mer repeat unit, N-1 through N-14

```
<220> FEATURE:
<221> NAME/KEY: repeat_unit
<222> LOCATION: (38)...(51)
<223> OTHER INFORMATION: 14-mer repeat unit, N-14 through N-1
<220> FEATURE:
<221> NAME/KEY: repeat_unit
<222> LOCATION: (52)...(65)
<223> OTHER INFORMATION: 14-mer repeat unit, N-1 through N-14
<220> FEATURE:
<221> NAME/KEY: modified_base
<222> LOCATION: (1)...(67)
<223> OTHER INFORMATION: n = g, a, c or t

<400> SEQUENCE: 37
gcnnnnnnnn nnnnnnnnnn nnnnnnnnnn gcgaggcnnn nnnnnnnnnn nnnnnnnnnn    60 nnnnngc                                                               67

<210> SEQ ID NO 38
<211> LENGTH: 12
<212> TYPE: DNA
<213> ORGANISM: Artificial Sequence
<220> FEATURE:
<223> OTHER INFORMATION: synthetic repressor consensus sequence, ButR
      consensus sequence

<400> SEQUENCE: 38
gtgtcactca aa                                                         12

<210> SEQ ID NO 39
<211> LENGTH: 19
<212> TYPE: DNA
<213> ORGANISM: Artificial Sequence
<220> FEATURE:
<223> OTHER INFORMATION: synthetic T7 RNAP N77 scaffold

<400> SEQUENCE: 39
aattgtgagc ggataacaa                                                  19

<210> SEQ ID NO 40
<211> LENGTH: 120
<212> TYPE: DNA
<213> ORGANISM: Artificial Sequence
<220> FEATURE:
<223> OTHER INFORMATION: synthetic T7 RNAP N115 scaffold

<400> SEQUENCE: 40
atgttgttta tcaagcctgc ggatctccgc gaaattgtga cttttccgct atttagcgat    60
cttgttcagt gtggctttcc ttcaccggca gcagattacg ttgaacagcg catcgatctg   120

<210> SEQ ID NO 41
<211> LENGTH: 75
<212> TYPE: DNA
<213> ORGANISM: Artificial Sequence
<220> FEATURE:
<223> OTHER INFORMATION: synthetic T7 RNAP N121 scaffold

<400> SEQUENCE: 41
atgttgttta tcaagcctgc ggatctccgc gaaattgtga cttttccgct atttagcgat    60
cttgttcagt gtggc                                                      75

<210> SEQ ID NO 42
<211> LENGTH: 120
<212> TYPE: DNA
<213> ORGANISM: Artificial Sequence
<220> FEATURE:
<223> OTHER INFORMATION: synthetic T7 RNAP N130 scaffold
```

<400> SEQUENCE: 42
atgttgttta tcaagcctgc ggatctccgc gaaattgtga ctgccgcggc agcgagcgat    60
cttgttcagt gtggctttcc ttcaccggca gcagattacg ttgaacagcg catcgatctg    120

<210> SEQ ID NO 43
<211> LENGTH: 34
<212> TYPE: DNA
<213> ORGANISM: Artificial Sequence
<220> FEATURE:
<223> OTHER INFORMATION: synthetic T7 RNAP N249 scaffold

<400> SEQUENCE: 43
tatccaaacc agtagctcaa ttggagtcgt ctat                                34

<210> SEQ ID NO 44
<211> LENGTH: 40
<212> TYPE: DNA
<213> ORGANISM: Artificial Sequence
<220> FEATURE:
<223> OTHER INFORMATION: synthetic T7 RNAP N249 scaffold random DNA
       spacer

<400> SEQUENCE: 44
tgcagtttta ttctctcgcc agcactgtaa taggcactaa                          40

<210> SEQ ID NO 45
<211> LENGTH: 23
<212> TYPE: DNA
<213> ORGANISM: Artificial Sequence
<220> FEATURE:
<223> OTHER INFORMATION: synthetic T7 promoter sequence motif
<220> FEATURE:
<221> NAME/KEY: modified_base
<222> LOCATION: (16)...(20)
<223> OTHER INFORMATION: n = g, a, c or t

<400> SEQUENCE: 45
taatacgact cactannnnn aga                                            23

<210> SEQ ID NO 46
<211> LENGTH: 23
<212> TYPE: DNA
<213> ORGANISM: Artificial Sequence
<220> FEATURE:
<223> OTHER INFORMATION: synthetic T7 wild-type (WT) promoter sequence

<400> SEQUENCE: 46
taatacgact cactataggg aga                                            23

<210> SEQ ID NO 47
<211> LENGTH: 23
<212> TYPE: DNA
<213> ORGANISM: Artificial Sequence
<220> FEATURE:
<223> OTHER INFORMATION: synthetic T7 Mut1 mutant promoter sequence

<400> SEQUENCE: 47
taatacgact cactacaggc aga                                            23

<210> SEQ ID NO 48
<211> LENGTH: 23
<212> TYPE: DNA
<213> ORGANISM: Artificial Sequence
<220> FEATURE:
<223> OTHER INFORMATION: synthetic T7 Mut2 mutant promoter sequence

```
<400> SEQUENCE: 48
taatacgact cactagagag aga                                             23

<210> SEQ ID NO 49
<211> LENGTH: 23
<212> TYPE: DNA
<213> ORGANISM: Artificial Sequence
<220> FEATURE:
<223> OTHER INFORMATION: synthetic T7 Mut3 mutant promoter sequence

<400> SEQUENCE: 49
taatacgact cactaatggg aga                                             23

<210> SEQ ID NO 50
<211> LENGTH: 23
<212> TYPE: DNA
<213> ORGANISM: Artificial Sequence
<220> FEATURE:
<223> OTHER INFORMATION: synthetic T7 Mut4 mutant promoter sequence

<400> SEQUENCE: 50
taatacgact cactataggt aga                                             23

<210> SEQ ID NO 51
<211> LENGTH: 23
<212> TYPE: DNA
<213> ORGANISM: Artificial Sequence
<220> FEATURE:
<223> OTHER INFORMATION: synthetic T7 Mut5 mutant promoter sequence

<400> SEQUENCE: 51
taatacgact cactaaaggg aga                                             23

<210> SEQ ID NO 52
<211> LENGTH: 23
<212> TYPE: DNA
<213> ORGANISM: Artificial Sequence
<220> FEATURE:
<223> OTHER INFORMATION: synthetic T7 Mut6 mutant promoter sequence

<400> SEQUENCE: 52
taatacgact cactattggg aga                                             23

<210> SEQ ID NO 53
<211> LENGTH: 48
<212> TYPE: DNA
<213> ORGANISM: Artificial Sequence
<220> FEATURE:
<223> OTHER INFORMATION: synthetic transcriptional terminator sequence
      motif
<220> FEATURE:
<221> NAME/KEY: modified_base
<222> LOCATION: (3)...(6)
<223> OTHER INFORMATION: n = g, a, c or t

<400> SEQUENCE: 53
tannnnaacc sswwssssss tcwwwwcgss sssswwssgg tttttgt                   48

<210> SEQ ID NO 54
<211> LENGTH: 29
<212> TYPE: DNA
<213> ORGANISM: Artificial Sequence
<220> FEATURE:
<223> OTHER INFORMATION: synthetic mutant transcriptional terminator 52
      sequence
```

```
<400> SEQUENCE: 54
tataaaacgg ggggctaggg gttttttgt                                    29

<210> SEQ ID NO 55
<211> LENGTH: 48
<212> TYPE: DNA
<213> ORGANISM: Artificial Sequence
<220> FEATURE:
<223> OTHER INFORMATION: synthetic mutant transcriptional terminator 23
      sequence

<400> SEQUENCE: 55
tactcgaacc cctagcccgc tcttatcggg cggctagggg ttttttgt               48

<210> SEQ ID NO 56
<211> LENGTH: 37
<212> TYPE: DNA
<213> ORGANISM: Artificial Sequence
<220> FEATURE:
<223> OTHER INFORMATION: synthetic mutant transcriptional terminator 72
      sequence

<400> SEQUENCE: 56
tagcagaacc gctaacgggg gcgaaggggt tttttgt                           37

<210> SEQ ID NO 57
<211> LENGTH: 48
<212> TYPE: DNA
<213> ORGANISM: Artificial Sequence
<220> FEATURE:
<223> OTHER INFORMATION: synthetic mutant transcriptional terminator 48
      sequence

<400> SEQUENCE: 57
tactcgaacc cctagcccgc tcttatcggg cggctagggg ttttttgt               48

<210> SEQ ID NO 58
<211> LENGTH: 29
<212> TYPE: DNA
<213> ORGANISM: Artificial Sequence
<220> FEATURE:
<223> OTHER INFORMATION: synthetic mutant transcriptional terminator 1
      sequence

<400> SEQUENCE: 58
tacatatcgg gggggtaggg gttttttgt                                    29

<210> SEQ ID NO 59
<211> LENGTH: 29
<212> TYPE: DNA
<213> ORGANISM: Artificial Sequence
<220> FEATURE:
<223> OTHER INFORMATION: synthetic mutant transcriptional terminator 2
      sequence

<400> SEQUENCE: 59
tacatatcgg gggggtaggg gttttttgt                                    29

<210> SEQ ID NO 60
<211> LENGTH: 48
<212> TYPE: DNA
<213> ORGANISM: Artificial Sequence
<220> FEATURE:
<223> OTHER INFORMATION: synthetic wild-type (WT) transcriptiona
      terminator sequence

<400> SEQUENCE: 60
```
tagcataacc ccttggggcc tctaaacggg tcttgagggg ttttttgt    48

<210> SEQ ID NO 61
<211> LENGTH: 47
<212> TYPE: DNA
<213> ORGANISM: Artificial Sequence
<220> FEATURE:
<223> OTHER INFORMATION: synthetic mutant transcriptional terminator 31
      sequence

<400> SEQUENCE: 61
taccctaacc ccttccccgg tcaatcgggg cggatggggt ttttgt    47

<210> SEQ ID NO 62
<211> LENGTH: 47
<212> TYPE: DNA
<213> ORGANISM: Artificial Sequence
<220> FEATURE:
<223> OTHER INFORMATION: synthetic mutant transcriptional terminator 58
      sequence

<400> SEQUENCE: 62
tagaccaacc ccttgcggcc tcaatcgggg gggatggggt ttttgt    47

<210> SEQ ID NO 63
<211> LENGTH: 37
<212> TYPE: DNA
<213> ORGANISM: Artificial Sequence
<220> FEATURE:
<223> OTHER INFORMATION: synthetic mutant transcriptional terminator 25
      sequence

<400> SEQUENCE: 63
tactctaacc ccatcggccg tcttaggggt ttttgt    37

<210> SEQ ID NO 64
<211> LENGTH: 48
<212> TYPE: DNA
<213> ORGANISM: Artificial Sequence
<220> FEATURE:
<223> OTHER INFORMATION: synthetic mutant transcriptional terminator 17
      sequence

<400> SEQUENCE: 64
tacctcaacc ccttccgccc tcatatcgcg gggcatgcgg ttttttgt    48

<210> SEQ ID NO 65
<211> LENGTH: 39
<212> TYPE: PRT
<213> ORGANISM: Artificial Sequence
<220> FEATURE:
<223> OTHER INFORMATION: synthetic T7 RNAP specificity loop sequence

<400> SEQUENCE: 65

Val Trp Gln Glu Tyr Lys Lys Pro Ile Gln Thr Arg Leu Asn Leu Met
1               5                   10                  15

Phe Leu Gly Gln Phe Arg Leu Gln Pro Thr Ile Asn Thr Asn Lys Asp
            20                  25                  30

Ser Glu Ile Asp Ala His Lys
        35

<210> SEQ ID NO 66
<211> LENGTH: 39
<212> TYPE: PRT
<213> ORGANISM: Artificial Sequence

```
<220> FEATURE:
<223> OTHER INFORMATION: synthetic T3 RNAP specificity loop sequence

<400> SEQUENCE: 66

Val Trp Gln Glu Tyr Lys Lys Pro Ile Gln Lys Arg Leu Asp Met Ile
1               5                   10                  15

Phe Leu Gly Gln Phe Arg Leu Gln Pro Thr Ile Asn Thr Asn Lys Asp
            20                  25                  30

Ser Glu Ile Asp Ala His Lys
        35

<210> SEQ ID NO 67
<211> LENGTH: 23
<212> TYPE: DNA
<213> ORGANISM: Artificial Sequence
<220> FEATURE:
<223> OTHER INFORMATION: synthetic T3 promoter sequence

<400> SEQUENCE: 67
taataaccct cactataggg aga                                           23

<210> SEQ ID NO 68
<211> LENGTH: 39
<212> TYPE: PRT
<213> ORGANISM: Artificial Sequence
<220> FEATURE:
<223> OTHER INFORMATION: synthetic K1F RNAP specificity loop sequence

<400> SEQUENCE: 68

Val Trp Gln Glu Tyr Lys Lys Pro Ile Gln Thr Arg Leu Asn Leu Met
1               5                   10                  15

Phe Leu Gly Ser Phe Asn Leu Gln Pro Thr Val Asn Thr Asn Lys Asp
            20                  25                  30

Ser Glu Ile Asp Ala His Lys
        35

<210> SEQ ID NO 69
<211> LENGTH: 23
<212> TYPE: DNA
<213> ORGANISM: Artificial Sequence
<220> FEATURE:
<223> OTHER INFORMATION: synthetic K1F promoter sequence

<400> SEQUENCE: 69
taataactat cactataggg aga                                           23

<210> SEQ ID NO 70
<211> LENGTH: 39
<212> TYPE: PRT
<213> ORGANISM: Artificial Sequence
<220> FEATURE:
<223> OTHER INFORMATION: synthetic N4 RNAP specificity loop sequence

<400> SEQUENCE: 70

Val Trp Gln Glu Tyr Lys Lys Pro Ile Gln Thr Arg Ile Asp Cys Val
1               5                   10                  15

Ile Leu Gly Thr His Arg Met Ala Leu Thr Ile Asn Thr Asn Lys Asp
            20                  25                  30

Ser Glu Ile Asp Ala His Lys
        35

<210> SEQ ID NO 71
<211> LENGTH: 23
```

```
<212> TYPE: DNA
<213> ORGANISM: Artificial Sequence
<220> FEATURE:
<223> OTHER INFORMATION: synthetic N4 promoter sequence

<400> SEQUENCE: 71
taataaccca cactataggg aga                                          23

<210> SEQ ID NO 72
<211> LENGTH: 15
<212> TYPE: DNA
<213> ORGANISM: Artificial Sequence
<220> FEATURE:
<223> OTHER INFORMATION: synthetic partial T7 promoter sequence

<400> SEQUENCE: 72
taatacgact cacta                                                   15

<210> SEQ ID NO 73
<211> LENGTH: 23
<212> TYPE: DNA
<213> ORGANISM: Artificial Sequence
<220> FEATURE:
<223> OTHER INFORMATION: synthetic T7:Mut1 promoter sequence

<400> SEQUENCE: 73
taatacgact cactacaggc aga                                          23

<210> SEQ ID NO 74
<211> LENGTH: 23
<212> TYPE: DNA
<213> ORGANISM: Artificial Sequence
<220> FEATURE:
<223> OTHER INFORMATION: synthetic T7:Mut2 promoter sequence

<400> SEQUENCE: 74
taatacgact cactagagag aga                                          23

<210> SEQ ID NO 75
<211> LENGTH: 23
<212> TYPE: DNA
<213> ORGANISM: Artificial Sequence
<220> FEATURE:
<223> OTHER INFORMATION: synthetic T7:Mut3 promoter sequence

<400> SEQUENCE: 75
taatacgact cactaatggg aga                                          23

<210> SEQ ID NO 76
<211> LENGTH: 23
<212> TYPE: DNA
<213> ORGANISM: Artificial Sequence
<220> FEATURE:
<223> OTHER INFORMATION: synthetic T7:Mut4 promoter sequence

<400> SEQUENCE: 76
taatacgact cactataggt aga                                          23

<210> SEQ ID NO 77
<211> LENGTH: 23
<212> TYPE: DNA
<213> ORGANISM: Artificial Sequence
<220> FEATURE:
<223> OTHER INFORMATION: synthetic T7:Mut5 promoter sequence

<400> SEQUENCE: 77
```
taatacgact cactaaaggg aga                                             23

<210> SEQ ID NO 78
<211> LENGTH: 23
<212> TYPE: DNA
<213> ORGANISM: Artificial Sequence
<220> FEATURE:
<223> OTHER INFORMATION: synthetic T7:Mut6 promoter sequence

<400> SEQUENCE: 78
taatacgact cactattggg aga                                             23

<210> SEQ ID NO 79
<211> LENGTH: 23
<212> TYPE: DNA
<213> ORGANISM: Artificial Sequence
<220> FEATURE:
<223> OTHER INFORMATION: synthetic T3:Mut1 promoter sequence

<400> SEQUENCE: 79
taataaccct cactacaggc aga                                             23

<210> SEQ ID NO 80
<211> LENGTH: 23
<212> TYPE: DNA
<213> ORGANISM: Artificial Sequence
<220> FEATURE:
<223> OTHER INFORMATION: synthetic T3:Mut2 promoter sequence

<400> SEQUENCE: 80
taataaccct cactagagag aga                                             23

<210> SEQ ID NO 81
<211> LENGTH: 23
<212> TYPE: DNA
<213> ORGANISM: Artificial Sequence
<220> FEATURE:
<223> OTHER INFORMATION: synthetic T3:Mut3 promoter sequence

<400> SEQUENCE: 81
taataaccct cactaatggg aga                                             23

<210> SEQ ID NO 82
<211> LENGTH: 23
<212> TYPE: DNA
<213> ORGANISM: Artificial Sequence
<220> FEATURE:
<223> OTHER INFORMATION: synthetic T3:Mut4 promoter sequence

<400> SEQUENCE: 82
taataaccct cactataggt aga                                             23

<210> SEQ ID NO 83
<211> LENGTH: 23
<212> TYPE: DNA
<213> ORGANISM: Artificial Sequence
<220> FEATURE:
<223> OTHER INFORMATION: synthetic T3:Mut5 promoter sequence

<400> SEQUENCE: 83
taataaccct cactaaaggg aga                                             23

<210> SEQ ID NO 84
<211> LENGTH: 23
<212> TYPE: DNA
<213> ORGANISM: Artificial Sequence

```
<220> FEATURE:
<223> OTHER INFORMATION: synthetic T3:Mut6 promoter sequence

<400> SEQUENCE: 84
taataaccct cactattggg aga                                              23

<210> SEQ ID NO 85
<211> LENGTH: 12
<212> TYPE: DNA
<213> ORGANISM: Artificial Sequence
<220> FEATURE:
<223> OTHER INFORMATION: synthetic AmeR repressor consensus sequence
<220> FEATURE:
<221> NAME/KEY: modified_base
<222> LOCATION: (9)...(9)
<223> OTHER INFORMATION: n = g, a, c or t

<400> SEQUENCE: 85
tagtgacgnt ta                                                          12

<210> SEQ ID NO 86
<211> LENGTH: 14
<212> TYPE: DNA
<213> ORGANISM: Artificial Sequence
<220> FEATURE:
<223> OTHER INFORMATION: synthetic JadR2 repressor consensus sequence
<220> FEATURE:
<221> NAME/KEY: modified_base
<222> LOCATION: (7)...(8)
<223> OTHER INFORMATION: n = g, a, c or t

<400> SEQUENCE: 86
agatacnngt atct                                                        14

<210> SEQ ID NO 87
<211> LENGTH: 12
<212> TYPE: DNA
<213> ORGANISM: Artificial Sequence
<220> FEATURE:
<223> OTHER INFORMATION: synthetic ArpA repressor consensus sequence

<400> SEQUENCE: 87
tccacatgta gc                                                          12

<210> SEQ ID NO 88
<211> LENGTH: 12
<212> TYPE: DNA
<213> ORGANISM: Artificial Sequence
<220> FEATURE:
<223> OTHER INFORMATION: synthetic CasR repressor consensus sequence

<400> SEQUENCE: 88
tgagtactgt aa                                                          12

<210> SEQ ID NO 89
<211> LENGTH: 10
<212> TYPE: DNA
<213> ORGANISM: Artificial Sequence
<220> FEATURE:
<223> OTHER INFORMATION: synthetic LitR repressor consensus sequence

<400> SEQUENCE: 89
gcttatatgc                                                             10

<210> SEQ ID NO 90
<211> LENGTH: 18
<212> TYPE: DNA
```

```
<213> ORGANISM: Artificial Sequence
<220> FEATURE:
<223> OTHER INFORMATION: synthetic BarA repressor consensus sequence

<400> SEQUENCE: 90
gcacgatcat gatcgtgc                                                    18

<210> SEQ ID NO 91
<211> LENGTH: 12
<212> TYPE: DNA
<213> ORGANISM: Artificial Sequence
<220> FEATURE:
<223> OTHER INFORMATION: synthetic DhaR repressor consensus sequence

<400> SEQUENCE: 91
acggcatgta tc                                                          12

<210> SEQ ID NO 92
<211> LENGTH: 12
<212> TYPE: DNA
<213> ORGANISM: Artificial Sequence
<220> FEATURE:
<223> OTHER INFORMATION: synthetic McbR repressor consensus sequence
<220> FEATURE:
<221> NAME/KEY: modified_base
<222> LOCATION: (2)...(2)
<223> OTHER INFORMATION: n = g, a, c or t

<400> SEQUENCE: 92
tntagacaga cc                                                          12

<210> SEQ ID NO 93
<211> LENGTH: 12
<212> TYPE: DNA
<213> ORGANISM: Artificial Sequence
<220> FEATURE:
<223> OTHER INFORMATION: synthetic BarB repressor consensus sequence
<220> FEATURE:
<221> NAME/KEY: modified_base
<222> LOCATION: (2)...(10)
<223> OTHER INFORMATION: n = g, a, c or t

<400> SEQUENCE: 93
gcngaataan at                                                          12

<210> SEQ ID NO 94
<211> LENGTH: 12
<212> TYPE: DNA
<213> ORGANISM: Artificial Sequence
<220> FEATURE:
<223> OTHER INFORMATION: synthetic EnvR repressor consensus sequence

<400> SEQUENCE: 94
ggccaatgag ta                                                          12

<210> SEQ ID NO 95
<211> LENGTH: 12
<212> TYPE: DNA
<213> ORGANISM: Artificial Sequence
<220> FEATURE:
<223> OTHER INFORMATION: synthetic repressor consensus sequence

<400> SEQUENCE: 95
agactagaca ga                                                          12

<210> SEQ ID NO 96
<211> LENGTH: 18
```

```
<212> TYPE: DNA
<213> ORGANISM: Artificial Sequence
<220> FEATURE:
<223> OTHER INFORMATION: synthetic degenerate ribosomal binding site
      (RBS) library

<400> SEQUENCE: 96
tcacacggaa akrcywsg                                                   18

<210> SEQ ID NO 97
<211> LENGTH: 206
<212> TYPE: PRT
<213> ORGANISM: Artificial Sequence
<220> FEATURE:
<223> OTHER INFORMATION: synthetic chimeric sigma factor ECF11_ECF02

<400> SEQUENCE: 97
```

Met Arg Ile Thr Ala Ser Leu Arg Thr Phe Cys His Leu Ser Thr Pro
1               5                   10                  15

His Ser Asp Ser Thr Thr Ser Arg Leu Trp Ile Asp Glu Val Thr Ala
            20                  25                  30

Val Ala Arg Gln Arg Asp Arg Asp Ser Phe Met Arg Ile Tyr Asp His
        35                  40                  45

Phe Ala Pro Arg Leu Leu Arg Tyr Leu Thr Gly Leu Asn Val Pro Glu
    50                  55                  60

Gly Gln Ala Glu Glu Leu Val Gln Glu Val Leu Leu Lys Leu Trp His
65                  70                  75                  80

Lys Ala Glu Ser Phe Asp Pro Ser Lys Ala Ser Leu Gly Thr Trp Leu
                85                  90                  95

Phe Arg Ile Ala Arg Asn Leu Tyr Ile Asp Ser Val Arg Lys Asp Arg
            100                 105                 110

Gly Trp Val Gln Val Gln Asn Ser Leu Glu Gln Leu Glu Arg Leu Glu
        115                 120                 125

Ala Ile Ser Asn Pro Glu Asn Leu Met Leu Ser Glu Glu Leu Arg Gln
    130                 135                 140

Ile Val Phe Arg Thr Ile Glu Ser Leu Pro Glu Asp Leu Arg Met Ala
145                 150                 155                 160

Ile Thr Leu Arg Glu Leu Asp Gly Leu Ser Tyr Glu Glu Ile Ala Ala
                165                 170                 175

Ile Met Asp Cys Pro Val Gly Thr Val Arg Ser Arg Ile Phe Arg Ala
            180                 185                 190

Arg Glu Ala Ile Asp Asn Lys Val Gln Pro Leu Ile Arg Arg
        195                 200                 205

```
<210> SEQ ID NO 98
<211> LENGTH: 187
<212> TYPE: PRT
<213> ORGANISM: Artificial Sequence
<220> FEATURE:
<223> OTHER INFORMATION: synthetic chimeric sigma factor ECF02_ECF11

<400> SEQUENCE: 98
```

Met Ser Glu Gln Leu Thr Asp Gln Val Leu Val Glu Arg Val Gln Lys
1               5                   10                  15

Gly Asp Gln Lys Ala Phe Asn Leu Leu Val Val Arg Tyr Gln His Lys
            20                  25                  30

Val Ala Ser Leu Val Ser Arg Tyr Val Pro Ser Gly Asp Val Pro Asp
        35                  40                  45

Val Val Gln Glu Ala Phe Ile Lys Ala Tyr Arg Ala Leu Asp Ser Phe

```
            50                  55                  60
Arg Gly Asp Ser Ala Phe Tyr Thr Trp Leu Tyr Arg Ile Ala Val Asn
 65                  70                  75                  80

Thr Ala Lys Asn Tyr Leu Val Ala Gln Gly Arg Arg Pro Pro Ser Ser
                     85                  90                  95

Asp Val Asp Ala Ile Glu Ala Glu Asn Phe Glu Gln Leu Glu Arg Leu
                    100                 105                 110

Glu Ala Pro Val Asp Arg Thr Leu Asp Tyr Ser Gln Arg Gln Glu Gln
                115                 120                 125

Gln Leu Asn Ser Ala Ile Gln Asn Leu Pro Thr Asp Gln Ala Lys Val
            130                 135                 140

Leu Arg Met Ser Tyr Phe Glu Ala Leu Ser His Arg Glu Ile Ser Glu
145                 150                 155                 160

Arg Leu Asp Met Pro Leu Gly Thr Val Lys Ser Cys Leu Arg Leu Ala
                165                 170                 175

Phe Gln Lys Leu Arg Ser Arg Ile Glu Glu Ser
                180                 185
```

<210> SEQ ID NO 99
<211> LENGTH: 883
<212> TYPE: PRT
<213> ORGANISM: Enterobacteria phage T7
<220> FEATURE:
<223> OTHER INFORMATION: bacteriophage T7 RNA polymerase (RNAP)

<400> SEQUENCE: 99

```
Met Asn Thr Ile Asn Ile Ala Lys Asn Asp Phe Ser Asp Ile Glu Leu
  1               5                  10                  15

Ala Ala Ile Pro Phe Asn Thr Leu Ala Asp His Tyr Gly Glu Arg Leu
                 20                  25                  30

Ala Arg Glu Gln Leu Ala Leu Glu His Glu Ser Tyr Glu Met Gly Glu
             35                  40                  45

Ala Arg Phe Arg Lys Met Phe Glu Arg Gln Leu Lys Ala Gly Glu Val
         50                  55                  60

Ala Asp Asn Ala Ala Ala Lys Pro Leu Ile Thr Thr Leu Leu Pro Lys
 65                  70                  75                  80

Met Ile Ala Arg Ile Asn Asp Trp Phe Glu Glu Val Lys Ala Lys Arg
                 85                  90                  95

Gly Lys Arg Pro Thr Ala Phe Gln Phe Leu Gln Glu Ile Lys Pro Glu
                100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
        130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
        210                 215                 220

Gly Met Val Ser Leu His Arg Gln Asn Ala Gly Val Val Gly Gln Asp
```

```
            225                 230                 235                 240

Ser Glu Thr Ile Glu Leu Ala Pro Tyr Ala Glu Ala Ile Ala Thr
                245                 250                 255

Arg Ala Gly Ala Leu Ala Gly Ile Ser Pro Met Phe Gln Pro Cys Val
                    260                 265                 270

Val Pro Pro Lys Pro Trp Thr Gly Ile Thr Gly Gly Tyr Trp Ala
                275                 280                 285

Asn Gly Arg Arg Pro Leu Ala Leu Val Arg Thr His Ser Lys Lys Ala
                    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                    325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
                370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                    405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                    435                 440                 445

Gly Lys Pro Ile Gly Lys Glu Gly Tyr Tyr Trp Leu Lys Ile His Gly
                450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                    485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His His Gly Leu Ser Tyr
                515                 520                 525

Asn Cys Ser Leu Pro Leu Ala Phe Asp Gly Ser Cys Ser Gly Ile Gln
                530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                    565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
                    595                 600                 605

Val Lys Leu Gly Thr Lys Ala Leu Ala Gly Gln Trp Leu Ala Tyr Gly
                610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                    645                 650                 655
```

```
Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
            770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
        850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 100
<211> LENGTH: 498
<212> TYPE: DNA
<213> ORGANISM: Salmonella typhimurium
<220> FEATURE:
<223> OTHER INFORMATION: transcriptional activator chaperone protein
      sicA

<400> SEQUENCE: 100
atggattatc aaaataatgt cagcgaagaa cgtgttgcgg aaatgatttg ggatgccgtt     60
agtgaaggcg ccacgctaaa agacgttcat gggatccctc aagatatgat ggacggttta    120
tatgctcatg cttatgagtt tttataaccag ggacgactgg atgaagctga cgttctttt    180 cgtttcttat gcatttatga ttttacaat cccgattaca ccatgggact ggcggcagta    240
tgccaactga aaaacaatt tcagaaagca tgtgaccttt atgcagtagc gtttacgtta    300
cttaaaaatg attatcgccc cgtttttttt accggcagt gtcaattatt aatgcgtaag    360
gcagcaaaag ccagacagtg ttttgaactt gtcaatgaac gtactgaaga tgagtctctg    420
cgggcaaaag cgttggtcta tctggaggcg ctaaaaacgg cggagacaga gcagcacagt    480
gaacaagaaa aggaataa                                                 498

<210> SEQ ID NO 101
<211> LENGTH: 498
<212> TYPE: DNA
<213> ORGANISM: Artificial Sequence
```

<220> FEATURE:
<223> OTHER INFORMATION: synthetic sicA* F62Y mutant sicA transcriptional activator chaperone protein

<400> SEQUENCE: 101

| | |
|---|---|
| atggattatc aaaataatgt cagcgaagaa cgtgttgcgg aaatgatttg ggatgccgtt | 60 |
| agtgaaggcg ccacgctaaa agacgttcat gggatccctc aagatatgat ggacggttta | 120 |
| tatgctcatg cttatgagtt ttataaccag ggacgactgg atgaagctga dacgttcttt | 180 |
| cgttacttat gcatttatga ttttttacaat cccgattaca ccatgggact ggcggcagta | 240 |
| tgccaactga aaaacaatt tcagaaagca tgtgaccttt atgcagtagc gtttacgtta | 300 |
| cttaaaaatg attatcgccc cgtttttttt accgggcagt gtcaattatt aatgcgtaag | 360 |
| gcagcaaaag ccagacagtg tttttgaactt gtcaatgaac gtactgaaga tgagtctctg | 420 |
| cgggcaaaag cgttggtcta tctggaggcg ctaaaaacgg cggagacaga gcagcacagt | 480 |
| gaacaagaaa aggaataa | 498 |

<210> SEQ ID NO 102
<211> LENGTH: 750
<212> TYPE: DNA
<213> ORGANISM: Salmonella typhimurium
<220> FEATURE:
<223> OTHER INFORMATION: transcriptional activator invF with new corrected upstream start codon

<400> SEQUENCE: 102

| | |
|---|---|
| atgctaaata cgcaggaagt acttaaagaa ggagagaagc ggaaaatccg cagcccggaa | 60 |
| gcatggttta tacagacgtg ttccgcgcaa aagctgcata tgtcattttc tgaaagccga | 120 |
| cacaatgaaa attgcctgat tcaggaaggc gcgctgcttt tttgcgagca ggccgttgtc | 180 |
| gcaccagtat caggagacct ggttttttcga ccgttaaaaa ttgaagtact cagcaaatta | 240 |
| ctggcatttta tcgatggcgc aggattagtg gacacgacat atgctgaatc cgataaatgg | 300 |
| gttttgctga gtcctgagtt tcgcgctatt tggcaagatc gtaaacgctg cgagtactgg | 360 |
| ttttttgcagc aaaattattac gccttctccg gccttcaata aggtactggc gctgttacga | 420 |
| aaaagcgaga gttactggtt ggttggctat ttactcgctc agtcaaccag cggcaacacg | 480 |
| atgagaatgc tgggagaaga ctatggcgtt tcttatacc attttcgtcg tttgtgcagc | 540 |
| agagcgttgg gcgaaaaagc gaagagtgaa ttacgaaact ggcgtatggc gcaatcgctg | 600 |
| ctgaatagtg tagaaggcca cgagaacatc acccaattag ccgttaatca tggttactca | 660 |
| tcgccttcac attttctag tgagatcaaa gagctgatcg gcgtttcgcc gcggaaatta | 720 |
| tcaaatatta ttcaattggc agacaaatga | 750 |

<210> SEQ ID NO 103
<211> LENGTH: 163
<212> TYPE: DNA
<213> ORGANISM: Salmonella typhimurium
<220> FEATURE:
<221> NAME/KEY: promoter
<222> LOCATION: (1)...(163)
<223> OTHER INFORMATION: psicA promoter

<400> SEQUENCE: 103

| | |
|---|---|
| ccacaagaaa cgaggtacgg cattgagccg cgtaaggcag tagcgatgta ttcattgggc | 60 |
| gttttttgaa tgttcactaa ccaccgtcgg ggtttaataa ctgcatcaga taaacgcagt | 120 |
| cgttaagttc tacaaagtcg gtgacagata acaggagtaa gta | 163 |

<210> SEQ ID NO 104
<211> LENGTH: 468
<212> TYPE: DNA
<213> ORGANISM: Shigella flexneri
<220> FEATURE:
<223> OTHER INFORMATION: transcriptional activator chaperone protein
      ipgC

<400> SEQUENCE: 104

| | | |
|---|---|---|
| atgtctttaa atatcaccga aaatgaaagc atctctactg cagtaattga tgcaattaac | 60 |
| tctggcgcta cactgaaaga tattaatgca attcctgatg atatgatgga tgacatttat | 120 |
| tcatatgctt atgactttta caacaaagga agaatagagg aagctgaagt tttcttcagg | 180 |
| tttttatgta tatacgactt ttacaatgta gactacatta tgggactcgc agctatttat | 240 |
| cagataaaag aacagttcca acaagcagca gacctttatg ctgtcgcttt tgcattagga | 300 |
| aaaaatgact ataccagt attccatact ggacaatgtc agcttcggtt gaaagccccc | 360 |
| ttaaaagcta aagagtgctt cgaactcgta attcaacaca gcaatgatga aaaattaaaa | 420 |
| ataaaagcac aatcatactt ggacgcaatt caggatatca aggagtaa | 468 |

<210> SEQ ID NO 105
<211> LENGTH: 756
<212> TYPE: DNA
<213> ORGANISM: Artificial Sequence
<220> FEATURE:
<223> OTHER INFORMATION: synthetic Shigella flexneri transcriptional
      activator mxiE with codon optimization

<400> SEQUENCE: 105

| | | |
|---|---|---|
| atgagtaaat ataaaggcct gaacaccagc aacatgttct acatctacag ctctggtcat | 60 |
| gaaccggtga acgttgaact ggtgaaagat aagaacgta acatcatcga actggcaccg | 120 |
| gcgtggaaag cttttttctt tgtgcgtaac cagaacatca aattcagcga taacgttaac | 180 |
| taccactacc gcttcaacat caactcttgc gcaaaattcc tggcgttttg ggattatttt | 240 |
| agcggcgccc tggttgaaca ttctcacgca gaaaaatgca tccatttcta ccacgaaaac | 300 |
| gatctgcgtg atagctgtaa tacggaatct atgctggata aactgatgct gcgcttcatt | 360 |
| tttagtagcg atcagaacgt gtctaatgcc ctggcaatga tccgtatgac cgaaagttat | 420 |
| catctggttc tgtacctgct gcgtacgatt gaaaaagaaa aagaagtgcg catcaaaagc | 480 |
| ctgaccgaac actatggcgt ttctgaagcg tactttcgta gtctgtgtcg caaagcgctg | 540 |
| ggtgccaaag tgaaagaaca gctgaacacg tggcgcctgg tgaatggcct gctggatgtt | 600 |
| ttcctgcata accagaccat tacgagcgcg gccatgaaca tggttatgc gtctaccagt | 660 |
| cacttcagca tgaaaattaa aacgcgtctg ggctttagtg cccgcgaact gagcaacatc | 720 |
| accttcctgg tgaagaaaat taatgaaaaa atctaa | 756 |

<210> SEQ ID NO 106
<211> LENGTH: 350
<212> TYPE: DNA
<213> ORGANISM: Shigella flexneri
<220> FEATURE:
<221> NAME/KEY: promoter
<222> LOCATION: (1)...(350)
<223> OTHER INFORMATION: pipaH9.8 promoter

<400> SEQUENCE: 106

| | | |
|---|---|---|
| gcgaaaatga catcaaaaac gccattaacc tgatgttctg gggaatataa atgtcaggct | 60 |
| agggtcaaaa atcgtggcgt tgacaaaatg gctgcgttac gtcattgagc atatccagga | 120 |

```
ctggccggca aaccgggtac gcgatctgtt gccttggaaa gttgatctga cctctcagta    180
aatatcaata cggttctgac gagccgctta ccgttcaaat atgaagtacg atgtttaact    240
aaccgaaaaa caagaacaat acggtgcaaa caggccattc acggttaact gaaacagtat    300
cgttttttta cagccaattt tgtttatcct tattataata aaaaagtgct              350
```

<210> SEQ ID NO 107
<211> LENGTH: 350
<212> TYPE: DNA
<213> ORGANISM: Artificial Sequence
<220> FEATURE:
<223> OTHER INFORMATION: synthetic mutated pipaH9.8 Shigella flexneri
      promoter pipaH9.8*

<400> SEQUENCE: 107

```
gcgaaaatga catcaaaaac gccattaacc tgatgttctg gggaatataa atgtcaggct     60
agggtcaaaa atcgtggcgt tgacaaaatg gctgcgttac gtcattgagc atatccagga    120
ctggccggca aaccgggtac gcgatctgtt gccttggaaa gttgatctga cctctcagta    180
aatatcaata cggttctgac gagccgctta ccgttcaaat atgaagtacg atgtttaact    240
aaccgaaaaa caagaacaat acggtgcaaa caggccattc acggttaact gaaacagtat    300
cgttttttta cagccaattt tgtttatcct tattaagata aaaaagtgct              350
```

<210> SEQ ID NO 108
<211> LENGTH: 438
<212> TYPE: DNA
<213> ORGANISM: Pseudomonas aeruginosa
<220> FEATURE:
<223> OTHER INFORMATION: transcriptional activator chaperone protein
      exsC

<400> SEQUENCE: 108

```
atggatttaa cgagcaaggt caaccgactg cttgccgagt tcgcaggccg tatcggtttg     60
ccttccctgt ccctcgacga ggagggcatg gcgagcctcc tgttcgacga acaggtgggc    120
gtcaccctgt gctgctcgc cgagcgcgag cgtctgttgc tggaggccga tgtggcgggc    180
atcgatgtgc tgggcgaggg gatctttcgc cagctcgcca gcttcaaccg ccattggcac    240
cgtttcgatc tgcatttcgg cttcgacgag ctgaccggca aggtccagtt gtatgcgcag    300
attctcgcag cgcaactgac cctcgaatgc ttcgaggcga ccttggccaa tctgctcgat    360
cacgccgagt tctggcagcg cctgctgccg tgcgacagtg atcgcgaggc ggtcgctgcg    420
gtcggcatga gggtttga                                                 438
```

<210> SEQ ID NO 109
<211> LENGTH: 831
<212> TYPE: DNA
<213> ORGANISM: Pseudomonas aeruginosa
<220> FEATURE:
<223> OTHER INFORMATION: exsD

<400> SEQUENCE: 109

```
atggagcagg aagacgataa gcagtactcc cgagaagcgg tgttcgctgg caggcgggta     60
tccgtggtgg gctcggacgc ccgctcgcgg ggtcgggtgc cggttacgc atcgagcagt    120 ttgtatcgtg agtccggaat catcagtgcg cggcaactgg cgttgctgca gcggatgctg    180
ccgcgcctgc ggctggagca actgttccgc tgcgagtggt tgcagcagcg cctggcgcgc    240
ggcctggcgc tggggcgcga agaggtgcgg cagattctcc tctgcgcggc gcaggacgac    300
```

```
gacggctggt gctccgaact gggcgaccgg gtcaacctcg ccgtgccgca gtcgatgatc    360
gactgggtcc tgctgccggt ctatggctgg tgggaaagcc tgctcgacca ggcgatcccc    420
ggctggcgcc tgtcgctggt ggagctggag acccagtccc ggcaactgcg agtcaagtcc    480
gaattctggt cccgcgtggc cgagctggag ccggagcagg cccgcgagga actggccagg    540
gtcgccaagt gccaggcgcg cacccaggaa caggtggccg aactggccgg caagctggag    600
acggcttcgg cactggcgaa gagcgcctgg ccgaactggc agcggggcat ggcgacgctg    660
ctcgccagcg gcgggctggc cggcttcgag ccgatccccg aggtcctcga atgcctctgg    720
caacctctct gccggctgga cgacgacgtc ggcgcggcgg acgccgtcca ggcctggctg    780
cacgaacgca acctgtgcca ggcacaggat cacttctact ggcagagctg a            831
```

```
<210> SEQ ID NO 110
<211> LENGTH: 837
<212> TYPE: DNA
<213> ORGANISM: Pseudomonas aeruginosa
<220> FEATURE:
<223> OTHER INFORMATION: transcriptional activator exsA

<400> SEQUENCE: 110
atgcaaggag ccaaatctct tggccgaaag cagataacgt cttgtcattg gaacattcca     60
actttcgaat acagggtaaa caaggaagag ggcgtatatg ttctgctcga gggcgaactg    120
accgtccagg acatcgattc cacttttttgc ctggcgcctg gcgagttgct tttcgtccgc    180
cgcggaagct atgtcgtaag taccaaggga aggacagcc gaatactctg gattccatta    240 tctgccagt ttctacaagg cttcgtccag cgcttcggcg cgctgttgag tgaagtcgag    300
cgttgcgacg agcccgtgcc gggcatcatc gcgttcgctg ccacgcctct gctggccggt    360
tgcgtcaagg ggttgaagga attgcttgtg catgagcatc cgccgatgct cgcctgcctg    420
aagatcgagg agttgctgat gctcttcgcg ttcagtccgc aggggccgct gctgatgtcg    480
gtcctgcggc aactgagcaa ccggcatgtc gagcgtctgc agctattcat ggagaagcac    540
tacctcaacg agtggaagct gtccgacttc tcccgcgagt tcggcatggg gctgaccacc    600
ttcaaggagc tgttcggcag tgtctatggg gtttcgccgc gcgcctggat cagcgagcgg    660
agaatcctct atgcccatca gttgctgctc aacagcgaca tgagcatcgt cgacatcgcc    720
atggaggcgg gcttttccag tcagtcctat ttcacccaga gctatcgccg ccgtttcggc    780
tgcacgccga gccgctcgcg gcaggggaag gacgaatgcc gggctaaaaa taactga      837
```

```
<210> SEQ ID NO 111
<211> LENGTH: 80
<212> TYPE: DNA
<213> ORGANISM: Pseudomonas aeruginosa
<220> FEATURE:
<221> NAME/KEY: promoter
<222> LOCATION: (1)...(80)
<223> OTHER INFORMATION: pexsD promoter

<400> SEQUENCE: 111
gaaggacgaa tgccgggcta aaaataactg acgttttttg aaagcccggt agcggctgca     60
tgagtagaat cggcccaaat                                                 80
```

```
<210> SEQ ID NO 112
<211> LENGTH: 80
<212> TYPE: DNA
<213> ORGANISM: Pseudomonas aeruginosa
<220> FEATURE:
<221> NAME/KEY: promoter
```

```
<222> LOCATION: (1)...(80)
<223> OTHER INFORMATION: pexsC promoter

<400> SEQUENCE: 112
gatgtggctt ttttcttaaa agaaaagtct ctcagtgaca aaagcgatgc atagcccggt    60
gctagcatgc gctgagcttt                                               80

<210> SEQ ID NO 113
<211> LENGTH: 702
<212> TYPE: DNA
<213> ORGANISM: Discosoma sp.
<220> FEATURE:
<223> OTHER INFORMATION: red fluorescent protein (RFP) reporter protein

<400> SEQUENCE: 113
atggcttcct ccgaagacgt tatcaaagag ttcatgcgtt tcaaagttcg tatggaaggt    60
tccgttaacg gtcacgagtt cgaaatcgaa ggtgaaggtg aaggtcgtcc gtacgaaggt   120
acgcagaccg ctaaactgaa agttaccaaa ggtggtccgc tgccgttcgc ttgggacatc   180
ctgtccccgc agttccagta cggttccaaa gcttacgtta acacccggc tgacatcccg    240 gactacctga aactgtcctt cccggaaggt ttcaaatggg aacgtgttat gaacttcgaa   300
gacggtggtg ttgttaccgt tacccaggac tcctccctgc aagacggtga gttcatctac   360
aaagttaaac tgcgtggtac taacttcccg tccgacggtc cggttatgca gaaaaaaacc   420
atgggttggg aagcttccac cgaacgtatg tacccggaag acggtgctct gaaaggtgaa   480
atcaaaatgc gtctgaaact gaaagacggt ggtcactacg acgctgaagt taaaaccacc   540
tacatggcta aaaaaccggt tcagctgccg ggtgcttaca aaaccgacat caaactggac   600
atcacctccc acaacgaaga ctacaccatc gttgaacagt acgaacgtgc tgaaggtcgt   660
cactccaccg gtgctgcagc aaacgacgaa aactacgctt aa                     702

<210> SEQ ID NO 114
<211> LENGTH: 16
<212> TYPE: DNA
<213> ORGANISM: Artificial Sequence
<220> FEATURE:
<223> OTHER INFORMATION: synthetic target DNA sequence operator for McbR
      repressor

<400> SEQUENCE: 114
tgaacagctt ggtcta                                                   16

<210> SEQ ID NO 115
<211> LENGTH: 18
<212> TYPE: DNA
<213> ORGANISM: Artificial Sequence
<220> FEATURE:
<223> OTHER INFORMATION: synthetic target DNA sequence operator for UidR
      repressor

<400> SEQUENCE: 115
ctattggtta accaattt                                                 18

<210> SEQ ID NO 116
<211> LENGTH: 20
<212> TYPE: DNA
<213> ORGANISM: Artificial Sequence
<220> FEATURE:
<223> OTHER INFORMATION: synthetic target DNA sequence operator for
      BM3R1 repressor

<400> SEQUENCE: 116
```
cggaatgaac gttcattccg                                          20

<210> SEQ ID NO 117
<211> LENGTH: 22
<212> TYPE: DNA
<213> ORGANISM: Artificial Sequence
<220> FEATURE:
<223> OTHER INFORMATION: synthetic target DNA sequence operator for AmtR
      repressor

<400> SEQUENCE: 117
attatctata gatcgataga aa                                       22

<210> SEQ ID NO 118
<211> LENGTH: 22
<212> TYPE: DNA
<213> ORGANISM: Artificial Sequence
<220> FEATURE:
<223> OTHER INFORMATION: synthetic target DNA sequence operator for BetI
      repressor

<400> SEQUENCE: 118
ttatattgaa cgtccaatga at                                       22

<210> SEQ ID NO 119
<211> LENGTH: 22
<212> TYPE: DNA
<213> ORGANISM: Artificial Sequence
<220> FEATURE:
<223> OTHER INFORMATION: synthetic target DNA sequence operator for HapR
      repressor

<400> SEQUENCE: 119
ttattgattt ttaatcaaat aa                                       22

<210> SEQ ID NO 120
<211> LENGTH: 22
<212> TYPE: DNA
<213> ORGANISM: Artificial Sequence
<220> FEATURE:
<223> OTHER INFORMATION: synthetic target DNA sequence operator for
      HlyIIR repressor

<400> SEQUENCE: 120
tttaaacaag aattttaaat at                                       22

<210> SEQ ID NO 121
<211> LENGTH: 22
<212> TYPE: DNA
<213> ORGANISM: Artificial Sequence
<220> FEATURE:
<223> OTHER INFORMATION: synthetic target DNA sequence operator for SmcR
      repressor

<400> SEQUENCE: 121
ttattgataa atctgcgtaa aa                                       22

<210> SEQ ID NO 122
<211> LENGTH: 24
<212> TYPE: DNA
<213> ORGANISM: Artificial Sequence
<220> FEATURE:
<223> OTHER INFORMATION: synthetic target DNA sequence operator for AcrR
      repressor

<400> SEQUENCE: 122

```
tacatacatt tatgaatgta tgta                                            24

<210> SEQ ID NO 123
<211> LENGTH: 24
<212> TYPE: DNA
<213> ORGANISM: Artificial Sequence
<220> FEATURE:
<223> OTHER INFORMATION: synthetic target DNA sequence operator for ArpA
      repressor

<400> SEQUENCE: 123
cgacatacgg gacgccccgt ttat                                            24

<210> SEQ ID NO 124
<211> LENGTH: 24
<212> TYPE: DNA
<213> ORGANISM: Artificial Sequence
<220> FEATURE:
<223> OTHER INFORMATION: synthetic target DNA sequence operator for LmrA
      repressor

<400> SEQUENCE: 124
agataataga ccagtcacta tatt                                            24

<210> SEQ ID NO 125
<211> LENGTH: 26
<212> TYPE: DNA
<213> ORGANISM: Artificial Sequence
<220> FEATURE:
<223> OTHER INFORMATION: synthetic target DNA sequence operator for BarA
      repressor

<400> SEQUENCE: 125
agatacatac caaccggttc ttttga                                          26

<210> SEQ ID NO 126
<211> LENGTH: 26
<212> TYPE: DNA
<213> ORGANISM: Artificial Sequence
<220> FEATURE:
<223> OTHER INFORMATION: synthetic target DNA sequence operator for QacR
      repressor

<400> SEQUENCE: 126
cttatagacc gatcgcacgg tctata                                          26

<210> SEQ ID NO 127
<211> LENGTH: 26
<212> TYPE: DNA
<213> ORGANISM: Artificial Sequence
<220> FEATURE:
<223> OTHER INFORMATION: synthetic target DNA sequence operator for TylP
      repressor

<400> SEQUENCE: 127
atacaaaccg cgtcagcggt ttgtaa                                          26

<210> SEQ ID NO 128
<211> LENGTH: 27
<212> TYPE: DNA
<213> ORGANISM: Artificial Sequence
<220> FEATURE:
<223> OTHER INFORMATION: synthetic target DNA sequence operator for MtrR
      repressor

<400> SEQUENCE: 128
tttttatccg tgcaatcgtg tatgtat                                         27
```

```
<210> SEQ ID NO 129
<211> LENGTH: 28
<212> TYPE: DNA
<213> ORGANISM: Artificial Sequence
<220> FEATURE:
<223> OTHER INFORMATION: synthetic target DNA sequence operator for FarA
      repressor

<400> SEQUENCE: 129
gatacgaacg ggacggacgg tttgcagc                                             28

<210> SEQ ID NO 130
<211> LENGTH: 28
<212> TYPE: DNA
<213> ORGANISM: Artificial Sequence
<220> FEATURE:
<223> OTHER INFORMATION: synthetic target DNA sequence operator for IcaR
      Se repressor

<400> SEQUENCE: 130
acaacctaac taacgaaagg taggtgaa                                             28

<210> SEQ ID NO 131
<211> LENGTH: 29
<212> TYPE: DNA
<213> ORGANISM: Artificial Sequence
<220> FEATURE:
<223> OTHER INFORMATION: synthetic target DNA sequence operator for ScbR
      repressor

<400> SEQUENCE: 131
gaaaaaaaac cgctctagtc tgtatctta                                            29

<210> SEQ ID NO 132
<211> LENGTH: 30
<212> TYPE: DNA
<213> ORGANISM: Artificial Sequence
<220> FEATURE:
<223> OTHER INFORMATION: synthetic target DNA sequence operator for PhlF
      repressor

<400> SEQUENCE: 132
atgatacgaa acgtaccgta tcgttaaggt                                           30

<210> SEQ ID NO 133
<211> LENGTH: 30
<212> TYPE: DNA
<213> ORGANISM: Artificial Sequence
<220> FEATURE:
<223> OTHER INFORMATION: synthetic target DNA sequence operator for SmeT
      repressor

<400> SEQUENCE: 133
gtttacaaac aaacaagcat gtatgtatat                                           30

<210> SEQ ID NO 134
<211> LENGTH: 31
<212> TYPE: DNA
<213> ORGANISM: Artificial Sequence
<220> FEATURE:
<223> OTHER INFORMATION: synthetic target DNA sequence operator for MphR
      repressor

<400> SEQUENCE: 134
gaatataacc gacgtgactg ttacatttag g                                         31
```

```
<210> SEQ ID NO 135
<211> LENGTH: 32
<212> TYPE: DNA
<213> ORGANISM: Artificial Sequence
<220> FEATURE:
<223> OTHER INFORMATION: synthetic target DNA sequence operator for LuxT
      repressor

<400> SEQUENCE: 135
ttcggtttac tttgtttaga atacccacgt ct                                    32

<210> SEQ ID NO 136
<211> LENGTH: 38
<212> TYPE: DNA
<213> ORGANISM: Artificial Sequence
<220> FEATURE:
<223> OTHER INFORMATION: synthetic target DNA sequence operator for PsrA
      repressor

<400> SEQUENCE: 136
agcagggctg aaacgtatgt ttcaaacacc tgtttctg                              38

<210> SEQ ID NO 137
<211> LENGTH: 40
<212> TYPE: DNA
<213> ORGANISM: Artificial Sequence
<220> FEATURE:
<223> OTHER INFORMATION: synthetic target DNA sequence operator for TtgR
      repressor

<400> SEQUENCE: 137
cagcagtatt tacaaacaac catgaatgta agtatattcc                            40

<210> SEQ ID NO 138
<211> LENGTH: 41
<212> TYPE: DNA
<213> ORGANISM: Artificial Sequence
<220> FEATURE:
<223> OTHER INFORMATION: synthetic target DNA sequence operator for VarR
      repressor

<400> SEQUENCE: 138
cacttgtaca tcgtataact ctcatatacg ttgtagaaca g                          41

<210> SEQ ID NO 139
<211> LENGTH: 55
<212> TYPE: DNA
<213> ORGANISM: Artificial Sequence
<220> FEATURE:
<223> OTHER INFORMATION: synthetic target DNA sequence operator for EthR
      repressor

<400> SEQUENCE: 139
gtgtcgatag tgtcgacatc tcgttgacgg cctcgacatt acgttgatag cgtgg           55

<210> SEQ ID NO 140
<211> LENGTH: 6
<212> TYPE: PRT
<213> ORGANISM: Artificial Sequence
<220> FEATURE:
<223> OTHER INFORMATION: synthetic His-6 tag, amino-terminal 6x-His tag

<400> SEQUENCE: 140

His His His His His His
1               5
```

```
<210> SEQ ID NO 141
<211> LENGTH: 22
<212> TYPE: PRT
<213> ORGANISM: Artificial Sequence
<220> FEATURE:
<223> OTHER INFORMATION: synthetic N-terminal His-6 tag with cleavable
      PreScission protease cleavage site

<400> SEQUENCE: 141

Met Gly Ser Ser His His His His His His Ser Ser Gly Leu Glu Val
1               5                   10                  15

Leu Phe Gln Gly Pro His
            20

<210> SEQ ID NO 142
<211> LENGTH: 36
<212> TYPE: DNA
<213> ORGANISM: Artificial Sequence
<220> FEATURE:
<223> OTHER INFORMATION: synthetic repressed pOR1 promoter

<400> SEQUENCE: 142
tttgacatac ctctggcggt gatatataat ggttgc                                36

<210> SEQ ID NO 143
<211> LENGTH: 289
<212> TYPE: DNA
<213> ORGANISM: Artificial Sequence
<220> FEATURE:
<223> OTHER INFORMATION: synthetic upstream inducible promoter Pbad

<400> SEQUENCE: 143
agaaaccaat tgtccatatt gcatcagaca ttgccgtcac tgcgtctttt actggctctt      60
ctcgctaacc aaaccggtaa ccccgcttat taaaagcatt ctgtaacaaa gcgggaccaa     120
agccatgaca aaaacgcgta acaaaagtgt ctataatcac ggcagaaaag tccacattga     180
ttatttgcac ggcgtcacac tttgctatgc catagcattt ttatccataa gattagcgga     240
tcctacctga cgctttttat cgcaactctc tactgtttct ccatacccg                 289

<210> SEQ ID NO 144
<211> LENGTH: 84
<212> TYPE: DNA
<213> ORGANISM: Artificial Sequence
<220> FEATURE:
<223> OTHER INFORMATION: synthetic upstream inducible promoter Ptac

<400> SEQUENCE: 144
ggcaaatatt ctgaaatgag ctgttgacaa ttaatcatcg gctcgtataa tgtgtggaat      60
tgtgagcgga taacaatttc acac                                             84

<210> SEQ ID NO 145
<211> LENGTH: 78
<212> TYPE: DNA
<213> ORGANISM: Artificial Sequence
<220> FEATURE:
<223> OTHER INFORMATION: synthetic upstream inducible promoter Modified-
      Ptac

<400> SEQUENCE: 145
ggcaaatatt ctgaaatgag ctgataaatg tgagcggata acattgacat tgtgagcgga      60
taacaagata ctgagcac                                                    78

<210> SEQ ID NO 146
```

```
<211> LENGTH: 21
<212> TYPE: DNA
<213> ORGANISM: Artificial Sequence
<220> FEATURE:
<223> OTHER INFORMATION: synthetic super-fold gfp ribosome binding
      sequence (SDA)

<400> SEQUENCE: 146
actagaagga ggaaaaaaat g                                              21

<210> SEQ ID NO 147
<211> LENGTH: 12
<212> TYPE: DNA
<213> ORGANISM: Artificial Sequence
<220> FEATURE:
<223> OTHER INFORMATION: synthetic fused cI-gfp gene short linker
      sequence

<400> SEQUENCE: 147
ggcggtggcg gt                                                        12

<210> SEQ ID NO 148
<211> LENGTH: 21
<212> TYPE: DNA
<213> ORGANISM: Artificial Sequence
<220> FEATURE:
<223> OTHER INFORMATION: synthetic ribosome binding sequence SDmut

<400> SEQUENCE: 148
actagaacca tgaaaaaagt g                                              21

<210> SEQ ID NO 149
<211> LENGTH: 43
<212> TYPE: DNA
<213> ORGANISM: Artificial Sequence
<220> FEATURE:
<223> OTHER INFORMATION: synthetic pD/E20J T5 bacteriophage 5' UTR
      spacer sequence

<400> SEQUENCE: 149
agttcgatga gagcgataac cctctacaaa taattttgtt taa                      43

<210> SEQ ID NO 150
<211> LENGTH: 42
<212> TYPE: DNA
<213> ORGANISM: Artificial Sequence
<220> FEATURE:
<223> OTHER INFORMATION: synthetic pH207J T5 bacteriophage 5' UTR spacer
      sequence

<400> SEQUENCE: 150
ataaattgat aaacaaaaac ctctacaaat aattttgttt aa                       42

<210> SEQ ID NO 151
<211> LENGTH: 43
<212> TYPE: DNA
<213> ORGANISM: Artificial Sequence
<220> FEATURE:
<223> OTHER INFORMATION: synthetic pN25J T5 bacteriophage 5' UTR spacer
      sequence

<400> SEQUENCE: 151
ataaatttga gagaggagtt cctctacaaa taattttgtt taa                      43

<210> SEQ ID NO 152
<211> LENGTH: 43
<212> TYPE: DNA
```

```
<213> ORGANISM: Artificial Sequence
<220> FEATURE:
<223> OTHER INFORMATION: synthetic pG25J T5 bacteriophage 5' UTR spacer
      sequence

<400> SEQUENCE: 152
attaaagagg agaaattaac cctctacaaa taattttgtt taa                        43

<210> SEQ ID NO 153
<211> LENGTH: 43
<212> TYPE: DNA
<213> ORGANISM: Artificial Sequence
<220> FEATURE:
<223> OTHER INFORMATION: synthetic pJ5J T5 bacteriophage 5' UTR spacer
      sequence

<400> SEQUENCE: 153
aaacctaatg gatcgacctt cctctacaaa taattttgtt taa                        43

<210> SEQ ID NO 154
<211> LENGTH: 42
<212> TYPE: DNA
<213> ORGANISM: Artificial Sequence
<220> FEATURE:
<223> OTHER INFORMATION: synthetic pA1J T7 bacteriophage 5' UTR spacer
      sequence

<400> SEQUENCE: 154
atcgagaggg acacggcgac ctctacaaat aattttgttt aa                         42

<210> SEQ ID NO 155
<211> LENGTH: 42
<212> TYPE: DNA
<213> ORGANISM: Artificial Sequence
<220> FEATURE:
<223> OTHER INFORMATION: synthetic pA2J T7 bacteriophage 5' UTR spacer
      sequence

<400> SEQUENCE: 155
gctaggtaac actagcagcc ctctacaaat aattttgttt aa                         42

<210> SEQ ID NO 156
<211> LENGTH: 42
<212> TYPE: DNA
<213> ORGANISM: Artificial Sequence
<220> FEATURE:
<223> OTHER INFORMATION: synthetic pA3J T7 bacteriophage 5' UTR spacer
      sequence

<400> SEQUENCE: 156
atgaaacgac agtgagtcac ctctacaaat aattttgttt aa                         42

<210> SEQ ID NO 157
<211> LENGTH: 43
<212> TYPE: DNA
<213> ORGANISM: Artificial Sequence
<220> FEATURE:
<223> OTHER INFORMATION: synthetic phi10J T7 bacteriophage 5' UTR spacer
      sequence

<400> SEQUENCE: 157
agggagacca caacggtttc cctctacaaa taattttgtt taa                        43

<210> SEQ ID NO 158
<211> LENGTH: 43
<212> TYPE: DNA
<213> ORGANISM: Artificial Sequence
```

```
<220> FEATURE:
<223> OTHER INFORMATION: synthetic DG146aJ high-transcription escape 5'
      UTR spacer sequence

<400> SEQUENCE: 158
attaaaaaac ctgctaggat cctctacaaa taattttgtt taa                    43

<210> SEQ ID NO 159
<211> LENGTH: 43
<212> TYPE: DNA
<213> ORGANISM: Artificial Sequence
<220> FEATURE:
<223> OTHER INFORMATION: synthetic DG122J high-transcription escape 5'
      UTR spacer sequence

<400> SEQUENCE: 159
ataaaggaaa acggtcaggt cctctacaaa taattttgtt taa                    43

<210> SEQ ID NO 160
<211> LENGTH: 43
<212> TYPE: DNA
<213> ORGANISM: Artificial Sequence
<220> FEATURE:
<223> OTHER INFORMATION: synthetic DG131aJ high-transcription escape 5'
      UTR spacer sequence

<400> SEQUENCE: 160
ataggttaaa agcctgtcat cctctacaaa taattttgtt taa                    43

<210> SEQ ID NO 161
<211> LENGTH: 48
<212> TYPE: DNA
<213> ORGANISM: Artificial Sequence
<220> FEATURE:
<223> OTHER INFORMATION: synthetic MhpR3hppJ carbon utilization 5' UTR
      spacer sequence

<400> SEQUENCE: 161
acaataaaaa atcatttaca tgtttcctct acaaataatt ttgtttaa               48

<210> SEQ ID NO 162
<211> LENGTH: 48
<212> TYPE: DNA
<213> ORGANISM: Artificial Sequence
<220> FEATURE:
<223> OTHER INFORMATION: synthetic GlcCJ carbon utilization 5' UTR
      spacer sequence

<400> SEQUENCE: 162
agaagcagcg cgcaaaaatc agctgcctct acaaataatt ttgtttaa               48

<210> SEQ ID NO 163
<211> LENGTH: 48
<212> TYPE: DNA
<213> ORGANISM: Artificial Sequence
<220> FEATURE:
<223> OTHER INFORMATION: synthetic FucRPfucPJ carbon utilization 5' UTR
      spacer sequence

<400> SEQUENCE: 163
atgagttcat ttcagacagg caaatcctct acaaataatt ttgtttaa               48

<210> SEQ ID NO 164
<211> LENGTH: 48
<212> TYPE: DNA
<213> ORGANISM: Artificial Sequence
<220> FEATURE:
```

<223> OTHER INFORMATION: synthetic FuncRPfucAJ carbon utilization 5'
      UTR spacer sequence

<400> SEQUENCE: 164
aacttgcagt tatttactgt gattacctct acaaataatt tgtttaa                 48

<210> SEQ ID NO 165
<211> LENGTH: 48
<212> TYPE: DNA
<213> ORGANISM: Artificial Sequence
<220> FEATURE:
<223> OTHER INFORMATION: synthetic ChbRNagCJ carbon utilization 5' UTR
      spacer sequence

<400> SEQUENCE: 165
agccacaaaa aaagtcatgt tggttcctct acaaataatt tgtttaa                 48

<210> SEQ ID NO 166
<211> LENGTH: 53
<212> TYPE: DNA
<213> ORGANISM: Artificial Sequence
<220> FEATURE:
<223> OTHER INFORMATION: synthetic AraCJ carbon utilization 5' UTR
      spacer sequence

<400> SEQUENCE: 166
acacagtcac ttatcttttu gttaaaaggt cctctacaaa taattttgtt taa          53

(Note: corrected—line reads:)
acacagtcac ttatccttta gttaaaaggt cctctacaaa taattttgtt taa          53

<210> SEQ ID NO 167
<211> LENGTH: 43
<212> TYPE: DNA
<213> ORGANISM: Artificial Sequence
<220> FEATURE:
<223> OTHER INFORMATION: synthetic AntiescapeJ anti-escaping sequence 5'
      UTR spacer sequence

<400> SEQUENCE: 167
atccggaatc ctcttcccgg cctctacaaa taattttgtt taa                     43

<210> SEQ ID NO 168
<211> LENGTH: 48
<212> TYPE: DNA
<213> ORGANISM: Artificial Sequence
<220> FEATURE:
<223> OTHER INFORMATION: synthetic LeiQiJ 5' UTR spacer sequence

<400> SEQUENCE: 168
aacaaaataa aaaggagtcg ctcaccctct acaaataatt tgtttaa                 48

<210> SEQ ID NO 169
<211> LENGTH: 43
<212> TYPE: DNA
<213> ORGANISM: Artificial Sequence
<220> FEATURE:
<223> OTHER INFORMATION: synthetic pD/E20RBS T5 bacteriophage 5' UTR
      spacer sequence

<400> SEQUENCE: 169
agttcgatga gagcgataac agttccagat tcaggaacta taa                     43

<210> SEQ ID NO 170
<211> LENGTH: 42
<212> TYPE: DNA
<213> ORGANISM: Artificial Sequence
<220> FEATURE:
<223> OTHER INFORMATION: synthetic pH207RBS T5 bacteriophage 5' UTR
      spacer sequence <210> SEQ ID NO 171
<211> LENGTH: 43
<212> TYPE: DNA
<213> ORGANISM: Artificial Sequence
<220> FEATURE:
<223> OTHER INFORMATION: synthetic pN25RBS T5 bacteriophage 5' UTR
      spacer sequence

<400> SEQUENCE: 171
ataaatttga gagaggagtt agttccagat tcaggaacta taa                    43

<210> SEQ ID NO 172
<211> LENGTH: 43
<212> TYPE: DNA
<213> ORGANISM: Artificial Sequence
<220> FEATURE:
<223> OTHER INFORMATION: synthetic pG25RBS T5 bacteriophage 5' UTR
      spacer sequence

<400> SEQUENCE: 172
attaaagagg agaaattaac agttccagat tcaggaacta taa                    43

<210> SEQ ID NO 173
<211> LENGTH: 43
<212> TYPE: DNA
<213> ORGANISM: Artificial Sequence
<220> FEATURE:
<223> OTHER INFORMATION: synthetic pJ5RBS T5 bacteriophage 5' UTR spacer
      sequence

<400> SEQUENCE: 173
aaacctaatg gatcgacctt agttccagat tcaggaacta taa                    43

<210> SEQ ID NO 174
<211> LENGTH: 42
<212> TYPE: DNA
<213> ORGANISM: Artificial Sequence
<220> FEATURE:
<223> OTHER INFORMATION: synthetic pA1RBS T7 bacteriophage 5' UTR spacer
      sequence

<400> SEQUENCE: 174
atcgagaggg acacggcgaa gttccagatt caggaactat aa                     42

<210> SEQ ID NO 175
<211> LENGTH: 42
<212> TYPE: DNA
<213> ORGANISM: Artificial Sequence
<220> FEATURE:
<223> OTHER INFORMATION: synthetic pA2RBS T7 bacteriophage 5' UTR spacer
      sequence

<400> SEQUENCE: 175
gctaggtaac actagcagca gttccagatt caggaactat aa                     42

<210> SEQ ID NO 176
<211> LENGTH: 42
<212> TYPE: DNA
<213> ORGANISM: Artificial Sequence
<220> FEATURE:
<223> OTHER INFORMATION: synthetic pA3RBS T7 bacteriophage 5' UTR spacer
      sequence

<400> SEQUENCE: 176
atgaaacgac agtgagtcaa gttccagatt caggaactat aa                42

<210> SEQ ID NO 177
<211> LENGTH: 43
<212> TYPE: DNA
<213> ORGANISM: Artificial Sequence
<220> FEATURE:
<223> OTHER INFORMATION: synthetic phi10RBS T7 bacteriophage 5' UTR
      spacer sequence

<400> SEQUENCE: 177
agggagacca acgggtttc agttccagat tcaggaacta taa                43

<210> SEQ ID NO 178
<211> LENGTH: 43
<212> TYPE: DNA
<213> ORGANISM: Artificial Sequence
<220> FEATURE:
<223> OTHER INFORMATION: synthetic DG146aRBS high-transcription escape
      5' UTR spacer sequence

<400> SEQUENCE: 178
attaaaaaac ctgctaggat agttccagat tcaggaacta taa                43

<210> SEQ ID NO 179
<211> LENGTH: 43
<212> TYPE: DNA
<213> ORGANISM: Artificial Sequence
<220> FEATURE:
<223> OTHER INFORMATION: synthetic DG122RBS high-transcription escape
      5' UTR spacer sequence

<400> SEQUENCE: 179
ataaaggaaa acggtcaggt agttccagat tcaggaacta taa                43

<210> SEQ ID NO 180
<211> LENGTH: 43
<212> TYPE: DNA
<213> ORGANISM: Artificial Sequence
<220> FEATURE:
<223> OTHER INFORMATION: synthetic DG131aRBS high-transcription escape
      5' UTR spacer sequence

<400> SEQUENCE: 180
ataggttaaa agcctgtcat agttccagat tcaggaacta taa                43

<210> SEQ ID NO 181
<211> LENGTH: 48
<212> TYPE: DNA
<213> ORGANISM: Artificial Sequence
<220> FEATURE:
<223> OTHER INFORMATION: synthetic MhpR3hppRBS carbon utilization 5' UTR
      spacer sequence

<400> SEQUENCE: 181
acaataaaaa atcatttaca tgtttagttc cagattcagg aactataa                48

<210> SEQ ID NO 182
<211> LENGTH: 48
<212> TYPE: DNA
<213> ORGANISM: Artificial Sequence
<220> FEATURE:
<223> OTHER INFORMATION: synthetic GlcCRBS carbon utilization 5' UTR
      spacer sequence

<400> SEQUENCE: 182
agaagcagcg cgcaaaaatc agctgagttc cagattcagg aactataa    48

<210> SEQ ID NO 183
<211> LENGTH: 48
<212> TYPE: DNA
<213> ORGANISM: Artificial Sequence
<220> FEATURE:
<223> OTHER INFORMATION: synthetic FucRPfucPRBS carbon utilization 5'
      UTR spacer sequence

<400> SEQUENCE: 183
atgagttcat ttcagacagg caaatagttc cagattcagg aactataa    48

<210> SEQ ID NO 184
<211> LENGTH: 48
<212> TYPE: DNA
<213> ORGANISM: Artificial Sequence
<220> FEATURE:
<223> OTHER INFORMATION: synthetic FuncRPfucARBS carbon utilization 5'
      UTR spacer sequence

<400> SEQUENCE: 184
aacttgcagt tatttactgt gattaagttc cagattcagg aactataa    48

<210> SEQ ID NO 185
<211> LENGTH: 48
<212> TYPE: DNA
<213> ORGANISM: Artificial Sequence
<220> FEATURE:
<223> OTHER INFORMATION: synthetic ChbRNagCRBS carbon utilization 5'
      UTR spacer sequence

<400> SEQUENCE: 185
agccacaaaa aaagtcatgt tggttagttc cagattcagg aactataa    48

<210> SEQ ID NO 186
<211> LENGTH: 53
<212> TYPE: DNA
<213> ORGANISM: Artificial Sequence
<220> FEATURE:
<223> OTHER INFORMATION: synthetic AraCRBS carbon utilization 5' UTR
      spacer sequence

<400> SEQUENCE: 186
acacagtcac ttatctttta gttaaaaggt agttccagat tcaggaacta taa    53

<210> SEQ ID NO 187
<211> LENGTH: 43
<212> TYPE: DNA
<213> ORGANISM: Artificial Sequence
<220> FEATURE:
<223> OTHER INFORMATION: synthetic AntiescapeRBS anti-escaping sequence
      5' UTR spacer sequence

<400> SEQUENCE: 187
atccggaatc ctcttcccgg agttccagat tcaggaacta taa    43

<210> SEQ ID NO 188
<211> LENGTH: 48
<212> TYPE: DNA
<213> ORGANISM: Artificial Sequence
<220> FEATURE:
<223> OTHER INFORMATION: synthetic LeiQiRBS 5' UTR spacer sequence

<400> SEQUENCE: 188
aacaaaataa aaaggagtcg ctcacagttc cagattcagg aactataa    48

<210> SEQ ID NO 189
<211> LENGTH: 30
<212> TYPE: DNA
<213> ORGANISM: Artificial Sequence
<220> FEATURE:
<223> OTHER INFORMATION: synthetic OmpA4 hairpin stem loop 5' UTR spacer
      sequence

<400> SEQUENCE: 189
gatcaccagg gggatccccc ggtgaaggat                                    30

<210> SEQ ID NO 190
<211> LENGTH: 38
<212> TYPE: DNA
<213> ORGANISM: Artificial Sequence
<220> FEATURE:
<223> OTHER INFORMATION: synthetic OmpA952 hairpin stem loop 5' UTR
      spacer sequence

<400> SEQUENCE: 190
gatcgcccac cggcagctgc cggtgggcga tcaaggat                           38

<210> SEQ ID NO 191
<211> LENGTH: 45
<212> TYPE: DNA
<213> ORGANISM: Artificial Sequence
<220> FEATURE:
<223> OTHER INFORMATION: synthetic OmpA29 hairpin stem loop 5' UTR
      spacer sequence

<400> SEQUENCE: 191
gatcatcggt agagttaata ttgagcagat cccccggtga aggat                   45

<210> SEQ ID NO 192
<211> LENGTH: 36
<212> TYPE: DNA
<213> ORGANISM: Artificial Sequence
<220> FEATURE:
<223> OTHER INFORMATION: synthetic papA hairpin stem loop 5' UTR spacer
      sequence

<400> SEQUENCE: 192
attgatctgg ttattaaagg taatcgggtc atttta                             36

<210> SEQ ID NO 193
<211> LENGTH: 41
<212> TYPE: DNA
<213> ORGANISM: Artificial Sequence
<220> FEATURE:
<223> OTHER INFORMATION: synthetic pufBA hairpin stem loop 5' UTR spacer
      sequence

<400> SEQUENCE: 193
gttctccacg ggtgggatga gcccctcgtg gtggaaatgc g                       41

<210> SEQ ID NO 194
<211> LENGTH: 27
<212> TYPE: DNA
<213> ORGANISM: Artificial Sequence
<220> FEATURE:
<223> OTHER INFORMATION: synthetic gene32 hairpin stem loop 5' UTR
      spacer sequence

<400> SEQUENCE: 194
agcatgaggt aaagtgtcat gcaccaa                                       27

<210> SEQ ID NO 195
<211> LENGTH: 38
<212> TYPE: DNA
<213> ORGANISM: Artificial Sequence
<220> FEATURE:
<223> OTHER INFORMATION: synthetic pHP4 hairpin stem loop 5' UTR spacer
      sequence

<400> SEQUENCE: 195
acgtcgactt atctcgagtg agatattgtt gacggtac                              38

<210> SEQ ID NO 196
<211> LENGTH: 37
<212> TYPE: DNA
<213> ORGANISM: Artificial Sequence
<220> FEATURE:
<223> OTHER INFORMATION: synthetic pHP10 hairpin stem loop 5' UTR spacer
      sequence

<400> SEQUENCE: 196
acgtcgactt atctcgagtg agataagttg acggtac                               37

<210> SEQ ID NO 197
<211> LENGTH: 51
<212> TYPE: DNA
<213> ORGANISM: Artificial Sequence
<220> FEATURE:
<223> OTHER INFORMATION: synthetic pHP17 hairpin stem loop 5' UTR spacer
      sequence

<400> SEQUENCE: 197
acgtcgactt atctcgagac tgcagttcaa tagagatatt gttgacggta c               51

<210> SEQ ID NO 198
<211> LENGTH: 52
<212> TYPE: DNA
<213> ORGANISM: Artificial Sequence
<220> FEATURE:
<223> OTHER INFORMATION: synthetic Ribo50 hairpin stem loop (ribozyme)
      5' UTR spacer sequence

<400> SEQUENCE: 198
gactgtcacc ggatgtgctt tccggtctga tgagtccgtg aggacgaaac ag              52

<210> SEQ ID NO 199
<211> LENGTH: 53
<212> TYPE: DNA
<213> ORGANISM: Artificial Sequence
<220> FEATURE:
<223> OTHER INFORMATION: synthetic OmpA952J hairpin stem loop 5' UTR
      spacer sequence

<400> SEQUENCE: 199
gatcaccagg gggatccccc ggtgaaggat cctctacaaa taattttgtt taa             53

<210> SEQ ID NO 200
<211> LENGTH: 61
<212> TYPE: DNA
<213> ORGANISM: Artificial Sequence
<220> FEATURE:
<223> OTHER INFORMATION: synthetic OmpA64J hairpin stem loop 5' UTR
      spacer sequence

<400> SEQUENCE: 200
gatcgcccac cggcagctgc cggtgggcga tcaaggatcc tctacaaata attttgttta     60
a                                                                     61

<210> SEQ ID NO 201
<211> LENGTH: 68
<212> TYPE: DNA
<213> ORGANISM: Artificial Sequence
<220> FEATURE:
<223> OTHER INFORMATION: synthetic OmpA29J hairpin stem loop 5' UTR
      spacer sequence

<400> SEQUENCE: 201
gatcatcggt agagttaata ttgagcagat cccccggtga aggatcctct acaaataatt    60
ttgtttaa                                                             68

<210> SEQ ID NO 202
<211> LENGTH: 59
<212> TYPE: DNA
<213> ORGANISM: Artificial Sequence
<220> FEATURE:
<223> OTHER INFORMATION: synthetic papAJ hairpin stem loop 5' UTR spacer
      sequence

<400> SEQUENCE: 202
attgatctgg ttattaaagg taatcgggtc attttacctc tacaaataat tttgtttaa     59

<210> SEQ ID NO 203
<211> LENGTH: 64
<212> TYPE: DNA
<213> ORGANISM: Artificial Sequence
<220> FEATURE:
<223> OTHER INFORMATION: synthetic pufBAJ hairpin stem loop 5' UTR
      spacer sequence

<400> SEQUENCE: 203
gttctccacg ggtgggatga gcccctcgtg gtggaaatgc gcctctacaa ataattttgt    60
ttaa                                                                 64

<210> SEQ ID NO 204
<211> LENGTH: 50
<212> TYPE: DNA
<213> ORGANISM: Artificial Sequence
<220> FEATURE:
<223> OTHER INFORMATION: synthetic gene32 hairpin stem loop 5' UTR
      spacer sequence

<400> SEQUENCE: 204
agcatgaggt aaagtgtcat gcaccaacct ctacaaataa ttttgtttaa               50

<210> SEQ ID NO 205
<211> LENGTH: 61
<212> TYPE: DNA
<213> ORGANISM: Artificial Sequence
<220> FEATURE:
<223> OTHER INFORMATION: synthetic pHP4J hairpin stem loop 5' UTR spacer
      sequence

<400> SEQUENCE: 205
acgtcgactt atctcgagtg agatattgtt gacggtaccc tctacaaata attttgttta    60
a                                                                    61

<210> SEQ ID NO 206
<211> LENGTH: 60
<212> TYPE: DNA
<213> ORGANISM: Artificial Sequence
<220> FEATURE:
<223> OTHER INFORMATION: synthetic pHP10J hairpin stem loop 5' UTR

```
              spacer sequence

<400> SEQUENCE: 206
acgtcgactt atctcgagtg agataagttg acggtaccct ctacaaataa ttttgtttaa      60

<210> SEQ ID NO 207
<211> LENGTH: 74
<212> TYPE: DNA
<213> ORGANISM: Artificial Sequence
<220> FEATURE:
<223> OTHER INFORMATION: synthetic pHP17J hairpin stem loop 5' UTR
      spacer sequence

<400> SEQUENCE: 207
acgtcgactt atctcgagac tgcagttcaa tagagatatt gttgacggta ccctctacaa      60
ataattttgt ttaa                                                        74

<210> SEQ ID NO 208
<211> LENGTH: 75
<212> TYPE: DNA
<213> ORGANISM: Artificial Sequence
<220> FEATURE:
<223> OTHER INFORMATION: synthetic RiboJ hairpin stem loop (ribozyme)
      5' UTR spacer sequence

<400> SEQUENCE: 208
gactgtcacc ggatgtgctt tccggtctga tgagtccgtg aggacgaaac agcctctaca      60
aataattttg tttaa                                                       75

<210> SEQ ID NO 209
<211> LENGTH: 80
<212> TYPE: DNA
<213> ORGANISM: Artificial Sequence
<220> FEATURE:
<223> OTHER INFORMATION: synthetic LtsvJ ribozyme

<400> SEQUENCE: 209
agtacgtctg agcgtgatac ccgctcactg aagatggccc ggtagggccg aaacgtacct      60
ctacaaataa ttttgtttaa                                                  80

<210> SEQ ID NO 210
<211> LENGTH: 80
<212> TYPE: DNA
<213> ORGANISM: Artificial Sequence
<220> FEATURE:
<223> OTHER INFORMATION: synthetic SccJ ribozyme

<400> SEQUENCE: 210
agatgctgta gtgggatgtg tgtctcacct gaagagtaca aaagtccgaa acggtatcct      60
ctacaaataa ttttgtttaa                                                  80

<210> SEQ ID NO 211
<211> LENGTH: 75
<212> TYPE: DNA
<213> ORGANISM: Artificial Sequence
<220> FEATURE:
<223> OTHER INFORMATION: synthetic RiboJ ribozyme

<400> SEQUENCE: 211
agctgtcacc ggatgtgctt tccggtctga tgagtccgtg aggacgaaac agcctctaca      60
aataattttg tttaa                                                       75
```

```
<210> SEQ ID NO 212
<211> LENGTH: 79
<212> TYPE: DNA
<213> ORGANISM: Artificial Sequence
<220> FEATURE:
<223> OTHER INFORMATION: synthetic SarJ ribozyme

<400> SEQUENCE: 212
agactgtcgc cggatgtgta tccgacctga cgatggccca aaagggccga aacagtcctc      60
tacaaataat tttgtttaa                                                   79

<210> SEQ ID NO 213
<211> LENGTH: 81
<212> TYPE: DNA
<213> ORGANISM: Artificial Sequence
<220> FEATURE:
<223> OTHER INFORMATION: synthetic PlmJ ribozyme

<400> SEQUENCE: 213
agtcataagt ctgggctaag cccactgatg agtcgctgaa atgcgacgaa acttatgacc      60
tctacaaata attttgttta a                                                81

<210> SEQ ID NO 214
<211> LENGTH: 75
<212> TYPE: DNA
<213> ORGANISM: Artificial Sequence
<220> FEATURE:
<223> OTHER INFORMATION: synthetic VtmoJ ribozyme

<400> SEQUENCE: 214
agtccgtagt ggatgtgtat ccactctgat gagtccgaaa ggacgaaacg gacctctaca      60
aataattttg tttaa                                                       75

<210> SEQ ID NO 215
<211> LENGTH: 86
<212> TYPE: DNA
<213> ORGANISM: Artificial Sequence
<220> FEATURE:
<223> OTHER INFORMATION: synthetic ChmJ ribozyme

<400> SEQUENCE: 215
agaagaggtc ggcacctgac gtcggtgtcc tgatgaagat ccatgacagg atcgaaacct      60
cttcctctac aaataatttt gtttaa                                           86

<210> SEQ ID NO 216
<211> LENGTH: 78
<212> TYPE: DNA
<213> ORGANISM: Artificial Sequence
<220> FEATURE:
<223> OTHER INFORMATION: synthetic ScvmJ ribozyme

<400> SEQUENCE: 216
agtactgtcg ccagacgtgg acccggcctg atgagtccga aggacgaaa cagtacctct       60 acaaataatt tgtttaa                                                     78

<210> SEQ ID NO 217
<211> LENGTH: 85
<212> TYPE: DNA
<213> ORGANISM: Artificial Sequence
<220> FEATURE:
<223> OTHER INFORMATION: synthetic SltJ ribozyme

<400> SEQUENCE: 217
```

```
aggacgtatg agactgactg aaacgccgtc tcactgatga ggccatggca ggccgaaacg    60
tccctctaca aataattttg tttaa                                         85

<210> SEQ ID NO 218
<211> LENGTH: 79
<212> TYPE: DNA
<213> ORGANISM: Artificial Sequence
<220> FEATURE:
<223> OTHER INFORMATION: synthetic PlmvJ ribozyme

<400> SEQUENCE: 218
aggaagagtc tgtgctaagc acactgacga gtctctgaga tgagacgaaa ctcttccctc    60
tacaaataat tttgtttaa                                                79

<210> SEQ ID NO 219
<211> LENGTH: 23
<212> TYPE: DNA
<213> ORGANISM: Artificial Sequence
<220> FEATURE:
<223> OTHER INFORMATION: synthetic pipaH9.8 promoter saturation
      mutagenesis forward primer
<220> FEATURE:
<221> NAME/KEY: modified_base
<222> LOCATION: (1)...(2)
<223> OTHER INFORMATION: n = g, a, c or t

<400> SEQUENCE: 219
nnataaaaaa gtgctgaatt cac                                           23

<210> SEQ ID NO 220
<211> LENGTH: 25
<212> TYPE: DNA
<213> ORGANISM: Artificial Sequence
<220> FEATURE:
<223> OTHER INFORMATION: synthetic pipaH9.8 promoter saturation
      mutagenesis reverse primer
<220> FEATURE:
<221> NAME/KEY: modified_base
<222> LOCATION: (1)...(2)
<223> OTHER INFORMATION: n = g, a, c or t

<400> SEQUENCE: 220
nnataaggat aaacaaaatt ggctg                                         25

<210> SEQ ID NO 221
<211> LENGTH: 80
<212> TYPE: DNA
<213> ORGANISM: Artificial Sequence
<220> FEATURE:
<223> OTHER INFORMATION: synthetic functional ECF promoter Pecf02 2817

<400> SEQUENCE: 221
catgacaaac aaaaacagat gcgttacgga actttacaaa aacgagacac tctaaccctt    60
tgcttgctca aattgcagct                                               80

<210> SEQ ID NO 222
<211> LENGTH: 80
<212> TYPE: DNA
<213> ORGANISM: Artificial Sequence
<220> FEATURE:
<223> OTHER INFORMATION: synthetic functional ECF promoter Pecf03 UP1198

<400> SEQUENCE: 222
cagtacaaaa ttttttagat gcgtttttaa cttcgttcct tttcggcgtt ctaataacca    60
aagctcagaa ataatagatg                                               80
```

<210> SEQ ID NO 223
<211> LENGTH: 80
<212> TYPE: DNA
<213> ORGANISM: Artificial Sequence
<220> FEATURE:
<223> OTHER INFORMATION: synthetic functional ECF promoter Pecf11 3726

<400> SEQUENCE: 223
atgcctccac accgctcgtc acatcctgtg atccactctt catcccgcta cgtaacacct    60
ctgcatcgcg aaccaaaacc                                                80

<210> SEQ ID NO 224
<211> LENGTH: 80
<212> TYPE: DNA
<213> ORGANISM: Artificial Sequence
<220> FEATURE:
<223> OTHER INFORMATION: synthetic functional ECF promoter Pecf12 UP807

<400> SEQUENCE: 224
cagtacaaaa ttttttagat gcgttgcggg aatctccccg gccgatgggc cgtttcccag    60
gtcgagtggc ctgaatcgga                                                80

<210> SEQ ID NO 225
<211> LENGTH: 80
<212> TYPE: DNA
<213> ORGANISM: Artificial Sequence
<220> FEATURE:
<223> OTHER INFORMATION: synthetic functional ECF promoter Pecf15 UP436

<400> SEQUENCE: 225
cagtacaaaa ttttttagat gcgttcttgg gaaccgaacg ccggtgcccg cgttcggttc    60
cggggatctt atcaactttt                                                80

<210> SEQ ID NO 226
<211> LENGTH: 80
<212> TYPE: DNA
<213> ORGANISM: Artificial Sequence
<220> FEATURE:
<223> OTHER INFORMATION: synthetic functional ECF promoter Pecf16 3622

<400> SEQUENCE: 226
cttggatgaa aagaaaccca ccgacggtgt aaccctggcg gccgatgcaa cgaactaact    60
cacaggacgt gctcagcacc                                                80

<210> SEQ ID NO 227
<211> LENGTH: 80
<212> TYPE: DNA
<213> ORGANISM: Artificial Sequence
<220> FEATURE:
<223> OTHER INFORMATION: synthetic functional ECF promoter Pecf17
      UP1691

<400> SEQUENCE: 227
cagtacaaaa ttttttagat gcgtttggtg aaccaaactc ttactcgact cgtgtcagta    60
agcgggaggt gatcgcgtgg                                                80

<210> SEQ ID NO 228
<211> LENGTH: 80
<212> TYPE: DNA
<213> ORGANISM: Artificial Sequence
<220> FEATURE:
<223> OTHER INFORMATION: synthetic functional ECF promoter Pecf18 UP1700

<400> SEQUENCE: 228
cagtacaaaa ttttttagat gcgtttgcat ccagattgtc tcggcggcgg taatgccata    60
agcaatgttc gatggcgcag                                                80

<210> SEQ ID NO 229
<211> LENGTH: 80
<212> TYPE: DNA
<213> ORGANISM: Artificial Sequence
<220> FEATURE:
<223> OTHER INFORMATION: synthetic functional ECF promoter Pecf19 UP1315

<400> SEQUENCE: 229
cagtacaaaa ttttttagat gcgtttcctc ccgctcctgt ggagcacgat cgaacgcgaa    60
cgcggtcact atacccatgc                                                80

<210> SEQ ID NO 230
<211> LENGTH: 80
<212> TYPE: DNA
<213> ORGANISM: Artificial Sequence
<220> FEATURE:
<223> OTHER INFORMATION: synthetic functional ECF promoter Pecf20 992

<400> SEQUENCE: 230
gcgcggataa aaatttcatt tgcccgcgac ggattccccg cccatctatc gttgaaccca    60
tcagctgcgt tcatcagcga                                                80

<210> SEQ ID NO 231
<211> LENGTH: 80
<212> TYPE: DNA
<213> ORGANISM: Artificial Sequence
<220> FEATURE:
<223> OTHER INFORMATION: synthetic functional ECF promoter Pecf21 UP4014

<400> SEQUENCE: 231
cagtacaaaa ttttttagat gcgttaggca acccttttc atccggcttc gtctatatct     60
atagaaaccg acaccaaacc                                                80

<210> SEQ ID NO 232
<211> LENGTH: 80
<212> TYPE: DNA
<213> ORGANISM: Artificial Sequence
<220> FEATURE:
<223> OTHER INFORMATION: synthetic functional ECF promoter Pecf22 UP1147

<400> SEQUENCE: 232
cagtacaaaa ttttttagat gcgttgttgt gaggaatcgc gctcctgcgc gaatcatccc    60
gtgtcgtccc ttcacctgcc                                                80

<210> SEQ ID NO 233
<211> LENGTH: 80
<212> TYPE: DNA
<213> ORGANISM: Artificial Sequence
<220> FEATURE:
<223> OTHER INFORMATION: synthetic functional ECF promoter Pecf24 UP69

<400> SEQUENCE: 233
cagtacaaaa ttttttagat gcgttacgga acgcagtctt ttcgtctgta tcaactccaa    60
aattcatcgt gcctaaacat                                                80

<210> SEQ ID NO 234

```
<211> LENGTH: 80
<212> TYPE: DNA
<213> ORGANISM: Artificial Sequence
<220> FEATURE:
<223> OTHER INFORMATION: synthetic functional ECF promoter Pecf25 UP4311

<400> SEQUENCE: 234
cagtacaaaa ttttttagat gcgtcgagga actcaaactg cgccattatc gtctagctaa      60
cagaggttct gcttgggagg                                                  80

<210> SEQ ID NO 235
<211> LENGTH: 80
<212> TYPE: DNA
<213> ORGANISM: Artificial Sequence
<220> FEATURE:
<223> OTHER INFORMATION: synthetic functional ECF promoter Pecf26 UP601

<400> SEQUENCE: 235
cagtacaaaa ttttttagat gcgtttggaa taaccggtcg cctccatccg tttacatacc      60
gaatcccggc agcgccggcc                                                  80

<210> SEQ ID NO 236
<211> LENGTH: 80
<212> TYPE: DNA
<213> ORGANISM: Artificial Sequence
<220> FEATURE:
<223> OTHER INFORMATION: synthetic functional ECF promoter Pecf29 UP371

<400> SEQUENCE: 236
cagtacaaaa ttttttagat gcgttccggg aacctttgt cggcacgaac atccaattgg       60
cggatgaaac actttgtctg                                                  80

<210> SEQ ID NO 237
<211> LENGTH: 80
<212> TYPE: DNA
<213> ORGANISM: Artificial Sequence
<220> FEATURE:
<223> OTHER INFORMATION: synthetic functional ECF promoter Pecf30 2079

<400> SEQUENCE: 237
accatccgta ttttttagg gatttataaa acttttccat ggcgtgcgtc gtctaataaa       60
tgggaaggag gaaatgatgt                                                  80

<210> SEQ ID NO 238
<211> LENGTH: 80
<212> TYPE: DNA
<213> ORGANISM: Artificial Sequence
<220> FEATURE:
<223> OTHER INFORMATION: synthetic functional ECF promoter Pecf31 34

<400> SEQUENCE: 238
caatggctga aaagaattgt aaaaaagatg aacgcttttg aatccggtgt cgtctcataa      60
ggcagaaaaa caaaaagggg                                                  80

<210> SEQ ID NO 239
<211> LENGTH: 80
<212> TYPE: DNA
<213> ORGANISM: Artificial Sequence
<220> FEATURE:
<223> OTHER INFORMATION: synthetic functional ECF promoter Pecf32 1122

<400> SEQUENCE: 239
gcgactttat ttaacagcgg catggccagg gaaccgatgc gtcaatcgca ccacacaatg      60
```

```
acaactgctc tcatcattga                                            80

<210> SEQ ID NO 240
<211> LENGTH: 80
<212> TYPE: DNA
<213> ORGANISM: Artificial Sequence
<220> FEATURE:
<223> OTHER INFORMATION: synthetic functional ECF promoter Pecf33 375

<400> SEQUENCE: 240
taagttgaac aattttgcac cttccgtcga accgtccgct gcatcgaccc gaccaacctt   60
gcgagacggc ctttgagcgt                                            80

<210> SEQ ID NO 241
<211> LENGTH: 80
<212> TYPE: DNA
<213> ORGANISM: Artificial Sequence
<220> FEATURE:
<223> OTHER INFORMATION: synthetic functional ECF promoter Pecf38 UP1322

<400> SEQUENCE: 241
cagtacaaaa ttttttagat gcgttgtaca accctcacgg gggtggacgt gtccaactgg   60
cgtggcagag gttctcgatt                                            80

<210> SEQ ID NO 242
<211> LENGTH: 80
<212> TYPE: DNA
<213> ORGANISM: Artificial Sequence
<220> FEATURE:
<223> OTHER INFORMATION: synthetic functional ECF promoter Pecf39 UP1413

<400> SEQUENCE: 242
cagtacaaaa ttttttagat gcgtttgtca accgtccacg acgcgctggc gtctggaagg   60
gtgacccagc cagaccagcg                                            80

<210> SEQ ID NO 243
<211> LENGTH: 80
<212> TYPE: DNA
<213> ORGANISM: Artificial Sequence
<220> FEATURE:
<223> OTHER INFORMATION: synthetic functional ECF promoter Pecf41 UP1141

<400> SEQUENCE: 243
cagtacaaaa ttttttagat gcgttcacgt cacaaacccg aaagctgaat cgtcatcccg   60
ttgaatccct caaacacgga                                            80

<210> SEQ ID NO 244
<211> LENGTH: 80
<212> TYPE: DNA
<213> ORGANISM: Artificial Sequence
<220> FEATURE:
<223> OTHER INFORMATION: synthetic functional ECF promoter Pecf42 UP4062

<400> SEQUENCE: 244
cagtacaaaa ttttttagat gcgttcgctg tcgatccggc ccgtcgtcgt tcgtcgtacc   60
cccgagagcc cgcgaaaggc                                            80
```